(12) United States Patent
Wu et al.

(10) Patent No.: US 12,371,408 B2
(45) Date of Patent: Jul. 29, 2025

(54) ARYL HYDROCARBON RECEPTOR AGONISTS AND USES THEREOF

(71) Applicant: NEXYS THERAPEUTICS, INC., San Diego, CA (US)

(72) Inventors: Tom Yao-Hsiang Wu, San Diego, CA (US); Qihui Jin, San Diego, CA (US)

(73) Assignee: NEXYS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/433,196

(22) Filed: Feb. 5, 2024

(65) Prior Publication Data

US 2024/0279185 A1    Aug. 22, 2024

Related U.S. Application Data

(63) Continuation of application No. PCT/US2023/012166, filed on Feb. 2, 2023.

(60) Provisional application No. 63/306,458, filed on Feb. 3, 2022.

(51) Int. Cl.
| | |
|---|---|
| C07D 239/14 | (2006.01) |
| A61K 31/505 | (2006.01) |
| A61K 31/506 | (2006.01) |
| A61K 31/655 | (2006.01) |
| A61K 31/675 | (2006.01) |
| C07D 239/42 | (2006.01) |
| C07F 9/6512 | (2006.01) |

(52) U.S. Cl.
CPC .......... *C07D 239/42* (2013.01); *A61K 31/505* (2013.01); *A61K 31/506* (2013.01); *A61K 31/655* (2013.01); *A61K 31/675* (2013.01); *C07F 9/6512* (2013.01)

(58) Field of Classification Search
CPC .. C07D 239/42; A61K 31/505; A61K 31/506; A61K 31/655; A61K 31/675; A61K 45/06; C07F 9/6512; A61P 1/04; A61P 1/12; A61P 25/14
See application file for complete search history.

(56) References Cited

FOREIGN PATENT DOCUMENTS

| WO | 2007/039216 A1 | 4/2007 |
|---|---|---|
| WO | 2021/127301 A1 | 6/2021 |
| WO | 2021175079 A1 | 9/2021 |
| WO | 2021185297 A1 | 9/2021 |

OTHER PUBLICATIONS

International app. No. PCT/US2023/012166, International Search Report, dated May 17, 2023.
International app. No. PCT/US2023/012166, Written Opinion, dated May 17, 2023.
Lawrence B. Paige, et al., "Activation of the aryl hydrocarbon receptor is essential for mediating the anti-inflammatory effects of a novel low-melecular-weight compound," Blood, vol. 112; No. 4, Aug. 15, 2008, pp. 1158-1165, retrieved from the internet: URL :http://ashpublications.org/blood/article-pdf/112/4/1158/1457295/zh801608001158.pdf>.
Keisuke Furumatsu, et al., "A Role of the Aryl Hydrocarbon Receptor in Attenuation of Colitis," Dig Dis Sci, vol. 56; published online: Mar. 5, 2011, pp. 2532-2544, DOI 10.1007/s10620-011-1643-9.
Brigitta Stockinger, et al, "The Aryl Hydrocarbon Receptor: Multitasking in the Immune System," The Annual Review of Immunology, vol. 33, 2015, pp. 403-432, doi:10.1146/annurev-immunol-032713-120245 (downloaded from www.annualreviews.org).
Veit Rothhammer, et al. "The aryl hydrocarbon receptor: an environmental sensor integrating immune responses in health and disease," Immunology| Nature Reviews, vol. 19, published online: Feb. 4, 2019, pp. 184-197 (www.nature.com/nri).
Emily A. Stevens, et al., "The aryl hydrocarbon receptor: a perspective on potential roles in the immune system," Immunology | The Journal of cells, molecules, systems and technologies, vol. 127, Jan. 6, 2009, pp. 299-311, Blackwell Publishing, doi:10.1111/j.1365-2567.2009.03054.x.
T. L. Vollmer, et al., "A randomized placebo-controlled phase III trial of oral laquinimod for multiple sclerosis," J Neurol, vol. 261, Nov. 12, 2013, pp. 773-783, DOI 10.1007/s00415-014-7264-4.
Geert D'Haens, et al., "A phase II study of laquinimod in Crohn's disease," Inflammatory bowel disease, BMJ Journals, vol. 64, published online: Oct. 3, 2014, pp. 1227-1235, doi:10.1136/gutjnl-2014-307118, downloaded from https://gut.bmj.com/.
Larissa Pernomian, et al., "The Aryl Hydrocarbon Receptor (AHR) as a Potential Target for the Control of Intestinal Inflammation: Insights from an Immune and Bacteria Sensor Receptor," Clinical Reviews in Allergy & Immunology, published online: Apr. 11, 2020, https://doi.org/10.1007/s12016-020-08789-3.
A.K. Azad Khan, et al., "The Disposition and Metabolism of Sulphasalazine (Salicylazosulphapyridine) in Man," Br. J. clin. Pharmac., vol. 13, (1982), pp. 523-528, The Macmillan Press Ltd 1982.

(Continued)

*Primary Examiner* — Rayna Rodriguez

(57) ABSTRACT

The present invention relates to pharmaceutical compounds of Formula (I):

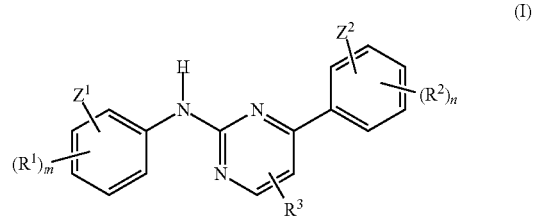

as further described herein, and pharmaceutical compositions containing such compounds, as well as methods of using these compounds to modulate the activity of aryl hydrocarbon receptor (AhR) and to treat conditions comprising inflammation inside the intestinal tract and certain disorders of the central nervous system affected by the gut-brain axis, including IBD, ulcerative colitis, Crohn's disease, Huntington's disease, and multiple sclerosis.

20 Claims, No Drawings

(56) References Cited

OTHER PUBLICATIONS

Johnny Peppers, PhD, et al., "A phase 2, randomized dose-finding study of tapinarof (GSK2894512 cream) for the treatment of atopic dermatitis," American Academy of Dermatology, Inc., vol. 80; No. 1, published online: Jul. 3, 2018, pp. 89-98, https://doi.org/10.1016/j.jaad.2018.06.047.

Robert Bissonnette, MD, et al., "Tapinarof in the treatment of psoriasis: A review of the unique mechanism of action of a novel therapeutic aryl hydrocarbon receptoremodulating agent," American Academy of Dermatology, Inc., vol. 84; No. 4, published online: Nov. 3, 2020, pp. 1059-1067, Published by Elsevier Inc., https://doi.org/10.1016/j.jaad.2020.10.085.

English translation of WO 2021/175,097 from Google Patents.

English translation of WO 2021/185,297 from Google Patents.

USPTO, non-final office action for U.S. Appl. No. 18/433,237, dated Apr. 24, 2024, 7 pages.

Nexys Therapeutics Inc., Response to non-final office action for U.S. Appl. No. 18/433,237, dated Jul. 17, 2024, 20 pages.

Nexys Therapeutics Inc., Amendment under section 35 C.F.R. 35 section 1-312 for U.S. Appl. No. 18/433,237, dated Nov. 4, 2024, 4 pages.

USPTO, Response to Applicant's amendments under Rule 312, dated Nov. 12, 2024, 2 pages.

EPO, Communication pursuant to Rules 161(10 and 162 EPC, EP Appln. No. 23709504.7, dated Sep. 18, 2024, 3 pages.

ARYL HYDROCARBON RECEPTOR AGONISTS AND USES THEREOF

CROSS-REFERENCE TO RELATED APPLICATION

The present application is a continuation application of International Patent Application Serial No. PCT/US2023/012166 filed on Feb. 2, 2023, which claims priority to U.S. provisional patent application No. 63/306,458 filed on Feb. 3, 2022, the disclosure and contents of each of these applications are incorporated herein by reference in its entirety for all purposes. The present application is also related to U.S. application Ser. No. 18/433,237 which was filed together with the present application on Feb. 5, 2024 and which claims the same priority.

FIELD OF THE INVENTION

The field of this invention is compounds, pharmaceutical compositions and methods of making and using them, especially as they are related to compounds and compositions that act as agonists of aryl hydrocarbon receptor (AhR). In particular, it relates to methods of using such agonists for treatment of neurodegenerative diseases and inflammatory disorders, especially those occurring in the intestinal tract or in relationship to the gut-brain axis. Particular conditions for which the compounds, compositions and methods of the invention are suited include ulcerative colitis, Crohn's disease, inflammatory bowel disease (IBD), multiple sclerosis, and Huntington's disease.

BACKGROUND OF THE INVENTION

Aryl hydrocarbon receptor (AhR) was long studied for its role in toxicity of exogenous substances such as TCDD (2,3,7,8-tetrachlorodibenzo-p-dioxin), which binds to AhR and causes it to activate endogenous detoxification mechanisms. However, AhR also recognizes a variety of endogenous ligands, many based on indoles and tryptophan analogs, and the evolutionary conservation, tight regulation, and widespread expression of AhR in the immune system strongly suggested it had important physiological functions. *The Aryl Hydrocarbon Receptor: Multitasking in the Immune System*, B. Stockinger, J et al., *Annu. Rev. Immunol.* 2014, 32:403-32. Its immune modulation effects have been the subject of extensive study, which demonstrated that AhR agonists affect model systems of experimental autoimmune encephalitis (EAE), graft-versus-host disease (GVHD), and mouse models of allergy and transplant tolerance, and also promotes regulatory T-cell proliferation and inflammatory cytokine secretion.

AhR is normally found in the cytosol, bound to actin filaments along with several chaperone proteins in an inactive complex. When a ligand binds to the actin complex, AhR dissociates from actin and translocates into the nucleus of the cell, where it is released from the chaperone complex. AhR then binds to a partner protein, ARNT (aryl hydrocarbon receptor nuclear translocator), forming a heterodimer. The heterodimer binds to a recognition motif, the dioxin response element (DRE), which induces expression of key proteins, including CYP1A1, CYP1A2, CYP1B1, and AhR repressor (AhRR), as well as affecting various adaptive immune system components.

AhR exerts multiple functions in the gut, acting as an essential keeper of the gut barrier. Dietary-derived AhR ligands ensure maintenance of intraepithelial lymphocytes (IELs) (e.g., γδT cells and CD8ααT cells) as well as innate lymphoid cells (ILCs) (e.g., ILC3) and proliferation of colonic crypt stem cells. Moreover, AhR signaling is critically involved in the formation of tertiary lymphoid tissues such as cryptopatches and intestinal lymphoid follicles (ILFs). AhR deficiency leads to loss of ILC3 and IELs, loss of IL-22, disruption of colonic crypt stem cell proliferation, and dysregulation of intestinal bacteria. These studies have shown that AhR plays an essential physiological role in preserving the homeostasis of intestinal barrier functions of the gut when activated by dietary components that act as agonists of AhR.

Agonists of AhR, including VAF347 and laquinimod, have demonstrated promising activity on immunological and neurodegenerative disorders. Laquinimod (TV-5600, previously ABR-215062) is a novel synthetic compound with high oral bioavailability, which was tested as an oral formulation for Crohn's disease (CD), multiple sclerosis (MS), Huntington's disease and lupus nephritis. Preclinical data in various experimental models of colitis and MS suggest that laquinimod has a direct inhibitory effect on antigen presenting cells and T cells, resulting in downregulation of pro-inflammatory cytokines. *A Phase II Study of Laquinimod in Crohn's Disease*, D'Haens G, et al. *Gut* 2015, vol. 64:1227-1235. It failed to meet the Phase 3 clinical trial objectives for treating MS, but demonstrated significant effects on brain atrophy in both relapsing-remitting multiple sclerosis and Huntington's disease patients, which supports the potential of AhR as a target site for treatment of neurodegenerative diseases.

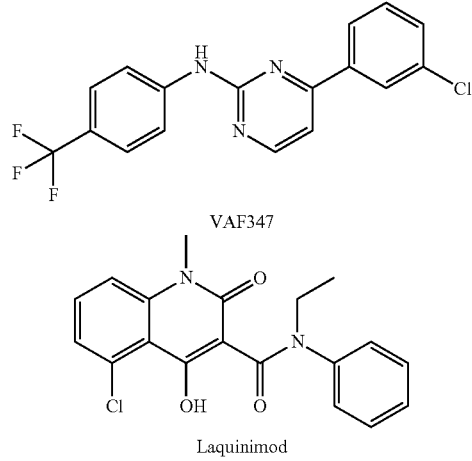

VAF347

Laquinimod

Without being bound by theory, compounds of the invention are believed to be effective for treating inflammatory and/or immune disorders that occur in the lower gastrointestinal (GI) tract by activating AhR in tissues of the lower GI tract. By activating AhR in tissues of the lower GI tract, compounds of the invention may also provide therapeutic effects in certain neuroinflammatory or neurodegenerative diseases through modulation of the gut-brain axis, the bidirectional communication between the GI system and the CNS.

Certain of the compounds of the invention comprise an arylamine group (Ar—$NH_2$), and known compounds having this feature that are used to treat similar conditions in the lower GI tract are sometimes administered as azo compounds of the general formula Ar—N=N—Ar'. Bacteria in the gut reduce the azo linkage to produce aryl amines, e.g., Ar—N=N—Ar'→Ar-NH$_2$+Ar'—NH$_2$. For example, sulfasalazine is used to treat ulcerative colitis and Crohn's disease, acting as an anti-inflammatory in the colon. It contains an azo linkage that gets reduced in the colon by gut bacteria, producing a sulfapyridine compound and 5-ASA as shown below. Sulfasalazine is thus a prodrug: its reduction in the colon releases 5-ASA, which focuses the drug's anti-inflammatory effects in the colon. *Br. J. Clin. Pharmac.* (1982), 13, 523-528.

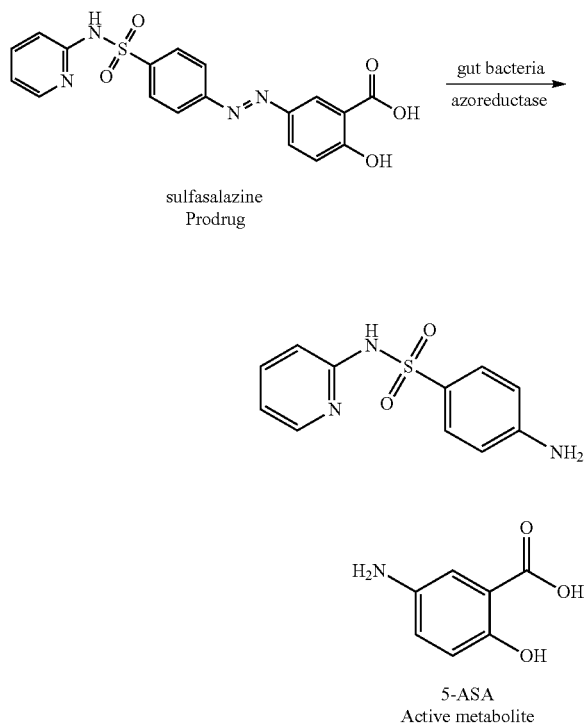

Similarly, some compounds of the invention comprise an azo linkage of the general formula Ar—N=N—Ar', which can be reduced in the colon to produce active AhR agonists that comprise a group of the formula Ar—NH$_2$. These compounds are especially useful for oral administration to treat disorders of the colon or associated with the gut-brain axis. Note that azo compounds can exist as cis and trans isomers: as used herein, unless expressly described as a cis or trans isomer, structural depictions of azo compounds of the invention include both cis and trans isomers as well as mixtures thereof.

While at least one topical AhR agonist (tapinarof) is in development for treatment of psoriasis and atopic dermatitis there remains a need for agonists of AhR useful to treat neurodegenerative and inflammatory disorders, including inflammatory bowel disorder, ulcerative colitis, Crohn's disease, multiple sclerosis, or Huntington's disease. The invention provides such compounds, including some azo compounds that act as prodrugs to target delivery of the active moiety to the lower GI tract.

DISCLOSURE OF THE INVENTION

In one aspect, the present disclosure provides for a heterocyclic compound having a structure according to Formula I:

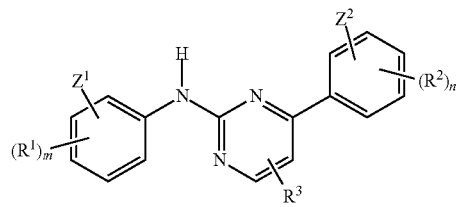

wherein:
one of $Z^1$ and $Z^2$ is selected from —NH$_2$ and —N=N—Ar, and the other of $Z^1$ and $Z^2$ is H,
wherein Ar is selected from phenyl, naphthyl, and

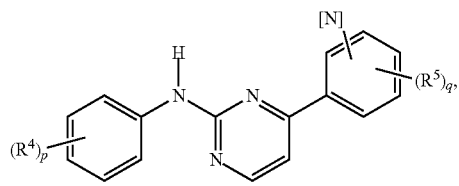

wherein each phenyl and naphthyl is optionally substituted with up to three groups selected from —OR, COOR, C$_{1-4}$ alkyl, C$_{1-4}$haloalkyl, C$_{1-4}$haloalkoxy, —NR$_2$, CN, —PO$_3$R$_2$, —SO$_2$R, —SO$_3$R, and halo;
$R^3$ is selected from H, CN, halo, C$_{1-4}$ alkyl, C$_{1-4}$haloalkyl, and C$_{1-4}$haloalkoxy; each $R^1$ and $R^4$ is independently selected from —OR, COOR, C$_{1-4}$haloalkyl, C$_{1-4}$ haloalkoxy, —NR$_2$, CN, —PO$_3$R$_2$, —SO$_2$R, —SO$_3$R, halo, and C$_{1-4}$ alkyl optionally substituted with one or two groups selected from —OR', COOR', C$_{1-4}$ alkoxy, C$_{1-4}$haloalkoxy, C$_{1-4}$haloalkyl, —CN, and —NR'$_2$;
each $R^2$ and $R^5$ is independently selected from halo, —OR, COOR, C$_{1-4}$haloalkyl, C$_{1-4}$ haloalkoxy, —NR$_2$, CN, —PO$_3$R$_2$, —SO$_2$R, —SO$_3$R, and C$_{1-4}$ alkyl optionally substituted with one or two groups selected from —OR', COOR', C$_{1-4}$ alkoxy, C$_{1-4}$haloalkoxy, C$_{1-4}$haloalkyl, —CN, and —NR'$_2$;
each R is independently selected from H, C$_{1-4}$haloalkyl, and C$_{1-4}$ alkyl optionally substituted with one or two groups selected from —OR', COOR', C$_{1-4}$ alkoxy, C$_{1-4}$haloalkoxy, C$_{1-4}$ haloalkyl, —CN, and —NR'$_2$;
each R' is independently selected from H and C$_{1-3}$ alkyl;
each m, n, p, and q is independently selected from 0, 1 and 2; and
[N] represents the attachment of Ar to N in —N=N—Ar;
or a pharmaceutically acceptable salt thereof.

The invention includes subgenera of this class of compounds as described herein, and preferred embodiments of these compounds include the compounds of Examples 1-58. Compounds of the invention are shown to have agonist activity on AhR. Some of the compounds have an azo linkage, and function as pro-drugs to deliver the active moiety to the lower GI tract, thus providing local delivery for treating conditions in that region of the body.

In another aspect, the invention provides pharmaceutical compositions comprising a compound of the invention as described herein in combination with at least one pharmaceutically acceptable excipient.

In another aspect, the invention provides a method to treat a condition affecting the intestinal tract or modulated through the gut-brain axis, wherein the method comprises administering to a subject in need of such treatment an effective amount of a compound as described herein, or a pharmaceutical composition comprising a compound of the invention. In particular, the methods are useful to treat conditions such as inflammatory bowel disorder, ulcerative colitis, Crohn's disease, multiple sclerosis, and Huntington's disease. Ulcerative colitis and Crohn's disease are believed to modulated by local action of the compounds of the invention in the gut, where they provide anti-inflammatory effects. Multiple sclerosis and Huntington's disease are believed to be modulated through the gut-brain axis, the bidirectional communication between the central nervous system and the enteric nervous system, whereby emotional and cognitive centers of the brain are linked with peripheral intestine functions, including the gut microbiome.

In certain embodiments, the pharmaceutical compositions are prepared for oral administration, and the methods comprise oral administration of the compound or pharmaceutical composition.

The compound described above can be used for any suitable purpose. In some embodiments, the compound described above can be used in therapy, particularly for inflammatory disease of the gastrointestinal tract or the central nervous system such as inflammatory bowel disorder, ulcerative colitis, Crohn's disease, multiple sclerosis, and Huntington's disease.

In still another aspect, the present disclosure provides for a pharmaceutical composition comprising a compound described above admixed with at least one pharmaceutically acceptable carrier or excipient, and optionally at least two pharmaceutically acceptable excipients.

In yet another aspect, the present disclosure provides a method for treating and/or preventing a condition selected from inflammatory bowel disorder, ulcerative colitis, Crohn's disease, multiple sclerosis, and Huntington's disease, which comprises administering to a subject in need thereof an effective amount of a compound described above, or a pharmaceutical composition described above.

In yet another aspect, the present disclosure provides for a use of a compound described above for the manufacture of a medicament.

In another aspect, the invention provides a compound as described herein for use in therapy, particularly for therapeutic use to treat inflammatory bowel disorder, ulcerative colitis, Crohn's disease, multiple sclerosis, or Huntington's disease.

In yet another aspect, the present disclosure provides for a combination for treating and/or preventing inflammatory bowel disorder, ulcerative colitis, Crohn's disease, multiple sclerosis, or Huntington's disease in a subject, which combination comprises an effective amount of a compound described above, or a pharmaceutically acceptable salt thereof, and an effective amount of a second prophylactic or therapeutic agent for treating and/or preventing inflammatory bowel disorder, ulcerative colitis, Crohn's disease, multiple sclerosis, or Huntington's disease in a subject.

In yet another aspect, the present disclosure provides for a method for treating and/or preventing inflammatory bowel disorder, ulcerative colitis, Crohn's disease, multiple sclerosis, or Huntington's disease in a subject, which methods comprises administering to a subject in need thereof an effective amount of the combination described above.

In yet another aspect, the present disclosure provides a method for increasing an activity of an aryl hydrocarbon receptor (AhR) and the associated pathways, in a cell or subject, which methods comprises contacting AhR or a cell or a subject in need thereof with an effective amount of a compound of the invention, or a pharmaceutical composition described above, or a combination described above.

DETAILED DESCRIPTION

General Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, $=O$, $=N-CN$, $=N-OR^a$, $=NR^a$, $-OR^a$, $-NR^a_2$, $-SR^a$, $-SO_2R^a$, $-SO_2NR^a_2$, $-NR^aSO_2R^a$, $-NR^a\text{-}CONR^a_2$, $-NR^aCOOR^a$, $-NR^aCOR^a$, $-CN$, $-COOR^a$, $-CONR^a_2$, $-OOCR^a$, $-COR^a$, and $-NO_2$, wherein each $R^a$ is independently H, C1-C8 alkyl, C2-C8 heteroalkyl, C3-C8 heterocyclyl, C4-C10 heterocyclylalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, $=O$, $=N-CN$, $=N-OR^b$, $=NR^b$, $OR^b$, $NR^b_2$, $SR^b$, $SO_2R^b$, $SO_2NR^b_2$, $NR^bSO_2R^b$, $NR^bCONR^b_2$, $NR^bCO\text{-}OR^b$, $NR^bCOR^b$, $CN$, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclylalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., $-NR^b2$, or $-NR^b-C(O)$ $R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidinyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —$OR^a$, —$NR^a_2$, —$SR^a$, —$SO_2R^a$, —$SO_2NR^a_2$, —$NR^aSO_2R^a$, —$NR^aCONR^a_2$, —$NR^aCOOR^a$, —$NR^aCOR^a$, —CN, —$COOR^a$, —$CONR^a_2$, —$OOCR^a$, —$COR^a$, and —$NO_2$, wherein each $R^a$ is independently H, C1-C8 alkyl, C2-C8 heteroalkyl, C3-C8 heterocyclyl, C4-C10 heterocyclyclalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b$, $NR^bCONR^b_2$, $NR^bCOOR^b$, $NR^bCOR^b$, CN, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclyclalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., —$NR^b2$, or —$NR^b$—C(O) $R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "alkoxy" as used herein refers to a hydrocarbon group connected through an oxygen atom, e.g., —O—Hc, wherein the hydrocarbon portion He may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S—Hc, wherein the hydrocarbon portion He is as described for alkoxy groups. For example, contemplated alkylthio groups include methylthio, ethylthio, isopropylthio, methoxyethylthio, benzylthio, allylthio, and the like.

The term 'amino' as used herein refers to the group —$NH_2$. The term "alkylamino" refers to amino groups where one or both hydrogen atoms are replaced by a hydrocarbon group He as described above, wherein the amino nitrogen "N" can be substituted by one or two He groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group He as described above, wherein the amino nitrogen "N" can be substituted by one or two He groups as set forth for alkoxy groups described above.

The term 'acyl' as used herein refers to a group of the formula —C(=O)-D, where D represents an alkyl, alkenyl, alkynyl, cycloalkyl, aryl, heteroaryl, or heterocycle as described above. Typical examples are groups wherein D is a C1-C10 alkyl, C2-C10 alkenyl or alkynyl, or phenyl, each of which is optionally substituted. In some embodiments, D can be H, Me, Et, isopropyl, propyl, butyl, C1-C4 alkyl substituted with —OH, —OMe, or NH₂, phenyl, halophenyl, alkylphenyl, and the like.

The term "aryloxy" as used herein refers to an aryl group connecting to an oxygen atom, wherein the aryl group may be further substituted. For example, suitable aryloxy groups include phenyloxy, etc. Similarly, the term "arylthio" as used herein refers to an aryl group connecting to a sulfur atom, wherein the aryl group may be further substituted. For example, suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O— wherein one or more hydrogen atoms on the alkyl group have been substituted with a halo group and include, by way of examples, groups such as trifluoromethoxy, and the like.

It should further be recognized that all of the above-defined groups may further be substituted with one or more substituents, which may in turn be substituted with hydroxy, amino, cyano, C1-C4 alkyl, halo, or C1-C4 haloalkyl. For example, a hydrogen atom in an alkyl or aryl can be replaced by an amino, halo or C1-4 haloalkyl or alkyl group.

The term "substituted" as used herein refers to a replacement of a hydrogen atom of the unsubstituted group with a functional group, and particularly contemplated functional groups include nucleophilic groups (e.g., —NH₂, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —NH₃⁺), and halogens (e.g., —F, —Cl), NHCOR, NHCONH₂, OCH₂COOH, OCH₂CONH₂, OCH₂CONHR, NHCH₂COOH, NHCH₂CONH₂, NHSO₂R, OCH₂-heterocycles, PO₃H, SO₃H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment.

For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation as counterion and the like, or when a basic group such as an amine in a compound is protonated or alkylated, causing the compound to have a positive charge and to be associated with an anionic counterion. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The compounds and compositions described herein can be administered to a subject in need of treatment for inflammatory bowel disorder, ulcerative colitis, Crohn's disease, multiple sclerosis, or Huntington's disease. The subject is typically a mammal diagnosed as being in need of treatment for one or more of these diseases or condition, and frequently the subject is a human. The methods comprise administering an effective amount of at least one compound of the invention; optionally the compound may be administered in combination with one or more additional therapeutic agents, particularly therapeutic agents known to be useful for treating the condition or disorder afflicting the particular subject.

The following enumerated embodiments represent certain aspects of the invention.

1. A Compound of Formula (I):

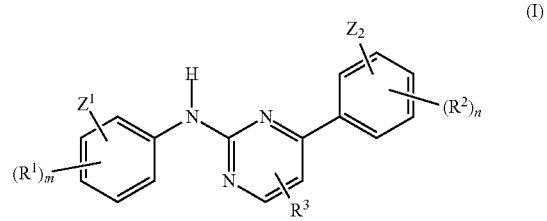

wherein:
one of $Z^1$ and $Z^2$ is selected from —NH$_2$ and —N=N—Ar, and the other of $Z^1$ and $Z^2$ is H,
wherein Ar is selected from phenyl, naphthyl, and

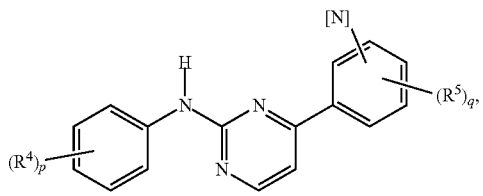

wherein each phenyl and naphthyl is optionally substituted with up to three groups selected from —OR, COOR, $C_{1-4}$ alkyl, $C_{1-4}$haloalkyl, $C_{1-4}$haloalkoxy, —NR$_2$, CN, —PO$_3$R$_2$, —SO$_2$R, —SO$_3$R, and halo;
$R^3$ is selected from H, CN, halo, $C_{1-4}$ alkyl, $C_{1-4}$haloalkyl, and $C_{1-4}$haloalkoxy;
each $R^1$ and $R^4$ is independently selected from —OR, COOR, $C_{1-4}$haloalkyl, $C_{1-4}$ haloalkoxy, —NR$_2$, CN, —PO$_3$R$_2$, —SO$_2$R, —SO$_3$R, halo, and $C_{1-4}$ alkyl optionally substituted with one or two groups selected from —OR', COOR', $C_{1-4}$ alkoxy, $C_{1-4}$haloalkoxy, $C_{1-4}$haloalkyl, —CN, and —NR'$_2$;
each $R^2$ and $R^5$ is independently selected from halo, —OR, COOR, $C_{1-4}$haloalkyl, $C_{1-4}$ haloalkoxy, —NR$_2$, CN, —PO$_3$R$_2$, —SO$_2$R, —SO$_3$R, and $C_{1-4}$ alkyl optionally substituted with one or two groups selected from —OR', COOR', $C_{1-4}$ alkoxy, $C_{1-4}$haloalkoxy, $C_{1-4}$haloalkyl, —CN, and —NR'$_2$;
each R is independently selected from H, $C_{1-4}$haloalkyl, and $C_{1-4}$ alkyl optionally substituted with one or two groups selected from —OR', COOR', $C_{1-4}$ alkoxy, $C_{1-4}$haloalkoxy, $C_{1-4}$ haloalkyl, —CN, and —NR'$_2$;
each R' is independently selected from H and $C_{1-3}$ alkyl;
each m, n, p, and q is independently selected from 0, 1 and 2; and
[N] represents the attachment of Ar to N in —N=N—Ar;
or a pharmaceutically acceptable salt thereof.

In some of these embodiments of special interest, $Z^2$ is NH$_2$. In alternative embodiments of special interest, $Z^2$ is —N=N—Ar. In particular embodiments, these compounds are of the formula:

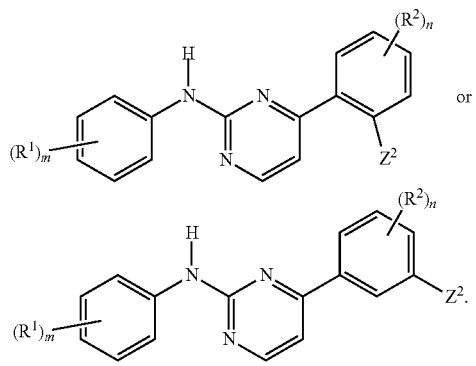

2. The compound of embodiment 1, wherein one of $Z^1$ and $Z^2$ is —NH$_2$, and the other of $Z^1$ and $Z^2$ is H;
or a pharmaceutically acceptable salt thereof.

3. The compound of embodiment 1, wherein one of $Z^1$ and $Z^2$ is —N=N—Ar, and the other of $Z^1$ and $Z^2$ is H;
or a pharmaceutically acceptable salt thereof.

In these embodiments, the azo linkage can be cis or trans or a mixture of cis and trans. These compounds can function as pro-drugs to deliver compounds wherein the azo linkage is reduced, likely by activity of the gut microbiome, to provide compounds in which $Z^1$ or $Z^2$ is NH$_2$ delivered directly to the gut.

4. The compound of embodiment 3, wherein Ar is phenyl or naphthyl, and is optionally substituted with up to three groups selected from —OR, COOR, $C_{1-4}$ alkyl, $C_{1-4}$haloalkyl, $C_{1-4}$ haloalkoxy, —NR$_2$, CN, —PO$_3$R$_2$, —SO$_2$R, —SO$_3$R, and halo;
or a pharmaceutically acceptable salt thereof.

5. The compound of any one of embodiments 1-4, wherein $R^3$ is H;
or a pharmaceutically acceptable salt thereof.

6. The compound of any of embodiments 1-5, wherein p and q are independently selected from 0 and 1;
or a pharmaceutically acceptable salt thereof.

7. The compound of any of the preceding embodiments, wherein the compound is of Formula (IA):

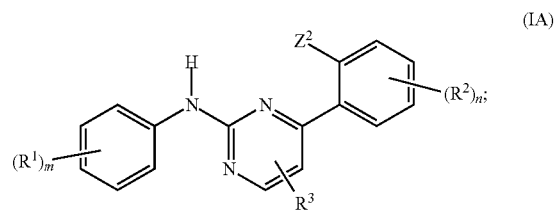

or a pharmaceutically acceptable salt thereof.

8. The compound of embodiment 7, which is a compound of Formula (IB):

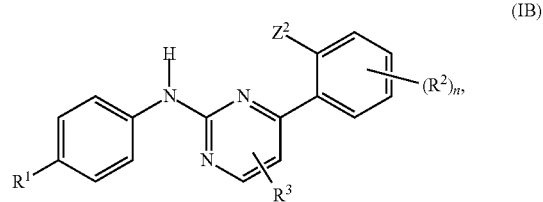

or a pharmaceutically acceptable salt thereof.

9. The compound of embodiment 7 or 8, wherein $Z^2$ is —NH$_2$,
or a pharmaceutically acceptable salt thereof.

10. The compound of embodiment 7 or 8, wherein $Z^2$ is —N=N—Ar;
or a pharmaceutically acceptable salt thereof.

11. The compound of embodiment 9 or 10, wherein n is 0;
or a pharmaceutically acceptable salt thereof.

12. The compound of embodiment 11, wherein $R^1$ is CF$_3$;
or a pharmaceutically acceptable salt thereof.

13. The compound of embodiment 4, wherein Ar is selected from the group consisting of:

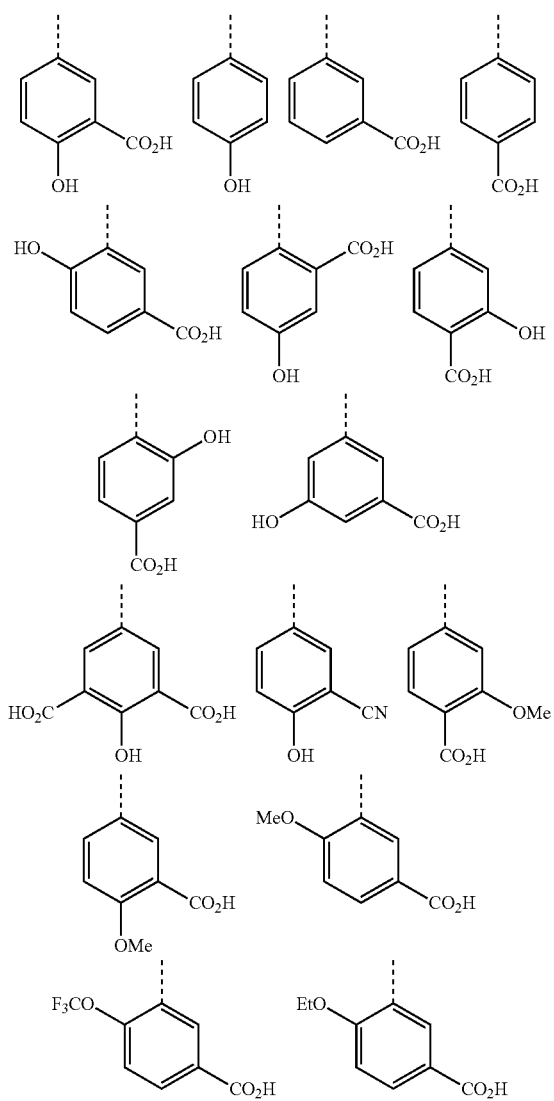

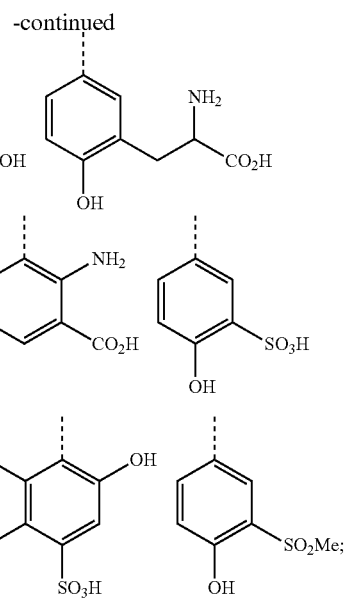

wherein the dashed bond indicates which atom of Ar is attached to N=N;
or a pharmaceutically acceptable salt thereof.

14. The compound of embodiment 13, wherein Ar is

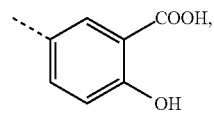

wherein the dashed bond indicates which atom of Ar is attached to N=N;
or a pharmaceutically acceptable salt thereof.

15. The compound of embodiment 1, which is of the Formula (IC):

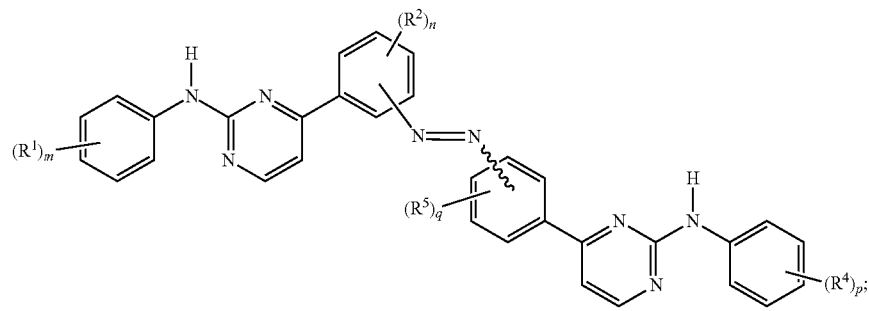

or a pharmaceutically acceptable salt thereof.

16. The compound of embodiment 15, which has the formula:

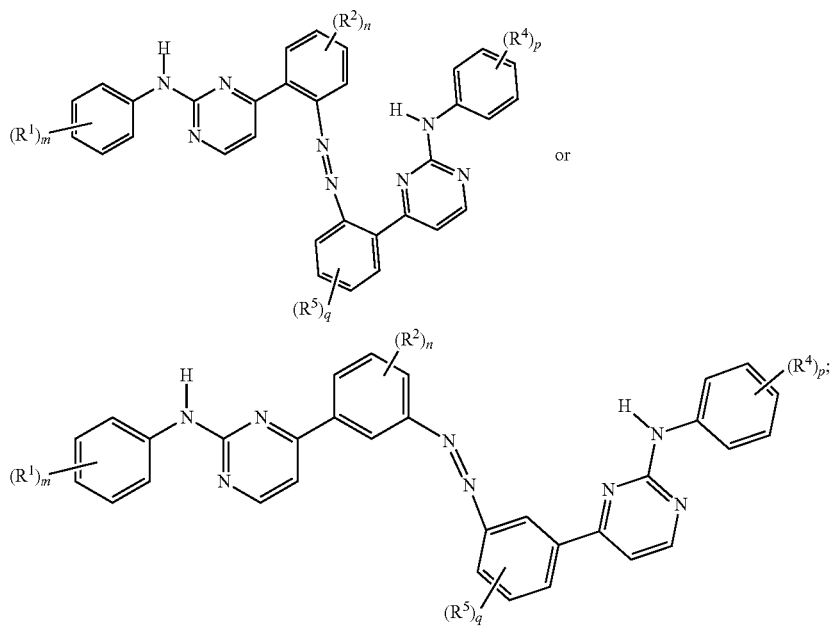
or a pharmaceutically acceptable salt thereof.
17. The compound of embodiment 16, wherein:
   m is the same as p;
   n is the same as q;
   $R^1$ is the same as $R^4$; and
   $R^2$ is the same as $R^5$.
   or a pharmaceutically acceptable salt thereof.
18. The compound of embodiment 16 or 17, which is of the Formula:
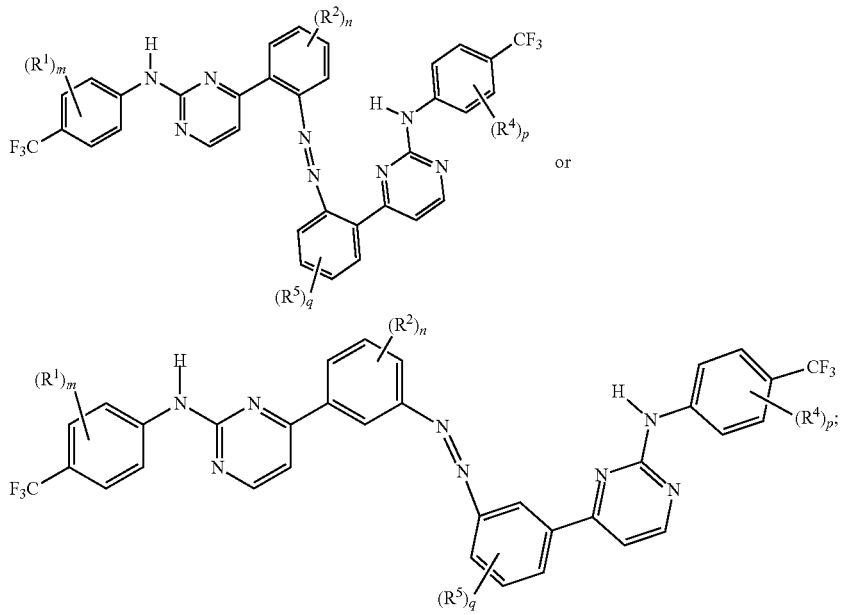
wherein:
   m is 0 or 1;
   p is 0 or 1;
   or a pharmaceutically acceptable salt thereof.

19. The compound of any of the preceding embodiments, which is selected from the compounds in the following Table:

| Example | Structure |
|---|---|
| 1. | 4-CF₃-C₆H₄-NH-[pyrimidin-2-yl]-4-(4-aminophenyl) |
| 2. | 4-CF₃-C₆H₄-NH-[pyrimidin-2-yl]-4-(3-aminophenyl) |
| 3. | 4-CF₃-C₆H₄-NH-[pyrimidin-2-yl]-4-(2-aminophenyl) |
| 4. | 4-CF₃-C₆H₄-NH-[pyrimidin-2-yl]-4-(2-amino-5-chlorophenyl) |
| 5. | 4-CF₃-C₆H₄-NH-[pyrimidin-2-yl]-4-(4-amino-3-chlorophenyl) |
| 6. | 4-CF₃-C₆H₄-NH-[pyrimidin-2-yl]-4-(3-amino-5-chlorophenyl) |
| 7. | 4-CF₃-C₆H₄-NH-[pyrimidin-2-yl]-4-(4-amino-2-carboxyphenyl) |
| 8. | 4-CF₃-C₆H₄-NH-[pyrimidin-2-yl]-4-(4-amino-2-carboxyphenyl) isomer |

| Example | Structure |
|---------|-----------|
| 9. | 3-amino-2-(2-((4-(trifluoromethyl)phenyl)amino)pyrimidin-4-yl)benzoic acid |
| 10. | 2-(4-amino-2-(2-((4-(trifluoromethyl)phenyl)amino)pyrimidin-4-yl)phenyl)acetic acid |
| 11. | 4-amino-2-(2-((4-(trifluoromethyl)phenyl)amino)pyrimidin-4-yl)phenol |
| 12. | 4-amino-3-(2-((4-(trifluoromethyl)phenyl)amino)pyrimidin-4-yl)phenol |
| 13. | 4-amino-3-(2-((4-(trifluoromethyl)phenyl)amino)pyrimidin-4-yl)phenyl methyl sulfone |
| 14 | 5-amino-2-(methylsulfonyl)-3-(2-((4-(trifluoromethyl)phenyl)amino)pyrimidin-4-yl)aniline |
| 15 | 2-(2-((3-(trifluoromethyl)phenyl)amino)pyrimidin-4-yl)aniline |
| 16. | 3-(2-((3-(trifluoromethyl)phenyl)amino)pyrimidin-4-yl)aniline |

-continued
| Example | Structure |
|---|---|
| 17. | 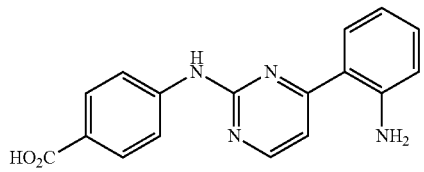 [SMILES: Nc1ccccc1-c1ccnc(Nc2ccc(C(=O)O)cc2)n1] |
| 18. | 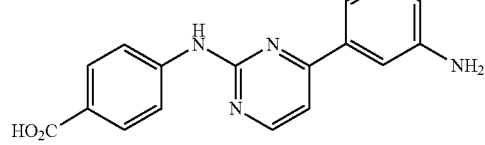 |
| 19 | 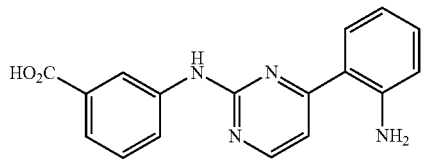 [SMILES: Nc1ccccc1-c1ccnc(Nc2cccc(C(=O)O)c2)n1] |
| 20. | 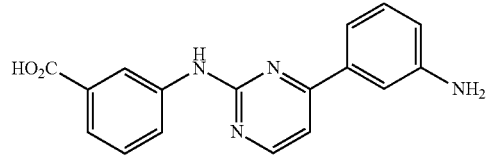 |
| 21 | 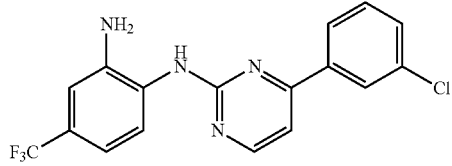 [SMILES: Nc1cc(C(F)(F)F)ccc1Nc1nccc(-c2cccc(Cl)c2)n1] |
| 22. | 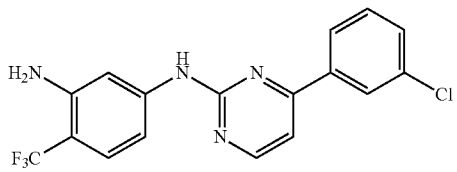 [SMILES: Nc1cc(Nc2nccc(-c3cccc(Cl)c3)n2)ccc1C(F)(F)F] |
| 23. | 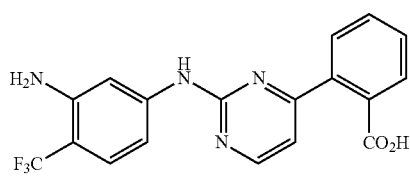 [SMILES: Nc1cc(Nc2nccc(-c3ccccc3C(=O)O)n2)ccc1C(F)(F)F] |
| 24. | 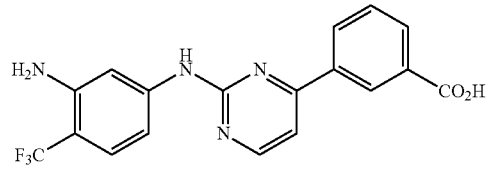 [SMILES: Nc1cc(Nc2nccc(-c3cccc(C(=O)O)c3)n2)ccc1C(F)(F)F] |

| Example | Structure |
|---|---|
| 25. | 4-aminophenyl-NH-[2-pyrimidinyl]-4-(2-hydroxyphenyl) |
| 26. | 3-aminophenyl-NH-[2-pyrimidinyl]-4-(2-hydroxyphenyl) |
| 27. | 4-(trifluoromethyl)phenyl-NH-[2-pyrimidinyl]-4-(3-(2-(3-carboxy-4-hydroxyphenyl)diazenyl)phenyl) |
| 28. | 4-(trifluoromethyl)phenyl-NH-[2-pyrimidinyl]-4-(2-carboxy-5-((3-carboxy-4-hydroxyphenyl)diazenyl)phenyl) |
| 29. | 4-(trifluoromethyl)phenyl-NH-[2-pyrimidinyl]-4-(2-(carboxymethyl)-5-((3-carboxy-4-hydroxyphenyl)diazenyl)phenyl) |
| 30. | bis[4-(trifluoromethyl)phenyl-NH-[2-pyrimidinyl]-4-phenyl] azo-linked (3,3'-azo) |
| 31. | bis[4-(trifluoromethyl)phenyl-NH-[2-pyrimidinyl]-4-phenyl] azo-linked (2,2'-azo) |

| Example | Structure |
|---|---|
| 32. | 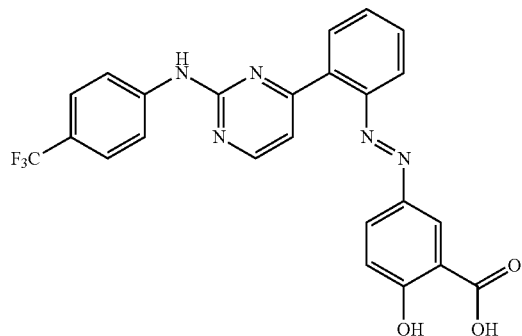 [SMILES: O=C(O)c1cc(/N=N/c2ccccc2-c2ccnc(Nc3ccc(C(F)(F)F)cc3)n2)ccc1O] |
| 33. | 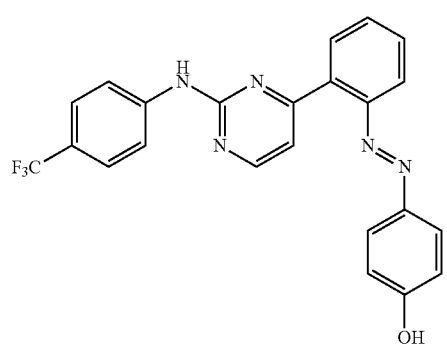 [SMILES: Oc1ccc(/N=N/c2ccccc2-c2ccnc(Nc3ccc(C(F)(F)F)cc3)n2)cc1] |
| 34. | 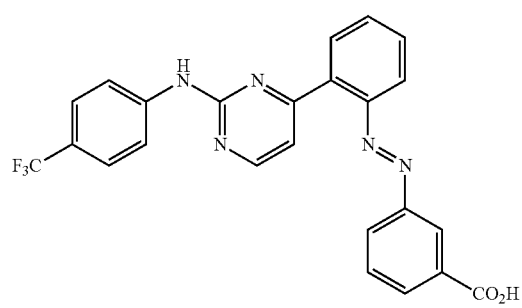 [SMILES: O=C(O)c1cccc(/N=N/c2ccccc2-c2ccnc(Nc3ccc(C(F)(F)F)cc3)n2)c1] |
| 35. | 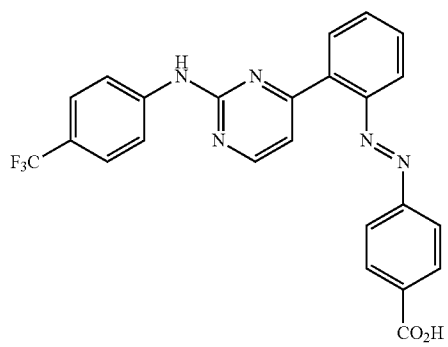 |

-continued
| Example | Structure |
|---------|-----------|
| 36. | 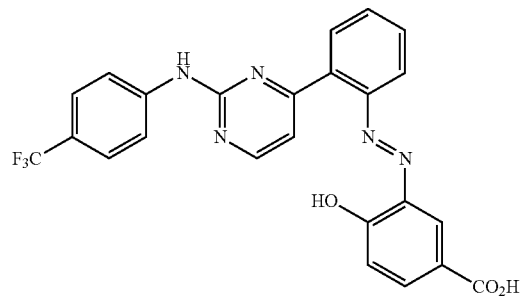 [SMILES: O=C(O)c1ccc(O)c(/N=N/c2ccccc2-c2ccnc(Nc3ccc(C(F)(F)F)cc3)n2)c1] |
| 37. | 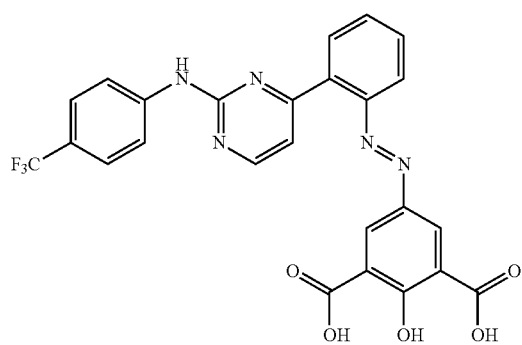 [SMILES: O=C(O)c1cc(/N=N/c2ccccc2-c2ccnc(Nc3ccc(C(F)(F)F)cc3)n2)cc(C(=O)O)c1O] |
| 38. | 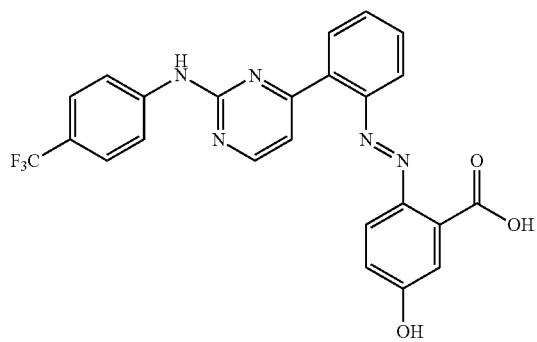 [SMILES: O=C(O)c1cc(O)ccc1/N=N/c1ccccc1-c1ccnc(Nc2ccc(C(F)(F)F)cc2)n1] |
| 39. | 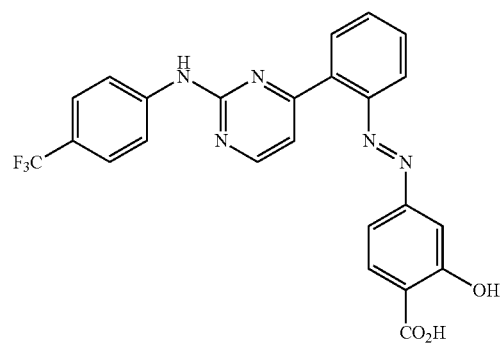 [SMILES: O=C(O)c1ccc(/N=N/c2ccccc2-c2ccnc(Nc3ccc(C(F)(F)F)cc3)n2)cc1O] |

| Example | Structure |
|---|---|
| 40. | 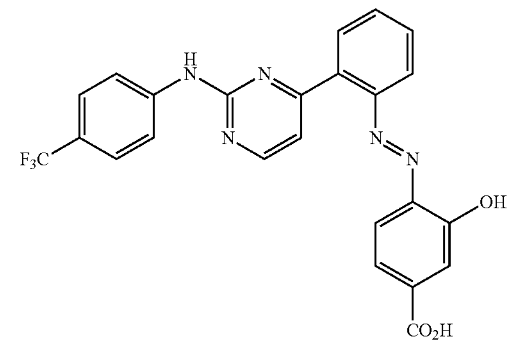 [SMILES: O=C(O)c1ccc(/N=N/c2ccccc2-c2ccnc(Nc3ccc(C(F)(F)F)cc3)n2)c(O)c1] |
| 41. | 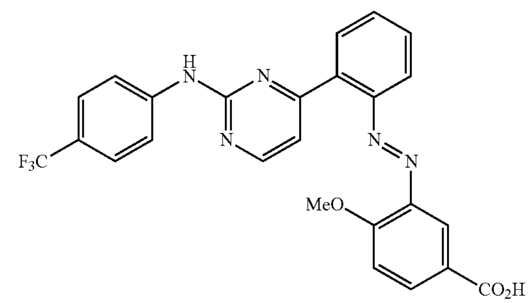 |
| 42. | 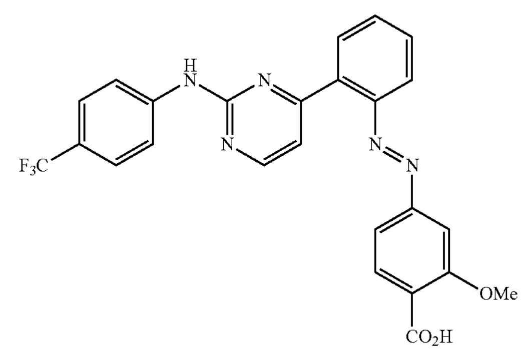 [SMILES: COc1cc(/N=N/c2ccccc2-c2ccnc(Nc3ccc(C(F)(F)F)cc3)n2)ccc1C(=O)O] |
| 43. | 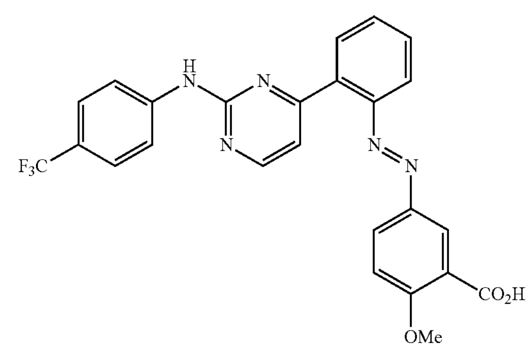 [SMILES: COc1ccc(/N=N/c2ccccc2-c2ccnc(Nc3ccc(C(F)(F)F)cc3)n2)cc1C(=O)O] |

| Example | Structure |
|---|---|
| 44. | 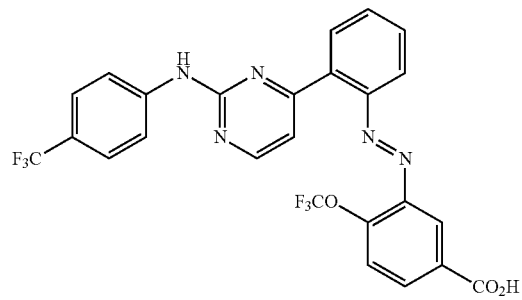 |
| 45. | 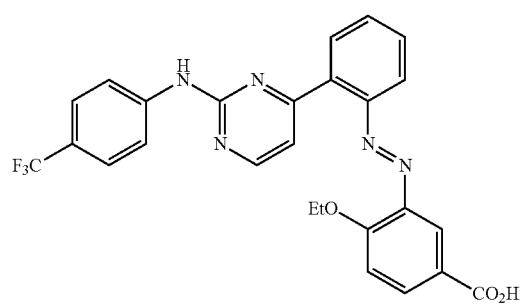 |
| 46. | 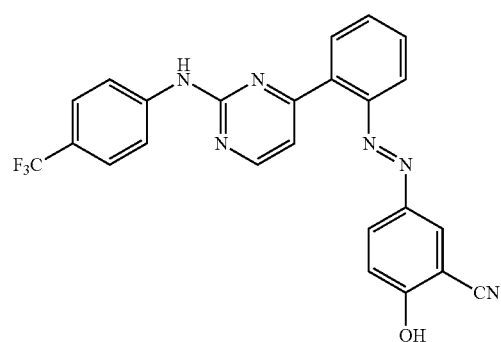 [SMILES: N#Cc1cc(/N=N/c2ccccc2-c2ccnc(Nc3ccc(C(F)(F)F)cc3)n2)ccc1O] |
| 47. | 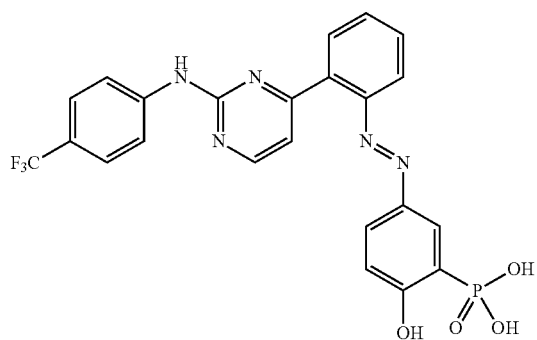 [SMILES: O=P(O)(O)c1cc(/N=N/c2ccccc2-c2ccnc(Nc3ccc(C(F)(F)F)cc3)n2)ccc1O] |

| Example | Structure |
|---|---|
| 48. | 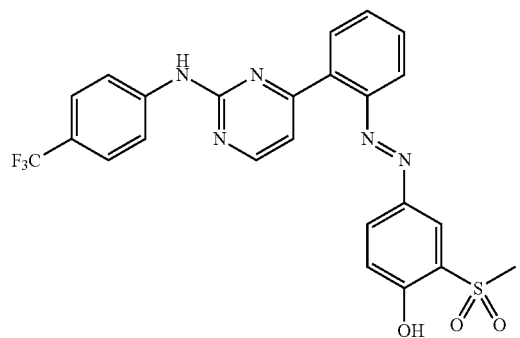 [SMILES: CS(=O)(=O)c1cc(/N=N/c2ccccc2-c2ccnc(Nc3ccc(C(F)(F)F)cc3)n2)ccc1O] |
| 49. | 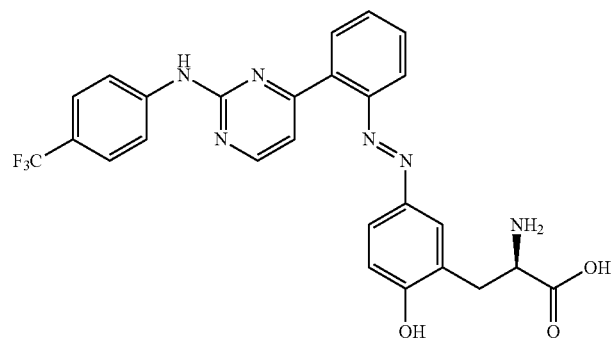 [SMILES: N[C@H](Cc1cc(/N=N/c2ccccc2-c2ccnc(Nc3ccc(C(F)(F)F)cc3)n2)ccc1O)C(=O)O] |
| 50. | 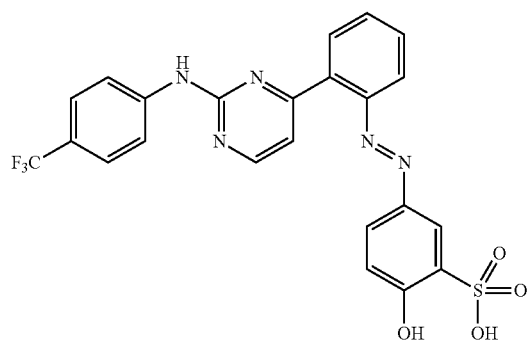 [SMILES: O=S(=O)(O)c1cc(/N=N/c2ccccc2-c2ccnc(Nc3ccc(C(F)(F)F)cc3)n2)ccc1O] |
| 51. | 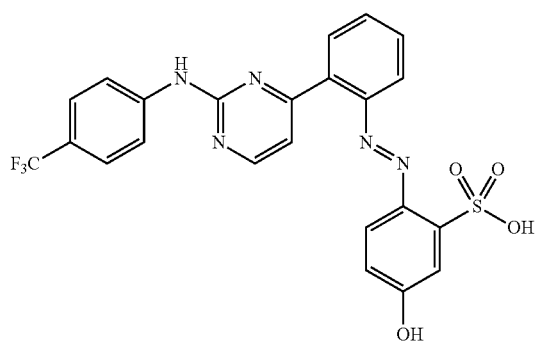 [SMILES: O=S(=O)(O)c1cc(O)ccc1/N=N/c1ccccc1-c1ccnc(Nc2ccc(C(F)(F)F)cc2)n1] |

| Example | Structure |
|---------|-----------|
| 52. | 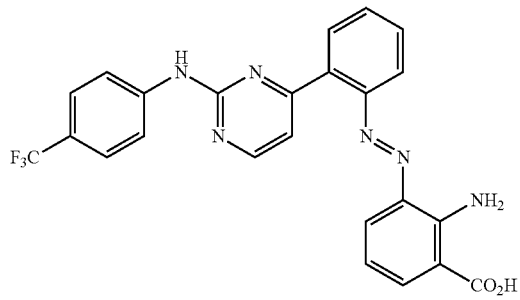 [SMILES: Nc1c(/N=N/c2ccccc2-c2ccnc(Nc3ccc(C(F)(F)F)cc3)n2)cccc1C(=O)O] |
| 53. | 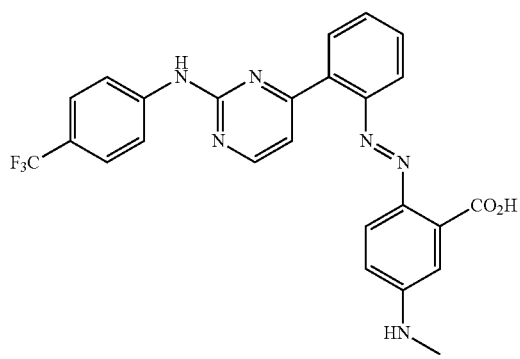 [SMILES: CNc1ccc(/N=N/c2ccccc2-c2ccnc(Nc3ccc(C(F)(F)F)cc3)n2)c(C(=O)O)c1] |
| 54 | 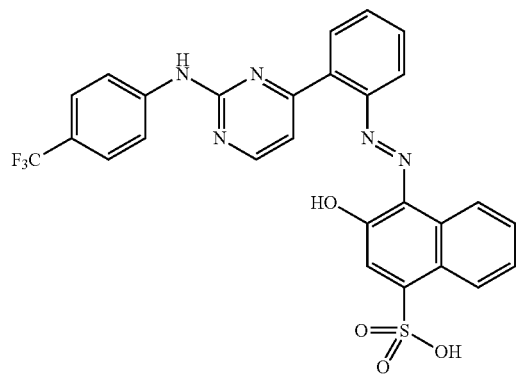 [SMILES: O=S(=O)(O)c1cc(O)c(/N=N/c2ccccc2-c2ccnc(Nc3ccc(C(F)(F)F)cc3)n2)c2ccccc12] |
| 55 | 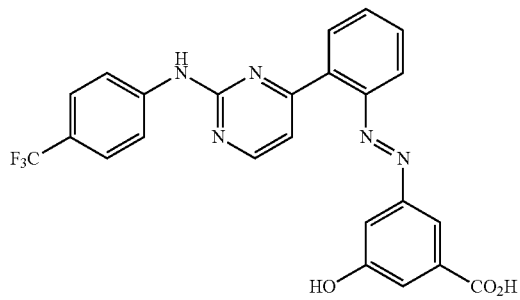 [SMILES: O=C(O)c1cc(O)cc(/N=N/c2ccccc2-c2ccnc(Nc3ccc(C(F)(F)F)cc3)n2)c1] |

-continued
| Example | Structure |
|---|---|
| 56. | 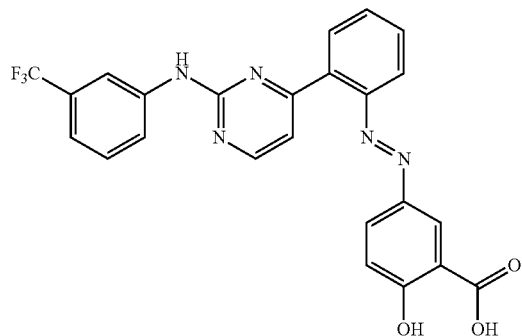 [SMILES: O=C(O)c1cc(/N=N/c2ccccc2-c2ccnc(Nc3cccc(C(F)(F)F)c3)n2)ccc1O] |
| 57. | 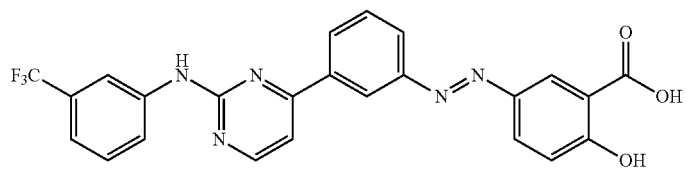 [SMILES: O=C(O)c1cc(/N=N/c2cccc(-c3ccnc(Nc4cccc(C(F)(F)F)c4)n3)c2)ccc1O] |
| 58. | 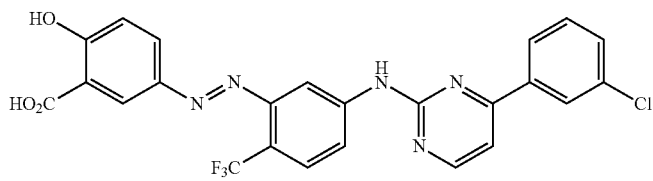 [SMILES: O=C(O)c1cc(/N=N/c2cc(Nc3nccc(-c4cccc(Cl)c4)n3)ccc2C(F)(F)F)ccc1O] |
| 60. | 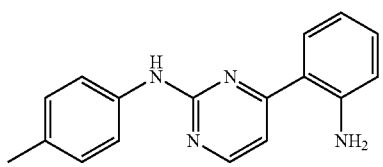 [SMILES: Cc1ccc(Nc2nccc(-c3ccccc3N)n2)cc1] |
| 61. | 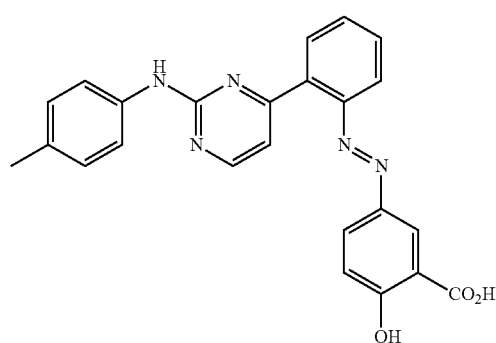 [SMILES: Cc1ccc(Nc2nccc(-c3ccccc3/N=N/c3ccc(O)c(C(=O)O)c3)n2)cc1] |
| 62. | 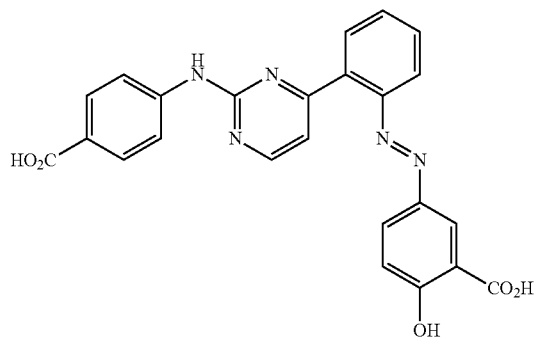 [SMILES: O=C(O)c1ccc(Nc2nccc(-c3ccccc3/N=N/c3ccc(O)c(C(=O)O)c3)n2)cc1] | or a pharmaceutically acceptable salt thereof.

20. A pharmaceutical composition comprising a compound according to any one of embodiments 1-19 admixed with at least one pharmaceutically acceptable excipient. In some of these embodiments, the compound is admixed with two or more pharmaceutically acceptable excipients.

21. A method to treat a condition affecting the intestinal tract or modulated through the gut-brain axis, wherein the method comprises administering to a subject in need of such treatment an effective amount of a compound according to any one of embodiments 1-19.

22. The method of embodiment 21, wherein the condition is inflammatory bowel disorder, ulcerative colitis, Crohn's disease, multiple sclerosis, or Huntington's disease.

23. The method of embodiment 21 or 22, wherein the compound according to any one of claims 1-19 or the pharmaceutical composition of embodiment 20 is administered orally, and is thus prepared or formulated for oral administration.

For all of these embodiments, the compounds of Examples 1-58 and 60-62 are preferred compounds of Formula (I).

24. The method of any one of embodiments 21-23, wherein the method further comprises administering to the subject an additional therapeutic agent useful for treating the condition.

Examples of suitable additional therapeutic agents for us in these methods include prednisone and other steroids, 5-aminosalicylates such as mesalamine, immunomodulators including azathioprine, mercaptopurine, and methotrexate, and certain biologics including infliximab, adalimumab, and certolizumab pegol.

Pharmaceutical Compositions, Combinations, and Other Related Uses

In one aspect, the present disclosure provides for a pharmaceutical composition comprising a compound described above admixed with at least one pharmaceutically acceptable carrier or excipient.

The above-described compounds can be used for any suitable purpose. For example, the present compounds can be used in therapy and/or testing. They are particularly useful for treating conditions mentioned herein.

Any suitable formulation of the compounds described herein can be prepared. See generally, *Remington's Pharmaceutical Sciences*, (2000) Hoover, J. E. editor, 20th edition, Lippincott Williams and Wilkins Publishing Company, Easton, Pa., pages 780-857. A formulation is selected to be suitable for an appropriate route of administration. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are included and are made by conventional methods.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds described herein are generally soluble in organic solvents such as chloroform, dichloromethane, ethyl acetate, ethanol, methanol, isopropanol, acetonitrile, glycerol, N,N-dimethylformamide, N,N-dimethylacetamide, dimethylsulfoxide, etc. In one embodiment, the present invention provides formulations prepared by mixing a compound of the invention with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

In some embodiments, the compounds of the invention are formulated for oral administration.

One of ordinary skill in the art may prepare or modify the formulations within the teachings of the specification and alternatives known to those of ordinary skill to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

Drug Combinations

The methods of the embodiments comprise administering an effective amount of at least one exemplary compound of the present disclosure; optionally the compound may be administered in combination with one or more additional therapeutic agents, particularly therapeutic agents known to be useful for treating inflammatory bowel disorder, ulcerative colitis, Crohn's disease, multiple sclerosis, or Huntington's disease. An additional therapeutic agent is considered to be used in combination with a compound of the invention when timing of administration of the two agents allow them to act concurrently in the subject.

Examples of suitable additional therapeutic agents include prednisone and other steroids, 5-aminosalicylates such as mesalamine, immunomodulators including azathioprine, mercaptopurine, and methotrexate, and certain biologics including infliximab, adalimumab, and certolizumab pegol.

The additional active ingredients may be administered in a separate pharmaceutical composition from at least one exemplary compound of the present disclosure or may be included with at least one exemplary compound of the present disclosure in a single pharmaceutical composition. The additional active ingredients may be administered simultaneously with, prior to, or after administration of at least one exemplary compound of the present disclosure. Selection of suitable additional therapeutic agents and appropriate routes of administration is within the ordinary skill in the art.

Methods of Using the Exemplary Compounds and Pharmaceutical Compositions Thereof To practice the method of the present invention, compounds of the invention and pharmaceutical compositions thereof may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical composition components are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

In some embodiments, the compounds and compositions of the invention are formulated for oral administration. A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

In a preferred embodiment, the compounds of the invention are prepared for oral administration and are administered orally. This is particularly preferred for compounds of the invention wherein $Z^1$ or $Z^2$ is an azo-linked aryl group (—N═N—Ar).

In addition, the compounds having formula I or any of the compounds of Examples 1-58, may be administered alone or in combination with other therapeutic agents, e.g., therapeutic agent useful to treat disorder, ulcerative colitis, Crohn's disease, multiple sclerosis, or Huntington's disease. Combination therapies according to the present invention comprise the administration of at least one exemplary compound of the present disclosure and at least one other pharmaceutically active ingredient. The active ingredient(s) and pharmaceutically active agents may be administered separately or together. Examples of suitable additional pharmaceutically active agents for use with compounds of the invention include prednisone and other steroids, 5-aminosalicylates such as mesalamine, immunomodulators including azathioprine, mercaptopurine, and methotrexate, and certain biologics including infliximab, adalimumab, and certolizumab pegol.

The amounts of the active ingredient(s) and pharmaceutically active agent(s) and the relative timings of administration will be selected in order to achieve the desired combined therapeutic effect.

General Synthetic Procedures

Compounds of the present invention are readily prepared from commonly available compounds using procedures known to those skilled in the art, in view of the examples and Schemes provided herein.

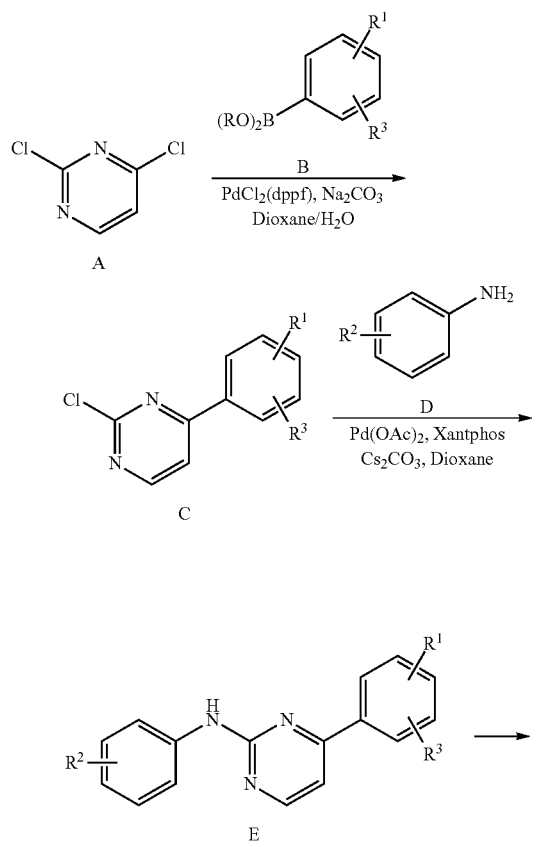

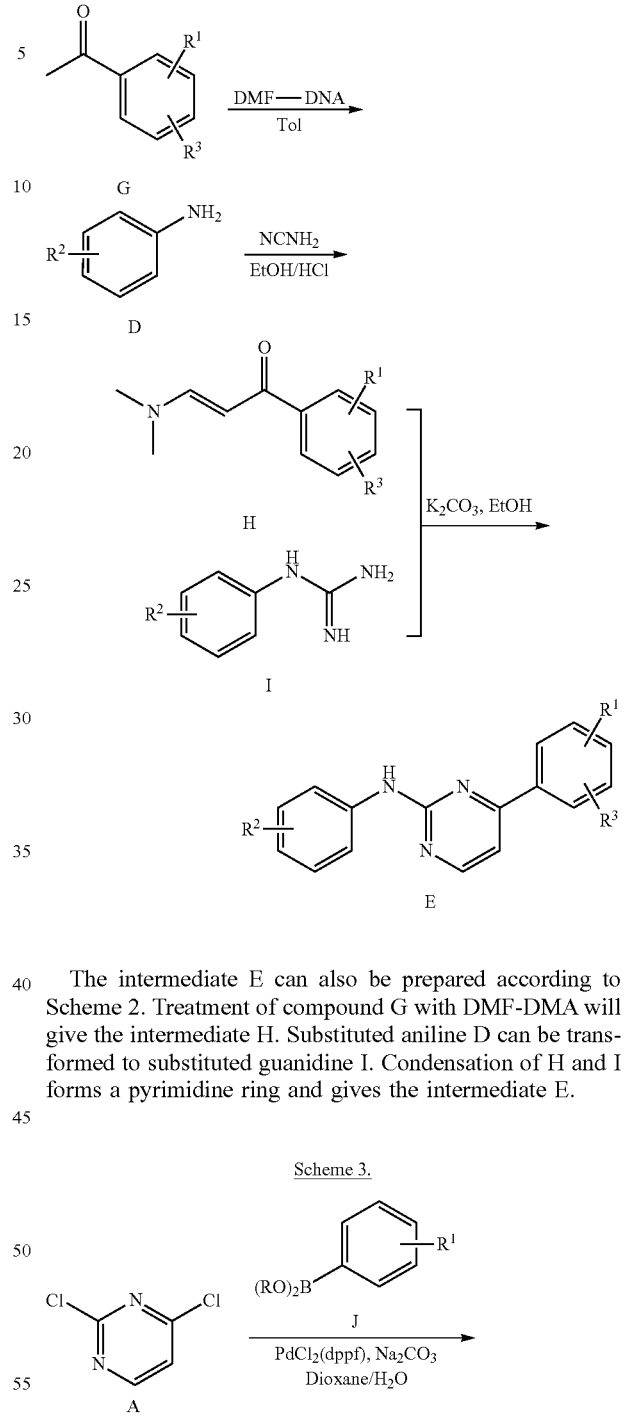

The intermediate E can also be prepared according to Scheme 2. Treatment of compound G with DMF-DMA will give the intermediate H. Substituted aniline D can be transformed to substituted guanidine I. Condensation of H and I forms a pyrimidine ring and gives the intermediate E.

Compounds of Formula (I) with $Z^2$ being $NH_2$ can be prepared according to Scheme 1. Suzuki coupling of compound A and boronic acid/ester B gives the intermediate C. Amination of C with substituted aniline D produced the intermediate E, and $R^3$ was transformed to amine to give the final product F. The $R^3$ group could be $NO_2$, protected $NH_2$ or halogen, which can be transformed to free $NH_2$ by reduction, deprotection or amination, respectively. $R^1$ may be also further transformed to a different substitution group. Depending on the choice of $R^1$ and $R^2$, the product can be a compound of Formula (I) or a precursor to such compounds.

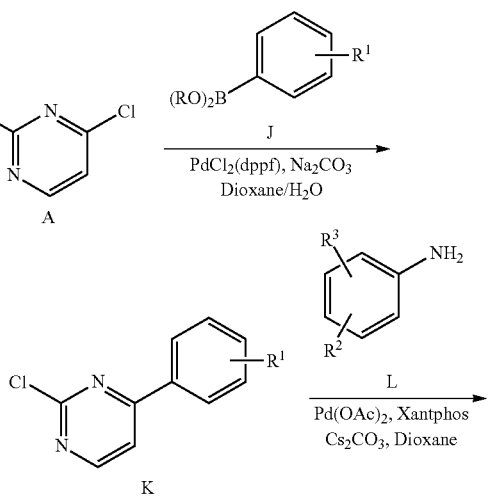

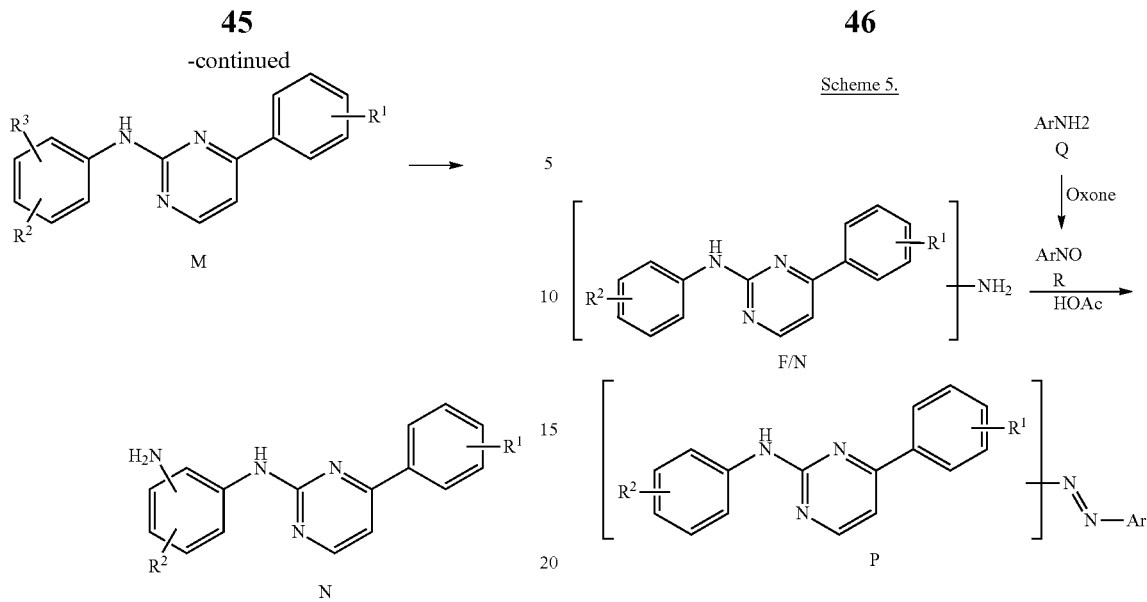

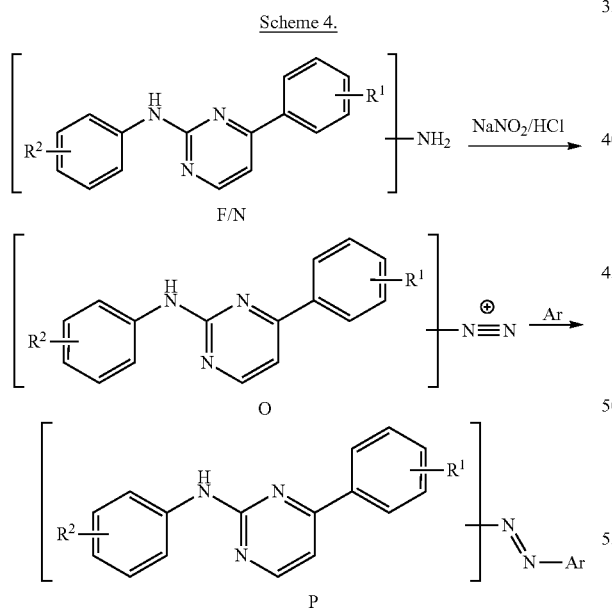

Similar to the route described in Scheme 1, compounds of Formula (I) with $Z^1$ being $NH_2$ can also be prepared according to Scheme 3. In some cases, one of $R^2$ or $R^3$ is $NH_2$, in which case the conversion of compound M to compound N is not necessary.

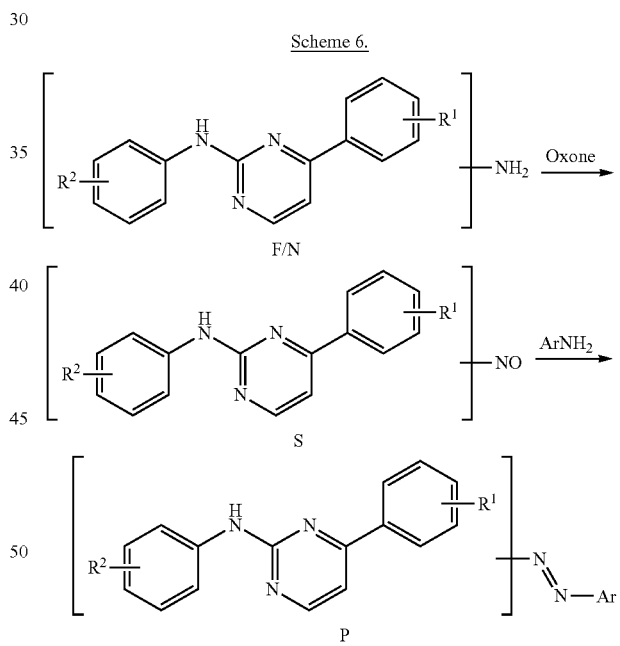

Compounds of Formula (I) with $Z^1$ or $Z^2$ being —N=N—Ar can be prepared according to Scheme 4. The aniline compound F or N from the preceding Schemes can be transformed to diazonium intermediate O in situ by treatment with $NaNO_2$/HCl, which reacts with nucleophilic Ar to form azo compound P. Depending on the choice of $R^1$ and $R^2$, the product can be a compound of Formula (I) or a precursor to such compounds.

The final product P can also be prepared by reacting aniline product F or N with arylnitroso R, which can be prepared by oxidation of arylamine Q with Oxone (Scheme 5). Depending on the choice of $R^1$ and $R^2$, the product can be a compound of Formula (I) or a precursor to such compounds.

The aniline compound F or N can be transformed to nitroso-intermediate S by treatment with Oxone, then further converted to azo compound P by treatment with an aryl amine (Scheme 6). Depending on the choice of $R^1$ and $R^2$, the product can be a compound of Formula (I) or a precursor to such compounds.

Using these and known alternative starting materials, the skilled person can prepare a wide variety of compounds of Formula (I).

EXAMPLES

Abbreviations

Ac acetyl
ACN Acetonitrile
AcOEt/EtOAc Ethyl acetate
AcOH acetic acid
aq. aqueous
Ar aryl
Bn benzyl
Bu butyl (nBu=n-butyl, tBu=tert-butyl)
CDI Carbonyldiimidazole
$CH_3CN$ Acetonitrile
DBU 1,8-Diazabicyclo[5.4.0]-undec-7-ene
$Boc_2O$ di-tert-butyl dicarbonate
BPO Benzoyl peroxide
DCE 1,2-Dichloroethane
DCM Dichloromethane
DIBAL-H Diisobutylaluminum Hydride
DIPEA N-Ethyldiisopropylamine
DMA N,N-dimethylacetamide
DMAP Dimethylaminopyridine
DMF N,N-Dimethylformamide
DMF-DMA N,N-Dimethylformamide dimethyl acetal
DMP Dess-Martin Periodinane
DMSO Dimethylsulfoxide
EI Electrospray ionisation
$Et_2O$ Diethylether
$Et_3N$ Triethylamine
eq Equivalent
Ether Diethylether
EtOAc or EA Ethylacetate
EtOH Ethanol
FA Formic acid
FC Flash Chromatography
h hour(s)
HATU O-(7-Azabenzotriazole-1-yl)-N,N,N'N'—tetramethyluronium hexafluorophosphate
HBTU O-(Benzotriazol-1-yl)-N,N,N',N'-tetramethyluronium hexafluorophosphate
HCl Hydrochloric acid
HMPA Hexamethylphosphoramide
HOBt 1-Hydroxybenzotriazole
HPLC High Performance Liquid Chromatography
$H_2O$ Water
L liter(s)
LC-MS Liquid Chromatography Mass Spectrometry
LiHMDS Lithium bis(trimethylsilyl)amide
mCPBA meta-chloroperoxybenzoic acid
$MgSO_4$ Magnesium Sulfate
Me methyl
MeI Iodomethane
MeOH Methanol
mg milligram
min minute(s)
mL milliliter
MS Mass Spectrometry
MTO methyltrioxorhenium
$NaHCO_3$ Sodium Bicarbonate
$Na_2SO_4$ Sodium Sulfate
NBS N-Bromosuccinimide
NCS N-Chlorosuccinimide
$NH_2OH$ hydroxylamine
Pd/C palladium on charcoal
$Pd(OH)_2$ palladium hydroxide
PE petroleum ether
PG protecting group
Ph phenyl
$Ph_3P$ triphenyl phosphine
Prep Preparative
Rf ratio of fronts
RP reverse phase
Rt Retention time
RT or rt Room temperature
sat. Saturated
$SiO_2$ Silica gel
$SOCl_2$ Thionyl Chloride
TBAF Tetrabutylammonium fluoride
TBDMS t-Butyldimethylsilyl
TEA Triethylamine
TFA Trifluoroacetic acid
TFAA Trifluoroacetic anhydride
TfOH Triflic acid
THF Tetrahydrofuran
TLC Thin Layer Chromatography
TsCl toluene sulfonyl chloride Example 1: 4-(4-aminophenyl)-N-(4-(trifluoromethyl)phenyl)pyrimidin-2-amine

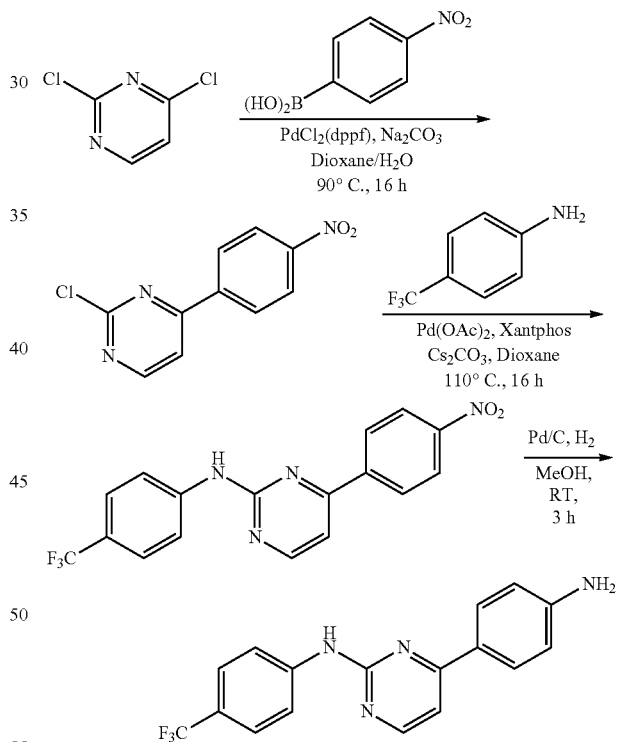

Step 1: 2-chloro-4-(4-nitrophenyl)pyrimidine

A mixture of (4-nitrophenyl)boronic acid (2.0 g, 11.98 mmol, 1.0 eq), 2,4-dichloropyrimidine (1.78 g, 11.98 mmol, 1.0 eq), $Na_2CO_3$ (2.54 g, 23.96 mmol, 2.0 eq) and $PdCl_2$(dppf) (854 mg, 1.2 mmol, 0.1 eq) in dioxane/$H_2O$ (40 mL/4 mL) was stirred at 90° C. for 16 h under Ar. The reaction was monitored by LC-MS. The mixture was diluted with DCM/$H_2O$, and the organic phase was separated, dried over $Na_2SO_4$, filtered and concentrated. The residue was purified by flash chromatography on silica gel (eluent: PE/EA=4:1) to give the title compound (1.7 g, 60%) as a yellow solid. LC-MS: [M+H]⁺ (m/z)=236.1.

Step 2: 4-(4-nitrophenyl)-N-(4-(trifluoromethyl)phenyl)pyrimidin-2-amine

A mixture of 2-chloro-4-(4-nitrophenyl)pyrimidine (200 mg, 0.85 mmol, 1.0 eq), 4-(trifluoromethyl)aniline (150 mg, 0.93 mmol, 1.1 eq), Pd(OAc)$_2$ (19 mg, 0.085 mmol, 0.1 mmol), Xantphos (49 mg, 0.085 mmol, 0.1 eq) and Cs$_2$CO$_3$ (552 mg, 1.7 mmol, 2.0 eq) in dioxane (3.0 mL) was stirred at 110° C. for 16 h under Ar. The reaction was monitored by LC-MS. The mixture was partitioned between DCM/water. The organic phase was separated, dried over Na$_2$SO$_4$, filtered and concentrated to give the title compound, which was used directly in the next step without further purification. LC-MS: [M−H]⁻ (m/z)=359.1.

Step 3: 4-(4-aminophenyl)-N-(4-(trifluoromethyl)phenyl)pyrimidin-2-amine

A mixture of 4-(4-nitrophenyl)-N-(4-(trifluoromethyl)phenyl)pyrimidin-2-amine (300 mg, 0.83 mmol, 1.0 eq) and Pd/C (40 mg) in MeOH (20 mL) was stirred under hydrogen at RT for 3 h. The reaction was monitored by LC-MS. The mixture was filtered, and the filtrate was purified by prep-HPLC (mobile phase: CH$_3$CN/H$_2$O/0.1% NH$_4$HCO$_3$) to give the title compound (102.1 mg, 50%) as a white solid. LC-MS: [M+H]⁺ (m/z)=331.2; ¹H NMR (400 MHz, CDCl$_3$) δ 8.40 (d, J=5.2 Hz, 1H), 7.93 (d, J=8.4 Hz, 2H), 7.83 (d, J=8.4 Hz, 2H), 7.59 (d, J=8.4 Hz, 2H), 7.38 (s, 1H), 7.13 (d, J=5.2 Hz, 1H), 6.77 (d, J=8.8 Hz, 2H), 4.00 (s, 2H).

Example 2: 4-(3-aminophenyl)-N-(4-(trifluoromethyl)phenyl)pyrimidin-2-amine

Step 1: 2-chloro-4-(3-nitrophenyl)pyrimidine

A mixture of (3-nitrophenyl)boronic acid (2.0 g, 12.0 mmol, 1.0 eq), 2,4-dichloropyrimidine (1.78 g, 12.0 mmol, 1.0 eq), Pd(dppf)Cl$_2$ (854 mg, 1.2 mmol, 0.1 eq) and Na$_2$CO$_3$ (2.54 g, 24.0 mmol, 2.0 eq) in dioxane/H$_2$O (20 mL/4.0 mL) was stirred at 100° C. overnight under Ar. The reaction was monitored by LC-MS. The mixture was filtered, and the filtrate was concentrated and purified by flash chromatography on silica gel (eluent: PE/EA=5:1) to give the title compound (1.3 g, 46% yield) as a yellow oil. LC-MS: [M+H]⁺ (m/z)=236.

Step 2: 4-(3-nitrophenyl)-N-(4-(trifluoromethyl)phenyl)pyrimidin-2-amine

A mixture of 2-chloro-4-(3-nitrophenyl)pyrimidine (200 mg, 0.85 mmol, 1.0 eq), 4-(trifluoromethyl)aniline (150 mg, 0.93 mmol, 1.1 eq), Pd(OAc)$_2$ (38 mg, 0.17 mmol, 0.2 eq) and Cs$_2$CO$_3$ (552 mg, 1.7 mmol, 2.0 eq) in dioxane (2.0 mL) was stirred at 110° C. overnight under Ar. The reaction was monitored by LC-MS. The mixture was filtered, and the filtrate was concentrated and purified by flash chromatography on silica gel (eluent: PE/EA=5:1) to give the title compound (200 mg, 65% yield) as a yellow oil. LC-MS: [M+H]⁺ (m/z)=361.

Step 3: 4-(3-aminophenyl)-N-(4-(trifluoromethyl)phenyl)pyrimidin-2-amine

To a solution of 4-(3-nitrophenyl)-N-(4-(trifluoromethyl)phenyl)pyrimidin-2-amine (200 mg, 0.55 mmol, 1.0 eq) in MeOH (5.0 mL) was added Pd/C (10 mg). The mixture was stirred at RT for 2 h under H$_2$. The reaction was monitored by LC-MS until completion. The mixture was filtered and the filtrate was concentrated. The residue was purified by Prep-HPLC (mobile phase: CH$_3$CN/H$_2$O/0.1% FA), and freeze-dried to give the title compound (37.87 mg, 20% yield) as a white solid. LC-MS: [M+H]⁺ (m/z)=331.1; ¹H NMR (400 MHz, CDCl$_3$) δ 8.50 (d, J=4.0 Hz, 1H), 7.84 (d, J=8.4 Hz, 2H), 7.60 (d, J=8.8 Hz, 2H), 7.43-7.10 (m, 2H), 7.35 (s, 1H), 7.30 (t, J=8.0 Hz, 1H), 7.19 (d, J=5.6 Hz, 1H), 6.86-6.83 (m, 1H), 3.83 (s, 2H).

Example 3: 4-(2-aminophenyl)-N-(4-(trifluoromethyl)phenyl)pyrimidin-2-amine

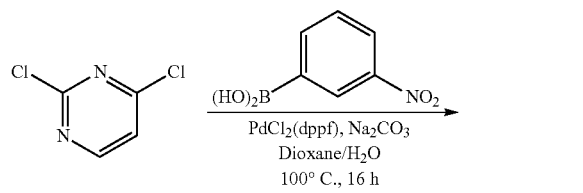

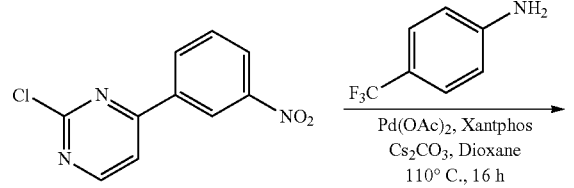

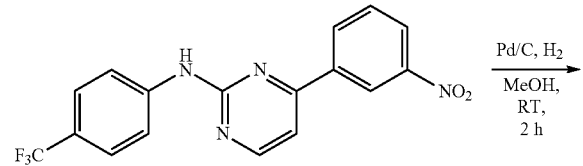

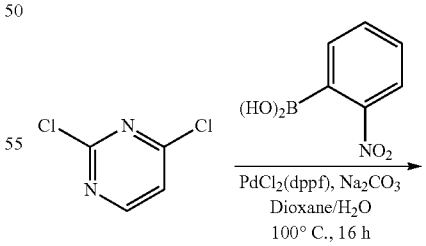

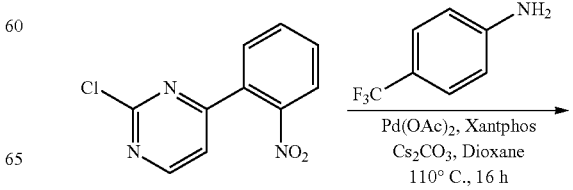

51

-continued

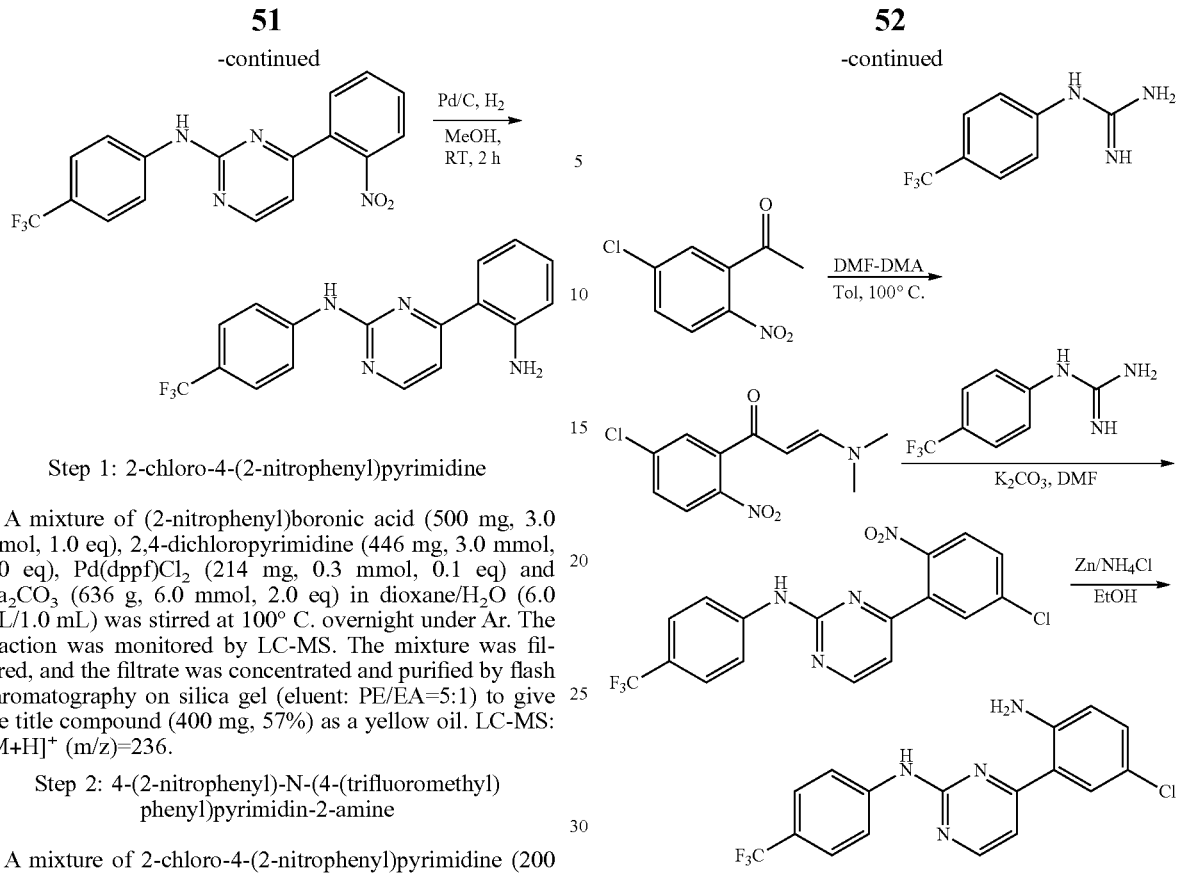

Step 1: 2-chloro-4-(2-nitrophenyl)pyrimidine

A mixture of (2-nitrophenyl)boronic acid (500 mg, 3.0 mmol, 1.0 eq), 2,4-dichloropyrimidine (446 mg, 3.0 mmol, 1.0 eq), Pd(dppf)Cl$_2$ (214 mg, 0.3 mmol, 0.1 eq) and Na$_2$CO$_3$ (636 g, 6.0 mmol, 2.0 eq) in dioxane/H$_2$O (6.0 mL/1.0 mL) was stirred at 100° C. overnight under Ar. The reaction was monitored by LC-MS. The mixture was filtered, and the filtrate was concentrated and purified by flash chromatography on silica gel (eluent: PE/EA=5:1) to give the title compound (400 mg, 57%) as a yellow oil. LC-MS: [M+H]$^+$ (m/z)=236.

Step 2: 4-(2-nitrophenyl)-N-(4-(trifluoromethyl) phenyl)pyrimidin-2-amine

A mixture of 2-chloro-4-(2-nitrophenyl)pyrimidine (200 mg, 0.85 mmol, 1.0 eq), 4-(trifluoromethyl)aniline (150 mg, 0.93 mmol, 1.1 eq), Pd(OAc)$_2$ (38 mg, 0.17 mmol, 0.2 eq) and Cs$_2$CO$_3$ (552 mg, 1.7 mmol, 2.0 eq) in dioxane (2.0 mL) was stirred at 110° C. overnight under Ar. The reaction was monitored by LC-MS. The mixture was filtered, and the filtrate was concentrated. The residue was purified by flash chromatography on silica gel (eluent: PE/EA=5:1) to give the title compound (200 mg, 65%) as a yellow oil. LC-MS: [M+H]$^+$ (m/z)=361.

Step 3: 4-(2-aminophenyl)-N-(4-(trifluoromethyl) phenyl)pyrimidin-2-amine

To a solution of 4-(2-nitrophenyl)-N-(4-(trifluoromethyl) phenyl)pyrimidin-2-amine (200 mg, 0.55 mmol, 1.0 eq) in MeOH (5.0 mL) was added Pd/C (10 mg). The mixture was stirred at RT for 2 h under H$_2$. The reaction was monitored by LC-MS. The mixture was filtered, and the filtrate was concentrated. The residue was purified by prep-HPLC (mobile phase: CH$_3$CN/H$_2$O/0.1% FA) to give the title compound (44 mg, 24%) as a white solid. LC-MS: [M+H]$^+$ (m/z)=331.1; $^1$H NMR (400 MHz, DMSO-d6) δ 10.09 (s, 1H), 8.51 (d, J=5.2 Hz, 1H), 7.98 (d, J=8.8 Hz, 2H), 7.72 (dd, J=8.0, 1.2 Hz, 1H), 7.66 (d, J=8.8 Hz, 2H), 7.36 (d, J=6.0 Hz, 1H), 7.20-7.15 (m, 1H), 7.03 (br s, 2H), 6.81 (dd, J=8.0, 0.8 Hz, 1H), 6.63-6.58 (m, 1H).

Example 4: 4-(2-amino-5-chlorophenyl)-N-(4-(trifluoromethyl)phenyl)pyrimidin-2-amine

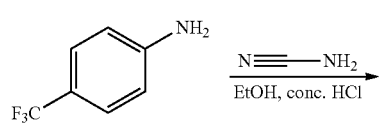

52

-continued

Step 1: 1-(4-(trifluoromethyl)phenyl)guanidine

To a solution of 4-(trifluoromethyl)aniline (5 g, 31 mmol, 1.0 eq) in EtOH (20 mL) was added conc. HCl (2.6 mL, 1.0 eq). The mixture was heated to 85° C., and cyanamide (1.56 g, 37.2 mmol, 1.2 eq) was added. Heating was continued for 16 h before the reaction solution was cooled down to 60° C., and then 1.55 M aq. Na$_2$CO$_3$ (10 mL) was added. After cooling to RT, the mixture was filtered and washed with EtOH (10 mL). The filtrate was concentrated under reduced pressure, and the residue was purified by crystallization (solvent PE/EA=1:1) to give the title compound (1.5 g, 24%) as a white solid. LC-MS: [M+H]$^+$ (m/z)=204.

Step 2: (E)-1-(5-chloro-2-nitrophenyl)-3-(dimethylamino)prop-2-en-1-one

A mixture of 1-(5-chloro-2-nitrophenyl)ethan-1-one (200 mg, 1.0 mmol, 1.0 eq) and DMF-DMA (0.5 mL) in toluene (3.0 mL) was stirred at 100° C. for 16 h under Ar. The reaction was monitored by LC-MS. The mixture was concentrated to give the title compound, which was used directly to next step without further purification. LC-MS: [M+H]$^+$ (m/z)=255.1.

Step 3: 4-(5-chloro-2-nitrophenyl)-N-(4-(trifluoromethyl)phenyl)pyrimidin-2-amine A mixture of (E)-1-(5-chloro-2-nitrophenyl)-3-(dimethylamino)prop-2-en-1-one (240 mg, 0.95 mmol, 1.0 eq), 1-(4-(trifluoromethyl)phenyl)guanidine (288 mg, 1.42 mmol, 1.5 eq) and K$_2$CO$_3$ (326 mg, 2.36 mmol, 2.5 eq) in DMF (3.0 mL) was stirred at 120° C. for 16 h under Ar. The reaction was monitored by LC-MS. The mixture was partitioned between EA/water.

The organic phase was separated, dried over Na$_2$SO$_4$, filtered and concentrated. The residue was purified by prep-TLC (PE/EA=2:1) to give the title compound (40 mg, 10%) as a white solid.

LC-MS: [M−H]$^-$ (m/z)=393.2.

Step 4: 4-(2-amino-5-chlorophenyl)-N-(4-(trifluoromethyl)phenyl)pyrimidin-2-amine A mixture of 4-(5-chloro-2-nitrophenyl)-N-(4-(trifluoromethyl)phenyl)pyrimidin-2-amine (40 mg, 0.1 mmol, 1.0 eq) and Zn (33 mg, 0.5 mmol, 5.0 eq) in EtOH/NH$_4$Cl (5.0 mL/1.0 mL) was stirred at RT for 16 h. The mixture was monitored by LC-MS. The mixture was purified by prep-HPLC (mobile phase: CH$_3$CN/H$_2$O/0.1% NH$_4$HCO$_3$) to give the title compound (21.5 mg, 58%) as a white solid. LC-MS: [M+H]$^+$ (m/z)=365.0; $^1$H NMR (400 MHz, CD$_3$OD) δ 8.49 (d, J=5.6 Hz, 1H), 7.90 (d, J=8.8 Hz, 2H), 7.66 (d, J=2.4 Hz, 1H), 7.58 (d, J=8.8 Hz, 2H), 7.24 (d, J=5.6 Hz, 1H), 7.14 (dd, J=8.8, 2.4 Hz, 1H), 6.79 (d, J=8.8 Hz, 1H).

Example 5: 4-(4-amino-3-chlorophenyl)-N-(4-(trifluoromethyl)phenyl)pyrimidin-2-amine

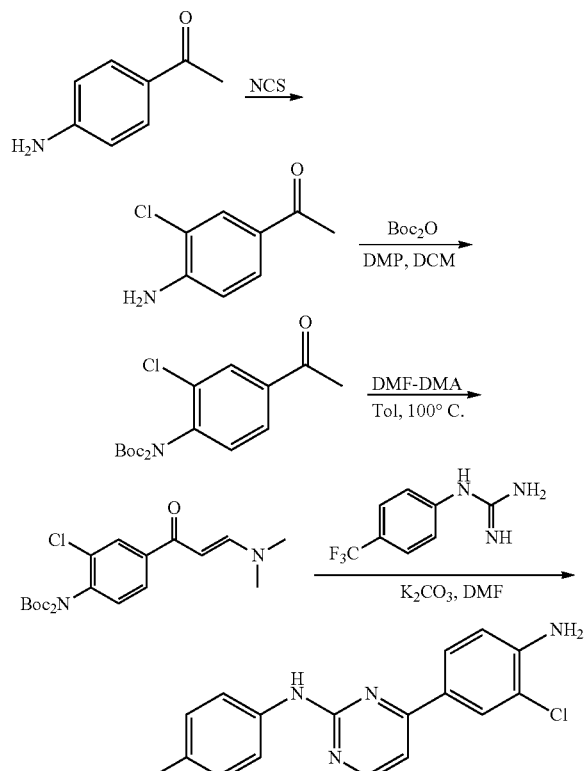

Step 1: 1-(4-amino-3-chlorophenyl)ethan-1-one

A mixture of 1-(aminophenyl)ethan-1-one (1.0 g, 7.4 mmol, 1.0 eq) and NCS (1.08 g, 8.1 mmol, 1.1 eq) in 2-propanol (20.0 mL) was stirred at 60° C. for 16 h under Ar. The reaction was monitored by LC-MS. The mixture was partitioned between DCM/water. The organic phase was separate, dried over Na$_2$SO$_4$, filtered and concentrated to dryness. The residue was purified by flash chromatography on silica gel (PE/EA=6:1) to give the title compound (1.0 g, 81%) as a yellow solid. LC-MS: [M+H]$^+$ (m/z)=170.2.

Step 2: tert-butyl (4-acetyl-2-chlorophenyl)(tert-butoxycarbonyl)carbamate

A mixture of 1-(4-amino-3-chlorophenyl)ethan-1-one (500 mg, 2.96 mmol, 1.0 eq) and DMAP (36 mg, 0.30 mmol, 0.1 eq) in DCM (10 mL) was added (Boc)$_2$O (709 mg, 3.25 mmol, 1.1 eq). The mixture was stirred at RT for 1 h under Ar. The mixture was monitored by TLC. The crude was purified by FC on silica gel (PE/EA=10:1) to give the title compound (740 mg, 76%) as a white solid. LC-MS: [M+H]$^+$ (m/z)=214.1 (-Boc-tBu fragment).

Step 3: tert-butyl (E)-(tert-butoxycarbonyl)(2-chloro-4-(3-(dimethylamino)acryloyl)phenyl)-carbamate A mixture of tert-butyl (4-acetyl-2-chlorophenyl)(tert-butoxycarbonyl)carbamate (400 mg, 1.08 mmol, 1.0 eq) and DMF-DMA (2.0 mL) in Tol (10 mL) was stirred at 100° C. for 16 h under Ar. The reaction was monitored by LC-MS. The mixture was concentrated to dryness and used directly in the next step without further purification. LC-MS: [M+H]$^+$ (m/z)=425.1.

Step 4: 4-(4-amino-3-chlorophenyl)-N-(4-(trifluoromethyl)phenyl)pyrimidin-2-amine A mixture of tert-butyl (E)-(tert-butoxycarbonyl)(2-chloro-4-(3-(dimethylamino)acryloyl)phenyl)-carbamate (350 mg, 0.825 mmol, 1.0 eq), 1-(4-(trifluoromethyl)phenyl)guanidine (251 mg, 1.24 mmol, 1.5 eq) and K$_2$CO$_3$ (285 mg, 2.06 mmol, 2.5 eq) in DMF (5.0 mL) was stirred at 120° C. for 16 h under Ar. The reaction was monitored by LC-MS. The mixture was partitioned between EA/water. The organic phase was dried over Na$_2$SO$_4$, filtered, and concentrated. The residue was purified by prep-HPLC (mobile phase: CH$_3$CN/H$_2$O/0.1% NH$_4$HCO$_3$) to give the title compound (22.5 mg, 7% over 2 steps) as a white solid. LC-MS: [M+H]$^+$ (m/z)=365.0; $^1$H NMR (400 MHz, CD$_3$OD) δ 8.40 (d, J=5.6 Hz, 1H), 8.11 (d, J=2.0 Hz, 1H), 7.96 (d, J=8.4 Hz, 2H), 7.88 (dd, J=8.8, 2.0 Hz, 1H), 7.58 (d, J=8.8 Hz, 2H), 7.24 (d, J=5.2 Hz, 1H), 6.90 (d, J=8.4 Hz, 1H).

Example 6: 4-(3-amino-5-chlorophenyl)-N-(4-(trifluoromethyl)phenyl)pyrimidin-2-amine

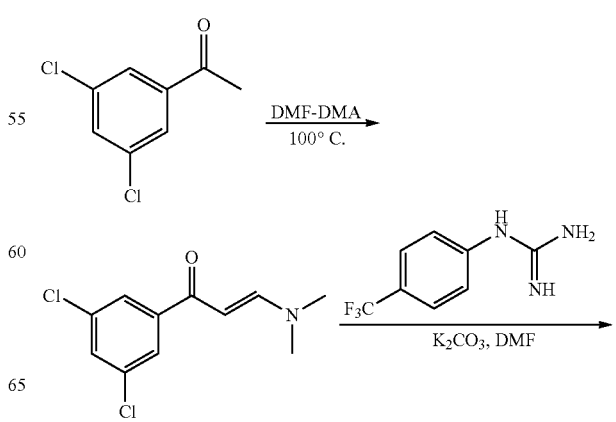

55

-continued

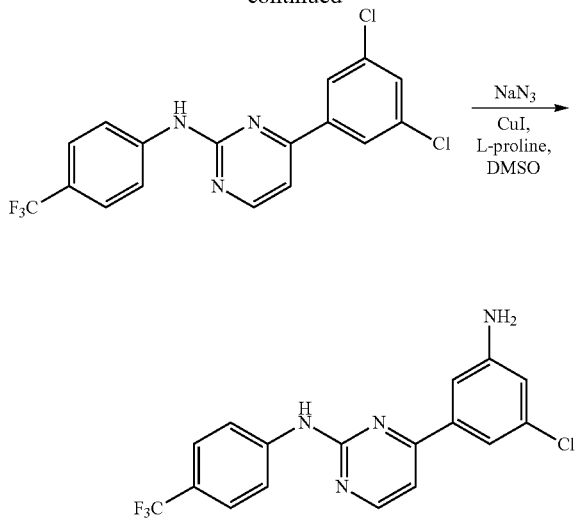

Step 1: (E)-1-(3,5-dichlorophenyl)-3-(dimethylamino)prop-2-en-1-one

A mixture of 1-(3,5-dichlorophenyl)ethan-1-one (2.0 g, 10.58 mmol, 1.0 eq) and DMF-DMA (30.0 mL) was stirred at 100° C. for 16 h under Ar. The reaction was monitored by LC-MS. The mixture was concentrated to dryness and used directly in the next step. LC-MS: [M+H]+ (m/z)=244.1.

Step 2: 4-(3,5-dichlorophenyl)-N-(4-(trifluoromethyl)phenyl)pyrimidin-2-amine

A mixture of (E)-1-(3,5-dichlorophenyl)-3-(dimethylamino)prop-2-en-1-one (300 mg, 1.23 mmol, 1.0 eq), 1-(4-(trifluoromethyl)phenyl)guanidine (274 mg, 1.84 mmol, 1.5 eq) and K$_2$CO$_3$ (424 mg, 3.07 mmol, 2.5 eq) in DMF (5.0 mL) was stirred at 120° C. for 16 h under Ar. The reaction was monitored by LC-MS. The mixture was partitioned between EA/water. The organic phase was dried over Na$_2$SO$_4$, filtered, and concentrated to dryness. The residue was purified by flash chromatography on silica gel (PE/EA=6:1) to give the title compound (310 mg, 66% over 2 steps) as a white solid. LC-MS: [M+H]+ (m/z)=384.0.

Step 3: 4-(3-amino-5-chlorophenyl)-N-(4-(trifluoromethyl)phenyl)pyrimidin-2-amine A mixture of 4-(3,5-dichlorophenyl)-N-(4-(trifluoromethyl)phenyl)pyrimidin-2-amine (100 mg, 0.26 mmol, 1.0 eq), CuI (50 mg, 0.26 mmol, 1.0 eq), L-proline (48 mg, 0.42 mmol, 1.6 eq) and NaN$_3$ (43 mg, 0.65 mmol, 2.5 eq) in DMSO (3.0 mL) was stirred at 135° C. for 16 h under Ar. The reaction was monitored by LC-MS. The mixture was partitioned between EA/water. The organic phase was dried over Na$_2$SO$_4$, filtered and concentrated to dryness. The residue was purified by flash chromatography on silica gel (PE/EA=2:1) to give the title compound (39 mg, 41%) as a white solid. LC-MS: [M+H]+ (m/z)=365.3; $^1$H NMR (400 MHz, CD$_3$OD) δ 8.51 (d, J=5.6 Hz, 1H), 7.99 (d, J=8.4 Hz, 2H), 7.60 (d, J=8.8 Hz, 2H), 7.39-7.35 (m, 2H), 7.26 (d, J=5.2 Hz, 1H), 6.83-6.82 (m, 1H).

56

Example 7: 4-amino-2-(2-((4-(trifluoromethyl)phenyl)amino)pyrimidin-4-yl)benzoic acid

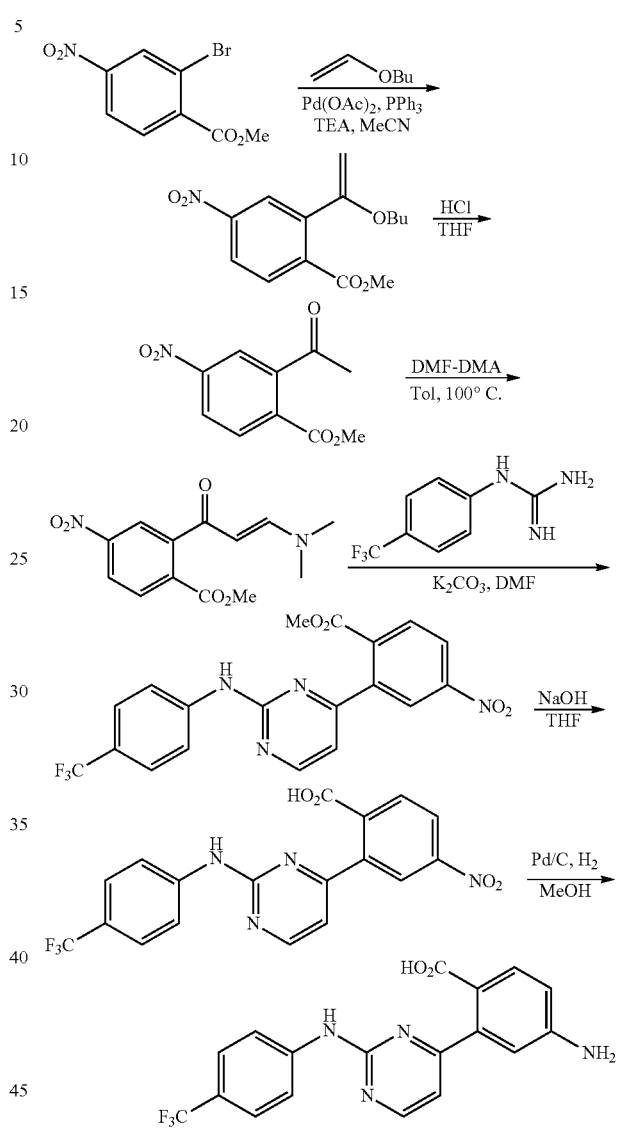

Step 1: methyl 2-(1-butoxyvinyl)-4-nitrobenzoate

To a solution of methyl 2-bromo-4-nitrobenzoate (2.0 g, 7.7 mmol, 1.0 eq) in MeCN (5.0 mL) was added 1-(vinyloxy)butane (3.85 g, 38.5 mmol, 5.0 eq), TEA (0.932 g, 9.2 mmol, 1.2 eq), PPh$_3$ (302 mg, 1.15 mmol, 0.15 eq) and Pd(OAc)$_2$ (129 mg, 0.58 mmol, 0.075 eq). The resulting reaction mixture was heated to 100° C. and stirred for 16 h. The reaction suspension was cooled to RT and filtered through Celite. The filtrate was concentrated, and the residue was purified by flash chromatography on silica gel (eluent: PE/EA=100:1) to give the title compound (1.7 g, 79%) as a yellow oil. LC-MS: [M−H]− (m/z)=278.

Step 2: methyl 2-acetyl-4-nitrobenzoate

To a solution of methyl 2-(1-butoxyvinyl)-4-nitrobenzoate (1.7 g, 6.1 mmol, 1.0 eq) in THF (10 mL) was added 1N aq. HCl (5.0 mL). The reaction mixture was stirred at RT for 3 h, and then quenched with water (30 mL). The mixture was extracted with EA (3×30 mL). The combined organic layer was concentrated, and the residue was purified by flash chromatography on silica gel (eluent: PE/EA=10:1) to give the title compound (1.0 g, 73%) as a yellow oil. LC-MS: [M+H]$^+$ (m/z)=224.

Step 3: methyl (E)-2-(3-(dimethylamino)acryloyl)-4-nitrobenzoate

A solution of methyl 2-acetyl-4-nitrobenzoate (1.0 g, 3.6 mmol, 1.0 eq) and DMF-DMA (2.1 mL, 7N, 14.4 mmol, 4.0 eq) in toluene (10 mL) was heated to 100° C. and stirred for 16 h. The reaction mixture was cooled to RT, concentrated, and purified by flash chromatography on silica gel (eluent: PE/EA=3:1 to 0:1) to give the title compound (1.0 g, 99%) as a yellow oil. LC-MS: [M+H]$^+$ (m/z)=279.

Step 4: methyl 4-nitro-2-(2-((4-(trifluoromethyl)phenyl)amino)pyrimidin-4-yl)benzoate To a solution of methyl (E)-2-(3-(dimethylamino)acryloyl)-4-nitrobenzoate (200 mg, 0.72 mmol, 1.0 eq) in DMF (10 mL) was added 1-(4-(trifluoromethyl)phenyl)guanidine (161 mg, 0.79 mmol, 1.1 eq) and K$_2$CO$_3$ (238 mg, 1.73 mmol, 2.4 eq). The reaction was heated to 120° C. and stirred for 16 h under Ar. The suspension was cooled to RT and filtered, and the cake was washed with THF (100 mL). The filtrate was concentrated to give the title compound (300 mg, 100%) as a yellow oil, which was used directly in next step without further purification. LC-MS: [M+H]$^+$ (m/z)=419.

Step 5: 4-nitro-2-(2-((4-(trifluoromethyl)phenyl)amino)pyrimidin-4-yl)benzoic acid To a solution of methyl 4-nitro-2-(2-((4-(trifluoromethyl)phenyl)amino)pyrimidin-4-yl)benzoate (300 mg, 0.72 mmol, 1.0 eq) in THF (10 mL) was added 4.0 M aq. NaOH (5.0 mL). The reaction solution was heated to 70° C. and stirred for 16 h. After cooled down to RT, the mixture was concentrated, and adjusted to pH 1-2 with 4.0 M aq. HCl. The resulting mixture was extracted with EA (3×50 mL). The combined organic layer was concentrated to give the title compound (250 mg, 86%) as a yellow oil. LC-MS: [M+H]$^+$ (m/z)=405.

Step 6: 4-amino-2-(2-((4-(trifluoromethyl)phenyl)amino)pyrimidin-4-yl)benzoic acid To a solution of 4-nitro-2-(2-((4-(trifluoromethyl)phenyl)amino)pyrimidin-4-yl)benzoic acid (200 mg, 0.5 mmol, 1.0 eq) in MeOH (5.0 mL) was added Pd/C (100 mg). The mixture was stirred at RT for 16 h under H$_2$. The mixture was filtered, and the filtrate was concentrated. The residue was purified by prep-HPLC (mobile phase: CH$_3$CN/H$_2$O/0.1% NH$_3$—H$_2$O) to give the title compound (10 mg, 5.4%) as a light-yellow solid. LC-MS: [M+H]$^+$ (m/z)=375.1; $^1$H NMR (400 MHz, DMSO-d6) δ 9.92 (s, 1H), 8.31 (d, J=4.8 Hz, 1H), 8.05 (d, J=8.4 Hz, 2H), 7.60 (d, J=8.8 Hz, 2H), 7.32 (d, J=7.6 Hz, 1H), 6.94 (d, J=5.2 Hz, 1H), 6.60 (d, J=2.4 Hz, 1H), 6.50 (d, J=8.4 Hz, 1H), 5.05 (s, 2H).

Example 8: 5-amino-2-(2-((4-(trifluoromethyl)phenyl)amino)pyrimidin-4-yl)benzoic acid

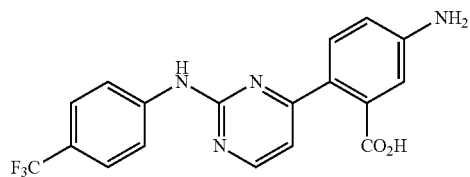 [SMILES: Nc1ccc(-c2ccnc(Nc3ccc(C(F)(F)F)cc3)n2)c(C(=O)O)c1]

Example 8 was prepared following the procedure for example 7 by replacing methyl 2-bromo-4-nitrobenzoate with methyl 2-bromo-5-nitrobenzoate in step 1.

The crude product was purified by prep-HPLC (mobile phase: CH$_3$CN/H$_2$O/0.1% NH$_3$—H$_2$O) to give the title compound (150 mg, 81%) as a light-yellow solid. LC-MS: [M+H]$^+$ (m/z)=375.1; $^1$H NMR (400 MHz, DMSO-d6) δ 10.15 (s, 1H), 8.61 (d, J=5.2 Hz, 1H), 8.08 (d, J=8.4 Hz, 2H), 7.88 (s, 1H), 7.67 (d, J=8.8 Hz, 2H), 7.54 (s, 1H), 7.37 (d, J=5.2 Hz, 1H), 7.35 (s, 1H), 5.60 (br s, 2H).

Example 9: 5-amino-2-(2-((4-(trifluoromethyl)phenyl)amino)pyrimidin-4-yl)benzoic acid

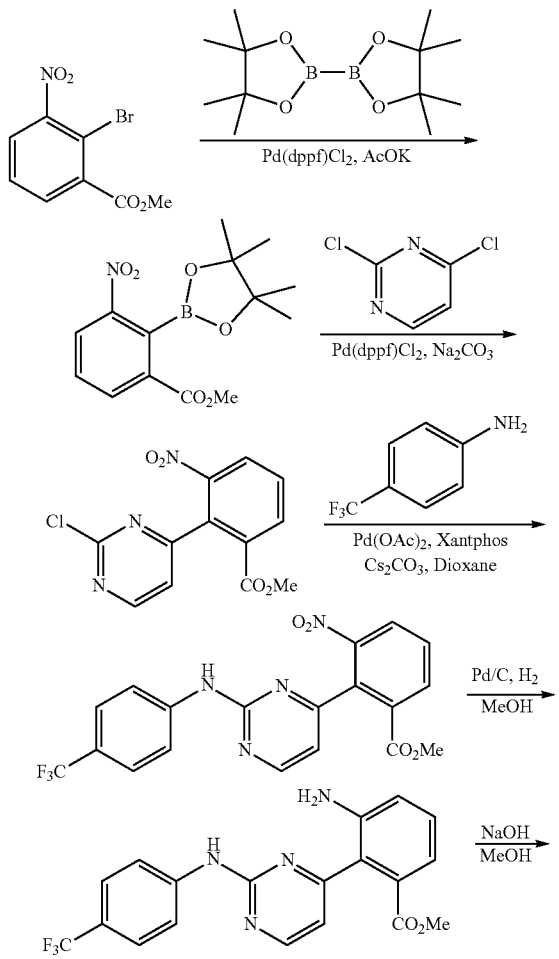

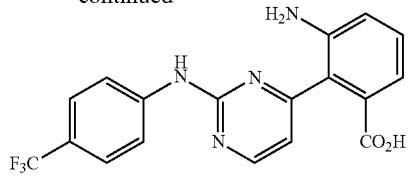

Step 1: methyl 3-nitro-2-(4,4,5,5-tetramethyl-1,3,2-dioxaborolan-2-yl)benzoate

A mixture of methyl 2-bromo-3-nitrobenzoate (5 g, 19.22 mmol, 1.0 eq), 4,4,4',4',5,5,5',5'-octamethyl-2,2'-bi(1,3,2-dioxaborolane) (5.9 g, 23.07 mmol, 1.0 eq), KOAc (5.7 g, 57.68 mmol, 3.0 eq) and Pd(dppf)Cl$_2$ (422 mg, 0.58 mmol, 0.03 eq) in dioxane (50 mL) was stirred at 80° C. for 16 h under Ar. The mixture was partitioned between EA/water. The organic layer was separated, concentrated, and purified by flash chromatography on silica gel (eluent: PE:EA=1:0 to 50:1) to give the title compound (3.1 g, 79%).

Step 2: methyl 2-(2-chloropyrimidin-4-yl)-3-nitrobenzoate

A mixture of methyl 3-nitro-2-(4,4,5,5-tetramethyl-1,3,2-dioxaborolan-2-yl)benzoate (1.5 g, 4.88 mmol, 1.0 eq), 2,4-dichloropyrimidine (728 mg, 4.88 mmol, 1.0 eq), Na$_2$CO$_3$ (1.04 g, 9.77 mmol, 2.0 eq) and Pd(dppf)Cl$_2$ (357 mg, 0.49 mmol, 0.1 eq) in dioxane (30 mL) and H$_2$O (3.0 mL) was stirred at 80° C. for 16 h under Ar. The mixture was partitioned between EA/water. The organic layer was separated, concentrated and purified by flash chromatography on silica gel (eluent: PE:EA=1:0 to 3:1) to give the title compound (462 mg, 33%).

Step 3: methyl 3-nitro-2-(2-((4-(trifluoromethyl)phenyl)amino)pyrimidin-4-yl)benzoate A mixture of methyl 2-(2-chloropyrimidin-4-yl)-3-nitrobenzoate (362 mg, 1.23 mmol, 1.0 eq), 4-(trifluoromethyl)aniline (209 mg, 1.29 mmol, 1.05 eq), Cs$_2$CO$_3$ (769 mg, 2.46 mmol, 2.0 eq), Pd(OAc)$_2$ (26 mg, 0.12 mmol, 0.1 eq) and xantphos (68 mg, 0.12 mmol, 0.1 eq) in dioxane (15 mL) was stirred at 110° C. for 16 h under Ar. The mixture was partitioned between EA/water. The organic layer was separated, concentrated and purified by flash chromatography on silica gel (eluent: PE:EA=1:0 to 3:1) to give the title compound (230 mg, 45%). LC-MS: [M+H]$^+$ (m/z)=419.1.

Step 4: methyl 3-amino-2-(2-((4-(trifluoromethyl)phenyl)amino)pyrimidin-4-yl)benzoate To a solution of methyl 3-nitro-2-(2-((4-(trifluoromethyl)phenyl)amino)pyrimidin-4-yl)benzoate (250 mg, 0.6 mmol, 1.0 eq) in MeOH was added Pd/C (100 mg), and the mixture was stirred overnight at RT under H$_2$. The Pd/C was filtered off, and the filtrate was concentrated to give the title compound (130 mg, 56%). LC-MS: [M+H]$^+$ (m/z)=389.1.

Step 5: 5-amino-2-(2-((4-(trifluoromethyl)phenyl)amino)pyrimidin-4-yl)benzoic acid To a solution of methyl 3-amino-2-(2-((4-(trifluoromethyl)phenyl)amino)pyrimidin-4-yl)benzoate (33 mg, 0.08 mmol, 1.0 eq) in MeOH (5 mL) was added 1 N NaOH (2 mL). The mixture was stirred at 50° C. for 16 h. The reaction was monitored by LC-MS. The mixture was purified by prep-HPLC (mobile phase: CH$_3$CN/H$_2$O/0.1% HCOOH) to give the title compound (7 mg, 22%). LC-MS: [M+H]$^+$ (m/z)=375.1; $^1$H NMR (400 MHz, CD$_3$OD) δ 8.47 (d, J=5.0 Hz, 1H), 7.92 (d, J=8.6 Hz, 2H), 7.54 (d, J=8.7 Hz, 2H), 7.23 (t, J=7.7 Hz, 1H), 7.16 (d, J=8.4 Hz, 1H), 6.97 (d, J=7.5 Hz, 1H), 6.91 (d, J=5.1 Hz, 1H).

Example 10: 2-(4-amino-2-(2-((4-(trifluoromethyl)phenyl)amino)pyrimidin-4-yl)phenyl)acetic acid

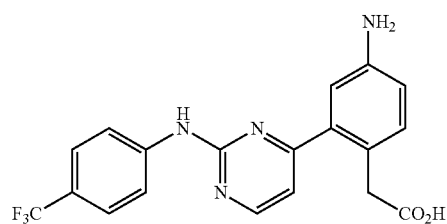 [SMILES: Nc1ccc(CC(=O)O)c(-c2ccnc(Nc3ccc(C(F)(F)F)cc3)n2)c1]

Example 10 was prepared following the protocol for example 9 by replacing methyl 2-bromo-3-nitrobenzoate with methyl 2-(2-bromo-4-nitrophenyl)acetate in step 1.

The crude product was purified by prep-HPLC (mobile phase: CH$_3$CN/H$_2$O/0.1% formic acid) to give the title compound (19 mg, 32%) as a white solid. LC-MS: [M+H]$^+$ (m/z)=389.1; $^1$H NMR (400 MHz, CD$_3$OD) δ 8.50 (d, J=5.2 Hz, 1H), 7.92 (d, J=8.4 Hz, 2H), 7.55 (d, J=8.4 Hz, 2H), 7.12 (d, J=8.4 Hz, 1H), 7.02 (d, J=5.2 Hz, 1H), 6.91 (d, J=2.4 Hz, 1H), 6.80 (dd, J=8.4, 2.4 Hz, 1H), 3.76 (s, 2H).

Example 11: 4-amino-2-(2-((4-(trifluoromethyl)phenyl)amino)pyrimidin-4-yl)phenol

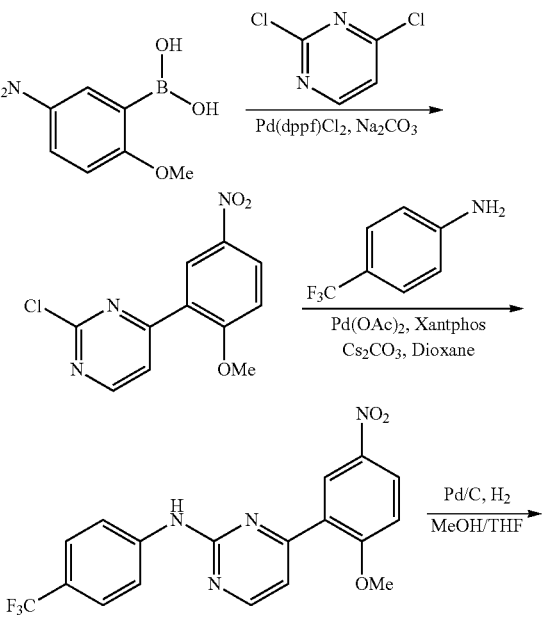

-continued

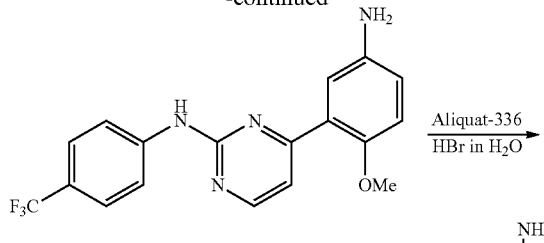

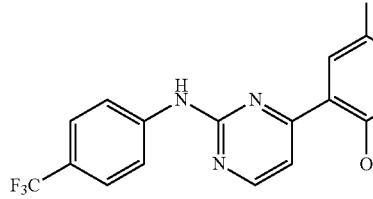

Step 1:
2-chloro-4-(2-methoxy-5-nitrophenyl)pyrimidine

A mixture of (2-methoxy-5-nitrophenyl)boronic acid (240 mg, 1.22 mmol, 1.0 eq), 2,4-dichloropyrimidine (218 mg, 1.46 mmol, 1.2 eq), Na$_2$CO$_3$ (258 mg, 2.44 mmol, 2.0 eq) and PdCl$_2$(dppf) (89 mg, 0.12 mmol, 0.1 eq) in dioxane/H$_2$O (10 mL/1 mL) was stirred at 90° C. for 2 h under Ar. The reaction was monitored by LC-MS. The residue was extracted with DCM/H$_2$O, and the organic phase was dried over Na$_2$SO$_4$, filtered and concentrated to dryness. The residue was purified by flash chromatography on silica gel (eluent: PE/EA=2:1) to give the title compound (182 mg, 56%) as a yellow solid. LC-MS: [M+H]$^+$ (m/z)=266.3.

Step 2: 4-(2-methoxy-5-nitrophenyl)-N-(4-(trifluoromethyl)phenyl)pyrimidin-2-amine A mixture of 2-chloro-4-(2-methoxy-5-nitrophenyl)pyrimidine (182 mg, 0.68 mmol, 1.0 eq), 4-(trifluoromethyl)aniline (131 mg, 0.81 mmol, 1.2 eq), Pd(OAc)$_2$ (30 mg, 0.14 mmol, 0.02 mmol), Xantphos (80 mg, 0.14 mmol, 0.02 mmol) and Cs$_2$CO$_3$ (442 mg, 1.36 mmol, 2.0 eq) in dioxane (5.0 mL) was stirred at 105° C. for 3 h under Ar. The mixture was monitored by LC-MS. The reaction mixture was extracted with DCM/H$_2$O, and the combined organic phase was dried over Na$_2$SO$_4$, filtered and concentrated. The residue was purified by flash chromatography on silica gel (eluent: PE/EA=2:1) to give the title compound (169 mg, 63%) as a yellow solid. LC-MS: [M+H]$^+$ (m/z)=391.3.

Step 3: 4-(5-amino-2-methoxyphenyl)-N-(4-(trifluoromethyl)phenyl)pyrimidin-2-amine A mixture of 4-(2-methoxy-5-nitrophenyl)-N-(4-(trifluoromethyl)phenyl)pyrimidin-2-amine (169 mg, 0.43 mmol, 1.0 eq), Pd/C (20 mg) in MeOH (6.0 mL)/THF (3.0 mL) was stirred at RT for 2 h under H$_2$. The mixture was monitored by LC-MS. The residue was filtered, and the filtrate was concentrated to give the title compound (138 mg, 89%) as a white solid. LC-MS: [M+H]$^+$ (m/z)=361.3.

Step 4: 4-amino-2-(2-((4-(trifluoromethyl)phenyl)amino)pyrimidin-4-yl)phenol

A mixture of 4-(5-amino-2-methoxyphenyl)-N-(4-(trifluoromethyl)phenyl)pyrimidin-2-amine (138 mg, 0.38 mmol, 1.0 eq) and Aliquat®-336 (155 mg, 0.38 mmol, 1.0 eq) in 48% HBr (5.0 mL) was stirred at 105° C. for 16 h. The mixture was monitored by LC-MS. The mixture was purified by prep-HPLC (mobile phase: CH$_3$CN/H$_2$O/0.1% NH$_4$HCO$_3$) to give the title compound (55.1 mg, 42%) as a yellow solid. LC-MS: [M+H]$^+$ (m/z)=347.2; $^1$H NMR (400 MHz, CD$_3$OD) δ 8.54 (d, J=5.6 Hz, 1H), 7.88 (d, J=8.4 Hz, 2H), 7.60 (d, J=8.4 Hz, 2H), 7.38 (d, J=5.6 Hz, 1H), 7.32 (d, J=2.8 Hz, 1H), 6.89 (dd, J=8.8, 2.8 Hz, 1H), 6.78 (d, J=8.8 Hz, 1H).

Example 12: 4-amino-3-(2-((4-(trifluoromethyl)phenyl)amino)pyrimidin-4-yl)phenol

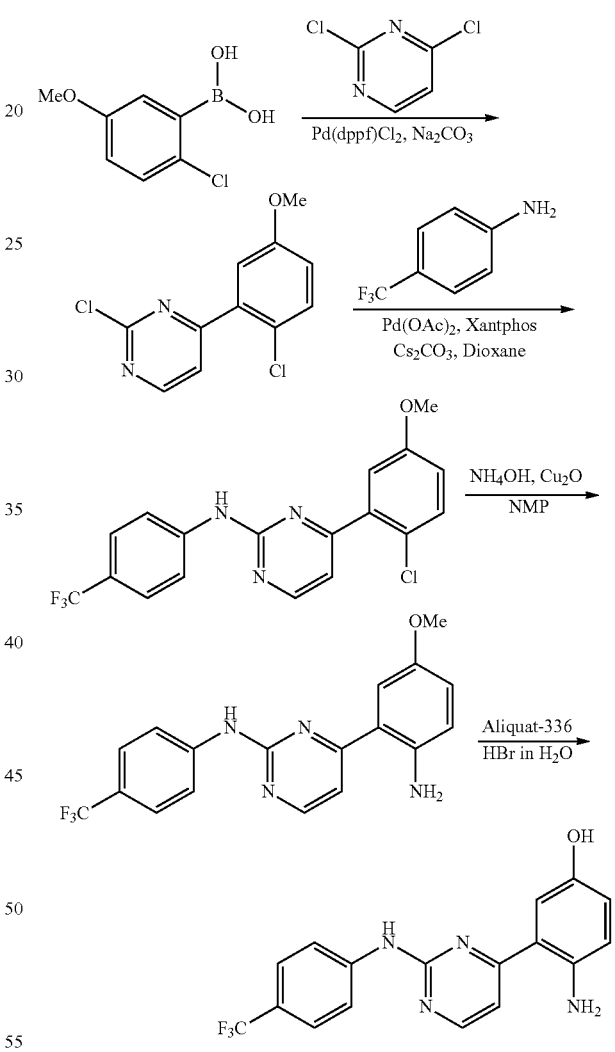

Step 1:
2-chloro-4-(2-chloro-5-methoxyphenyl)pyrimidine

A mixture of (2-chloro-5-methoxyphenyl)boronic acid (50 mg, 0.27 mmol, 1.0 eq), Pd(dppf)Cl$_2$ (21 mg, 0.03 mmol, 0.03 eq), Na$_2$CO$_3$ (57 mg, 0.54 mmol, 2.0 eq) and 2,4-dichloropyrimidine (80 mg, 0.54 mmol, 2.0 eq) in dioxane/H$_2$O (v/v=10:1, 11 mL) was stirred at 100° C. for 16 h. The reaction was monitored by LC-MS. The mixture was diluted with water (10 mL) and filtered. The filtrate was concentrated under reduced pressure, and the residue was purified by prep-TLC (eluent: PE/EA=3:1) to give the title compound (50 mg, 73.5%) as a yellow oil. LC-MS: [M+H]⁺ (m/z)=255.3.

Step 2: 4-(2-chloro-5-methoxyphenyl)-N-(4-(trifluoromethyl)phenyl)pyrimidin-2-amine A mixture of 2-chloro-4-(2-chloro-5-methoxyphenyl)pyrimidine (60 mg, 0.24 mmol, 1.0 eq), 4-(trifluoromethyl)aniline (42 mg, 0.29 mmol, 1.1 eq), Pd(OAc)$_2$ (6.0 mg, 0.02 mmol, 0.1 eq), xantphos (14 mg, 0.02 mmol, 0.1 eq) and Cs$_2$CO$_3$ (154 mg, 0.47 mmol, 2.0 eq) in dioxane (1.0 mL) was stirred at 110° C. for 4 h under Ar. The mixture was filtered, and the filtrate was concentrated under reduced pressure. The residue was purified by prep-TLC (eluent: PE/EA=3:1) to give the title compound (48 mg, 53%) as a yellow oil. LC-MS: [M+H]⁺ (m/z)=380.3.

Step 3: 4-(2-amino-5-methoxyphenyl)-N-(4-(trifluoromethyl)phenyl)pyrimidin-2-amine A mixture of 4-(2-chloro-5-methoxyphenyl)-N-(4-(trifluoromethyl)phenyl)pyrimidin-2-amine (40 mg, 0.11 mmol, 1.0 eq), Cu$_2$O (2 mg, 0.01 mmol, 0.10 eq) in NH$_3$—H$_2$O and NMP (v/v=1:1, 6.0 mL) was stirred at 110° C. for 72 h. The reaction was monitored by LC-MS. The reaction was quenched with ice-water (10 mL), and the resulting mixture was filtered. The filter cake was washed with water, dried under reduced pressure, and purified by flash chromatography on silica gel (eluent: PE:EA=20:1 to 5:1) to give the title compound (800.0 mg, 55%) as a yellow solid. LC-MS: [M+H]⁺ (m/z)=361.4.

Step 4: 4-amino-3-(2-((4-(trifluoromethyl)phenyl)amino)pyrimidin-4-yl)phenol

A solution of 4-(2-amino-5-methoxyphenyl)-N-(4-(trifluoromethyl)phenyl)pyrimidin-2-amine (100 mg, 0.28 mmol, 1.0 eq), Aliquat®-336 (33.7 mg, 0.08 mmol, 0.3 eq) in HBr (48% in H$_2$O) (4.0 mL) was stirred at 105° C. for 16 h. The reaction was monitored by LC-MS. The reaction mixture was purified by prep-HPLC (mobile phase: MeCN/H$_2$O/0.1% FA) to give the title compound (20.0 mg, 21%) as a white solid. LC-MS: [M+H]⁺ (m/z)=347.1; ¹H NMR (400 MHz, CD$_3$OD) δ 8.52 (d, J=5.6 Hz, 1H), 7.90 (d, J=8.8 Hz, 2H), 7.59 (d, J=8.4 Hz, 2H), 7.21 (d, J=5.6 Hz, 1H), 7.16 (d, J=2.4 Hz, 1H), 6.85 (d, J=8.8 Hz, 1H), 7.17 (dd, J=8.8, 2.4 Hz, 1H).

Examples 13: 4-(2-amino-5-(methylsulfonyl)phenyl)-N-(4-(trifluoromethyl)phenyl)pyrimidin-2-amine

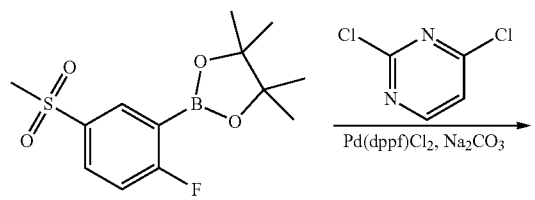

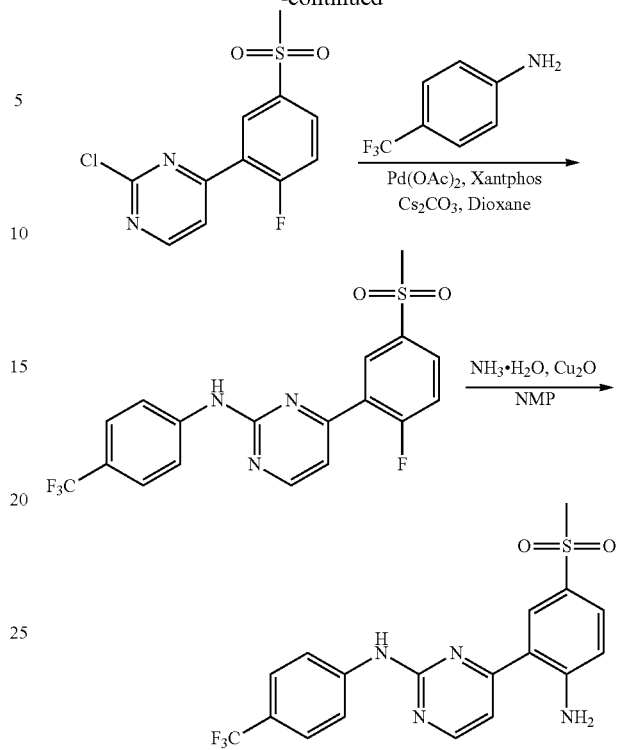

Step 1: 2-chloro-4-(2-fluoro-5-(methylsulfonyl)phenyl)pyrimidine

A mixture of 2-(2-fluoro-5-(methylsulfonyl)phenyl)-4,4,5,5-tetramethyl-1,3,2-dioxaborolane (650 mg, 2.17 mmol, 1.0 eq), 2,4-dichloropyrimidine (419 mg, 2.82 mmol, 1.3 eq), Pd(dppf)Cl$_2$ (158.4 mg, 0.22 mmol, 0.1 eq), and Na$_2$CO$_3$ (459 mg, 4.33 mmol, 2.0 eq) in dioxane (5 mL) and 2 drops of H$_2$O was stirred at 90° C. for 16 h under Ar. The mixture was filtered. The filtrate was concentrated and purified by flash chromatography on silica gel (PE:EA=10:1 to 2:1) to give the title compound (462 mg, 60%) as a yellow oil. LC-MS: [M+H]⁺ (m/z)=287.0.

Step 2: 4-(2-fluoro-5-(methylsulfonyl)phenyl)-N-(4-(trifluoromethyl)phenyl)pyrimidin-2-amine A mixture of 2-chloro-4-(2-fluoro-5-(methylsulfonyl)phenyl)pyrimidine (462 mg, 1.62 mmol, 1.0 eq), 4-(trifluoromethyl)aniline (287 mg, 1.78 mmol, 1.1 eq), Pd(OAc)$_2$ (73 mg, 0.32 mmol, 0.2 eq) and Cs$_2$CO$_3$ (1.05 g, 3.24 mmol, 2.0 eq) in dioxane (10 mL) was stirred at 90° C. for 16 h under Ar. The reaction was monitored by LC-MS. The mixture was filtered, and the filtrate was concentrated to dryness. The residue was purified by flash chromatography on silica gel (PE:EA=100:1 to 1:1) to give the title compound (134 mg, 20%) as a yellow oil. LC-MS: [M+H]⁺ (m/z)=412.0.

Step 3: 4-(2-amino-5-(methylsulfonyl)phenyl)-N-(4-(trifluoromethyl)phenyl)pyrimidin-2-amine To a solution of 4-(2-fluoro-5-(methylsulfonyl)phenyl)-N-(4-(trifluoromethyl)phenyl)pyrimidin-2-amine (134 mg, 0.33 mmol, 1.0 eq) in NMP (1 mL) were added Cu$_2$O (50 mg) and NH$_3$·H$_2$O (4 mL) at RT. The resulting mixture was stirred at 90° C. for 16 h. The mixture was diluted with water, and extracted with EA. The combined organic phase was washed with brine, dried over Na$_2$SO$_4$, and concentrated. The residue was purified by prep-HPLC (MeCN/H$_2$O/0.1% HCOOH) to give the title compound (8.8 mg, 6.6%) and 7.02 mg of byproduct. LC-MS: [M+H]$^+$ (m/z)=409.0; $^1$H NMR (400 MHz, CD$_3$OD) δ 8.66 (d, J=5.6 Hz, 1H), 8.55 (d, J=2.4 Hz, 1H), 7.96-7.86 (m, 3H), 7.62 (d, J=8.8 Hz, 2H), 7.60 (d, J=5.2 Hz, 1H), 7.17 (d, J=8.8 Hz, 1H), 3.15 (s, 3H). Byproduct: LC-MS: [M+H]$^+$ (m/z)=410.0; $^1$H NMR (400 MHz, CDCl$_3$) δ 13.80 (s, 1H), 8.64 (d, J=5.2 Hz, 1H), 8.40 (d, J=2.4 Hz, 1H), 7.91 (dd, J=8.8, 2.0 Hz, 1H), 7.67 (s, 4H), 7.40 (d, J=5.6 Hz, 1H), 7.33 (s, 1H), 7.16 (d, J=8.8 Hz, 1H), 3.09 (s, 3H).

Example 14: 4-(5-amino-2-(methylsulfonyl)phenyl)-N-(4-(trifluoromethyl)phenyl)pyrimidin-2-amine

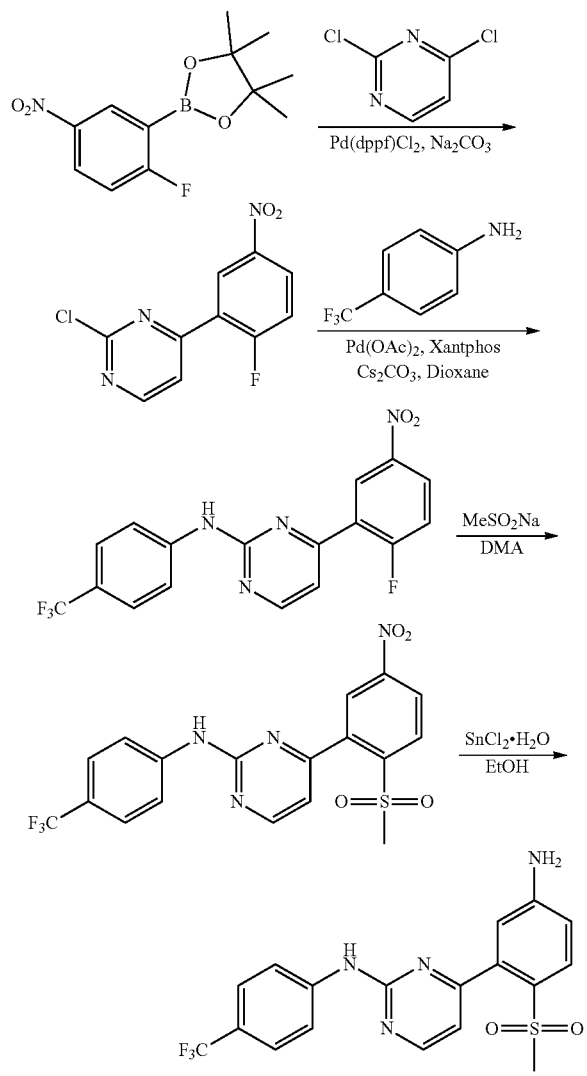

Step 1: 2-chloro-4-(2-fluoro-5-nitrophenyl)pyrimidine

A mixture of 2-(2-fluoro-5-nitrophenyl)-4,4,5,5-tetramethyl-1,3,2-dioxaborolane (500 mg, 1.87 mmol, 1.0 eq), 2,4-dichloropyrimidine (363 mg, 2.43 mmol, 1.3 eq), Pd(dppf)Cl$_2$ (68 mg, 0.094 mmol, 0.05 eq) and Na$_2$CO$_3$ (397 mg, 3.74 mmol, 2.0 eq) in dioxane/H$_2$O (10:1, 10 mL) was stirred at 90° C. for 16 h under Ar. The reaction was monitored by LC-MS. The mixture was filtered, and the filtrate was concentrated. The residue was purified by flash chromatography on silica gel (eluent: PE/EA=50:1 to 10:1) to give the title compound (300 mg, 67%) as a yellow solid. LC-MS: [M+H]$^+$ (m/z)=254.

Step 2: 4-(2-fluoro-5-nitrophenyl)-N-(4-(trifluoromethyl)phenyl)pyrimidin-2-amine A mixture of 2-chloro-4-(2-fluoro-5-nitrophenyl)pyrimidine (300 mg, 1.18 mmol, 1.0 eq), 4-(trifluoromethyl)aniline (229 mg, 1.42 mmol, 1.2 eq), Pd(OAc)$_2$ (13 mg, 0.06 mmol, 0.05 eq), xantphos (68 mg, 0.12 mmol, 0.1 eq) and Cs$_2$CO$_3$ (771 mg, 2.37 mmol, 2.0 eq) in dioxane (10 mL) was stirred at 100° C. for 0.5 h under Ar. The reaction was monitored by LC-MS. The mixture was filtered, and the filtrate was concentrated. The residue was purified by flash chromatography on silica gel (eluent: PE/EA=100:1 to 10:1) to give the crude product, which was further purified by trituration (PE) to give the title compound (30 mg, 7%) as yellow solid. LC-MS: [M+H]$^+$ (m/z)=379.1.

Step 3: 4-(2-(methylsulfonyl)-5-nitrophenyl)-N-(4-(trifluoromethyl)phenyl)pyrimidin-2-amine A mixture of 4-(2-fluoro-5-nitrophenyl)-N-(4-(trifluoromethyl)phenyl)pyrimidin-2-amine (30 mg, 0.08 mmol, 1.0 eq) and MeSO$_2$Na (40.5 mg, 0.40 mmol, 5.0 eq) in DMA (10 mL) was stirred at RT for 2 h. The reaction was monitored by LC-MS. The mixture was diluted with water and EtOAc. The organic layer was separated, washed with brine, dried over Na$_2$SO$_4$, and concentrated to give the title compound (35 mg, 100%) as a yellow solid. LC-MS: [M+H]+ (m/z)=439.

Step 4: 4-(5-amino-2-(methylsulfonyl)phenyl)-N-(4-(trifluoromethyl)phenyl)pyrimidin-2-amine A mixture of 4-(2-(methylsulfonyl)-5-nitrophenyl)-N-(4-(trifluoromethyl)phenyl)pyrimidin-2-amine (35 mg, 0.08 mmol, 1.0 eq) and SnCl$_2$·2H$_2$O (90 mg, 0.40 mmol, 5.0 eq) in EtOH (5.0 mL) was stirred at 80° C. for 16 h under Ar. The reaction was monitored by LC-MS. The mixture was worked up and concentrated, and the residue was purified by prep-TLC (PE/EA=1:1) to give the title compound (23.57 mg, 72%) as a yellow solid. LC-MS: [M+H]$^+$ (m/z)=409.1; $^1$H NMR (400 MHz, CD$_3$OD) δ 8.52 (d, J=4.8 Hz, 1H), 7.90 (d, J=8.4 Hz, 2H), 7.75 (d, J=8.4 Hz, 1H), 7.55 (d, J=8.8 Hz, 2H), 6.91 (d, J=5.2 Hz, 1H), 6.78 (dd, J=8.8, 2.4 Hz, 1H), 6.64 (d, J=2.4 Hz, 1H), 3.25 (s, 3H).

Example 15: 4-(2-aminophenyl)-N-(3-(trifluoromethyl)phenyl)pyrimidin-2-amine

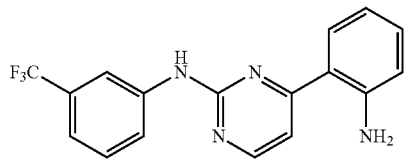 [SMILES: Nc1ccccc1-c1ccnc(Nc2cccc(C(F)(F)F)c2)n1]

Example 15 was prepared following the procedure for example 3 by replacing 4-(trifluoromethyl)aniline with 3-(trifluoromethyl)aniline in step 2.

The crude product was purified by prep-HPLC (CH$_3$CN/H$_2$O/0.1% NH$_3$·H$_2$O) to give the title compound (26 mg, 57%) as a yellow solid. LC-MS: [M+H]$^+$ (m/z)=331.2; $^1$H NMR (400 MHz, DMSO-d6) δ 10.00 (s, 1H), 8.51 (d, J=5.6 Hz, 1H), 8.22 (s, 1H), 8.02 (d, J=7.6 Hz, 1H), 7.72 (d, J=8.0 Hz, 1H), 7.54 (t, J=7.6 Hz, 1H), 7.34 (d, J=5.6 Hz, 1H), 7.29 (d, J=7.6 Hz, 1H), 7.17 (t, J=7.6 Hz, 1H), 7.01 (br s, 2H), 6.81 (dd, J=8.4, 0.8 Hz, 1H), 6.60 (t, J=8.0 Hz, 1H).

Example 16: 4-(3-aminophenyl)-N-(3-(trifluoromethyl)phenyl)pyrimidin-2-amine

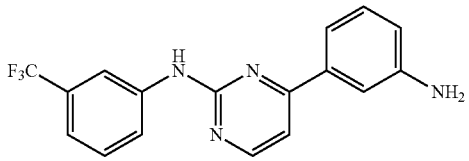 [SMILES: Nc1cccc(-c2ccnc(Nc3cccc(C(F)(F)F)c3)n2)c1]

Example 16 was prepared following the procedure for example 2, by replacing 4-(trifluoromethyl)aniline with 3-(trifluoromethyl)aniline in step 2.

The crude product was purified by prep-HPLC (mobile phase: CH$_3$CN/H$_2$O/0.1% HCOOH) to give the title compound (87 mg, 31.7%) as a yellow solid. LC-MS: [M+H]$^+$ (m/z)=331.1; $^1$H NMR (400 MHz, DMSO-d6) δ 10.07 (s, 1H), 8.62 (d, J=5.2 Hz, 1H), 8.36 (s, 1H), 8.11-8.00 (m, 1H), 7.67 (br s, 2H), 7.57 (t, J=8.0 Hz, 1H), 7.42-7.37 (m, 2H), 7.30 (d, J=8.0 Hz, 1H), 7.09 (d, J=7.6 Hz, 1H).

Example 17: 4-((4-(2-aminophenyl)pyrimidin-2-yl)amino)benzoic acid

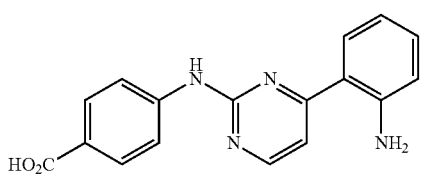 [SMILES: Nc1ccccc1-c1ccnc(Nc2ccc(C(=O)O)cc2)n1]

Example 17 was prepared following the procedure for example 3, by replacing 4-(trifluoromethyl)aniline with methyl 4-aminobenzoate in step 2, followed by converting ester to acid using NaOH.

The crude product was purified by prep-HPLC (CH$_3$CN/H$_2$O/0.1% NH$_3$·H$_2$O) to give the title compound (11 mg, 11%) as a yellow solid. LC-MS: [M+H]$^+$ (m/z)=307.2; $^1$H NMR (400 MHz, DMSO-d6) δ 9.83 (s, 1H), 8.48 (d, J=5.6 Hz, 1H), 7.84 (d, J=8.8 Hz, 2H), 7.74-7.69 (m, 3H), 7.29 (d, J=5.6 Hz, 1H), 7.16-7.14 (m, 1H), 7.03 (br s, 2H), 6.80 (d, J=8.4 Hz, 1H), 6.59 (t, J=7.6 Hz, 1H).

Example 18: 4-((4-(3-aminophenyl)pyrimidin-2-yl)amino)benzoic acid

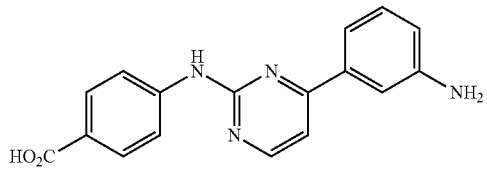 [SMILES: Nc1cccc(-c2ccnc(Nc3ccc(C(=O)O)cc3)n2)c1]

Example 18 was prepared following the procedure for example 2, by replacing 4-(trifluoromethyl)aniline with methyl 4-aminobenzoate in step 2, followed by hydrolysis of ester to acid using NaOH.

The mixture was purified by prep-HPLC (mobile phase: CH$_3$CN/H$_2$O/0.1% NH$_3$·H$_2$O) to give the title compound (33 mg, 34%) as a yellow solid. LC-MS: [M+H]$^+$ (m/z)=307.1; $^1$H NMR (400 MHz, DMSO-d6) δ 9.66 (s, 1H), 8.51 (d, J=5.2 Hz, 1H), 7.83 (d, J=8.8 Hz, 2H), 7.77 (d, J=8.4 Hz, 2H), 7.36 (s, 1H), 7.27 (d, J=8.0 Hz, 1H), 7.24 (d, J=5.2 Hz, 1H), 7.18 (t, J=7.6 Hz, 1H), 6.73 (dd, J=7.6, 1.6 Hz, 1H), 5.31 (br s, 2H).

Example 19: 3-((4-(2-aminophenyl)pyrimidin-2-yl)amino)benzoic acid

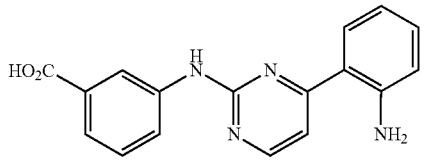 [SMILES: Nc1ccccc1-c1ccnc(Nc2cccc(C(=O)O)c2)n1]

Example 19 was prepared following the procedure for example 3, by replacing 4-(trifluoromethyl)aniline with methyl 3-aminobenzoate in step 2, followed by converting ester to acid using NaOH.

The crude product was purified by prep-HPLC (CH$_3$CN/H$_2$O/0.1% NH$_3$·H$_2$O) to give the title compound (10 mg, 10%) as a yellow solid. LC-MS: [M+H]$^+$ (m/z)=307.1; $^1$H NMR (400 MHz, DMSO-d6) δ 9.56-9.59 (m, 1H), 8.41 (d, J=5.2 Hz, 1H), 8.04-7.99 (m, 1H), 7.81-7.78 (m, 1H), 7.70 (d, J=6.8 Hz, 1H), 7.46 (m, 1H), 7.21-7.11 (m, 3H), 7.04 (br s, 2H) 6.78 (d, J=8.0 Hz, 1H), 6.57 (t, J=7.6 Hz, 1H).

Example 20: 3-((4-(3-aminophenyl)pyrimidin-2-yl)amino)benzoic acid

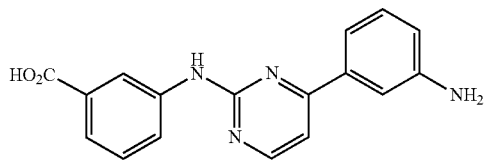 [SMILES: Nc1cccc(-c2ccnc(Nc3cccc(C(=O)O)c3)n2)c1]

Example 20 was prepared following the procedure for example 2, by replacing 4-(trifluoromethyl)aniline with methyl 3-aminobenzoate in step 2, followed by converting ester to acid using NaOH.

The mixture was purified by prep-HPLC (mobile phase: CH$_3$CN/H$_2$O/0.1% NH$_3$·H$_2$O) to give the title compound (58 mg, 30.3%) as a yellow solid. LC-MS: [M+H]$^+$ (m/z)=307.1; $^1$H NMR (400 MHz, DMSO-d6) δ 9.58 (s, 1H), 8.80 (s, 1H), 8.48 (d, J=5.2 Hz, 1H), 7.76 (s, 1H), 7.66 (d, J=7.6 Hz, 1H), 7.48 (d, J=7.2 Hz, 1H), 7.29-7.21 (m, 3H), 7.15 (t, J=7.6 Hz, 1H), 6.72 (dd, J=8.0, 1.6 Hz, 1H), 5.35 (br s, 2H).

Example 21: N$^1$-(4-(3-chlorophenyl)pyrimidin-2-yl)-4-(trifluoromethyl)benzene-1,2-diamine

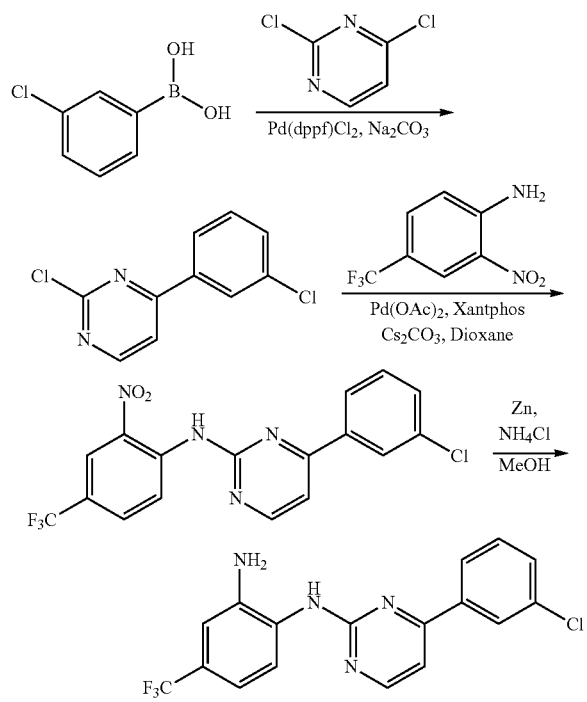

Step 1: 2-chloro-4-(3-chlorophenyl)pyrimidine

A mixture of (3-chlorophenyl)boronic acid (1.0 g, 6.4 mmol, 1.0 eq), 2,4-dichloropyrimidine (0.95 g, 6.4 mmol, 1.0 eq), Na$_2$CO$_3$ (1.36 g, 12.8 mmol, 2.0 eq) and PdCl$_2$(dppf)-DCM (522 mg, 0.64 mmol, 0.1 eq) in dioxane/H$_2$O (20 mL/2.0 mL) was stirred at 90° C. for 16 h under Ar. The reaction was monitored by LC-MS. The mixture was diluted with DCM/H$_2$O, and the organic phase was separated, dried over Na$_2$SO$_4$, filtered and concentrated.

The residue was purified by flash chromatography on silica gel (eluent: PE/EA=10:1) to give the title compound (1.11 g, 78%) as a white solid. LC-MS: [M+H]$^+$ (m/z)=225.1.

Step 2: 4-(3-chlorophenyl)-N-(2-nitro-4-(trifluoromethyl)phenyl)pyrimidin-2-amine A mixture of 2-chloro-4-(3-chlorophenyl)pyrimidine (100 mg, 0.485 mmol, 1.0 eq), 2-nitro-4-(trifluoromethyl)aniline (109 mg, 0.49 mmol, 1.0 eq), Pd(OAc)$_2$ (22 mg, 0.10 mmol, 0.2 eq), Xantphos (56 mg, 0.10 mmol, 0.2 eq) and Cs$_2$CO$_3$ (315 mg, 0.97 mmol, 2.0 eq) in dioxane (3.0 mL) was stirred at 105° C. for 2 h under Ar. The mixture was monitored by LC-MS.

The mixture was partitioned between DCM/water. The organic phase was dried over Na$_2$SO$_4$, filtered and concentrated to dryness. The residue was purified by prep-TLC (eluent: PE/EA=8:1) to give the title compound (91 mg, 47%) as a yellow solid. LC-MS: [M−H]$^−$ (m/z)=393.1.

Step 3: N$^1$-(4-(3-chlorophenyl)pyrimidin-2-yl)-4-(trifluoromethyl)benzene-1,2-diamine A mixture of 4-(3-chlorophenyl)-N-(2-nitro-4-(trifluoromethyl)phenyl)pyrimidin-2-amine (80 mg, 0.2 mmol, 1.0 eq), Zn (65 mg, 1.0 mmol, 5.0 eq) in MeOH/NH$_4$Cl (6.0 mL/2.0 mL) was stirred at r.t for 2 h under Ar. The reaction was monitored by LC-MS. The mixture was purified by prep-HPLC (mobile phase: CH$_3$CN/H$_2$O/0.1% NH$_3$·H$_2$O), freeze-dried to give the title compound (26.28 mg, 35%) as a white solid. LC-MS: [M+H]$^+$ (m/z)=365.3; $^1$H NMR (400 MHz, CD$_3$OD) δ 8.43 (d, J=5.2 Hz, 1H), 8.15 (s, 1H), 8.03-8.01 (m, 1H), 7.68 (d, J=8.4 Hz, 1H), 7.51-7.45 (m, 2H), 7.32 (d, J=5.2 Hz, 1H), 7.14 (d, J=1.6 Hz, 1H), 6.98 (d, J=8.0 Hz, 1H).

Example 22: N$^1$-(4-(3-chlorophenyl)pyrimidin-2-yl)-4-(trifluoromethyl)benzene-1,3-diamine

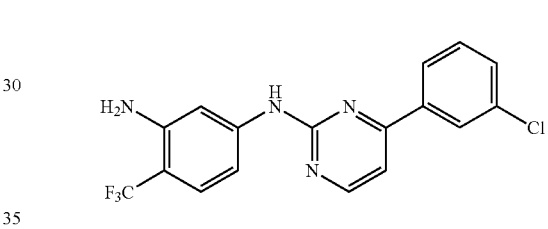

Example 22 was prepared following the protocol for example 21, by replacing 2-nitro-4-(trifluoromethyl)aniline with 3-nitro-4-(trifluoromethyl)aniline in step 2.

The crude product was purified by prep-HPLC (mobile phase: CH$_3$CN/H$_2$O/0.1% NH$_3$—H$_2$O) to give the title compound (66.09 mg, 66%) as a white solid. LC-MS: [M+H]$^+$ (m/z)=365.3; $^1$H NMR (400 MHz, CD$_3$OD) δ 8.52 (d, J=5.2 Hz, 1H), 8.20 (s, 1H), 8.09-8.06 (m, 1H), 7.51-7.50 (m, 2H), 7.41 (s, 1H), 7.35 (d, J=5.2 Hz, 1H), 7.30 (d, J=8.8 Hz, 1H), 7.09 (d, J=8.0 Hz, 1H).

Example 23: 2-(2-((3-amino-4-(trifluoromethyl)phenyl)amino)pyrimidin-4-yl)benzoic acid

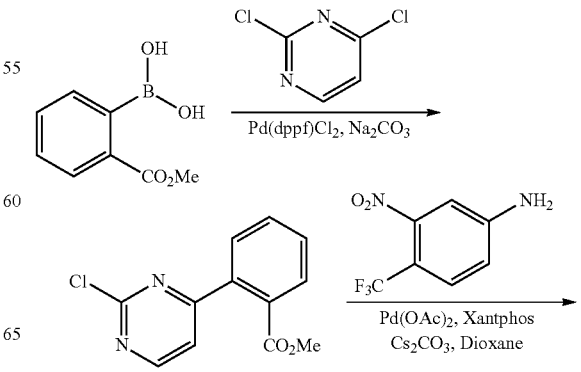

71

-continued

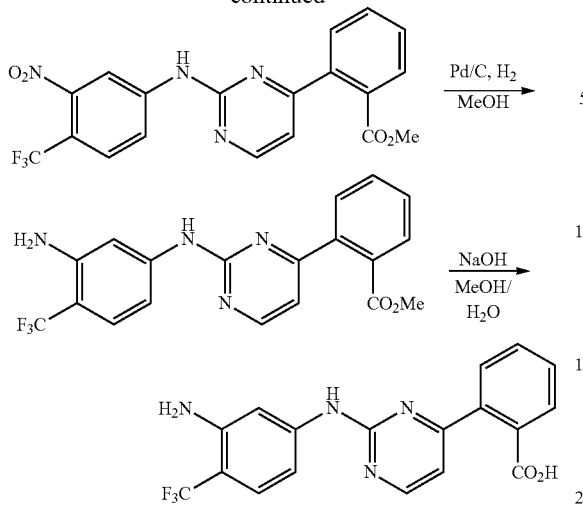

72

Step 4: 2-(2-((3-amino-4-(trifluoromethyl)phenyl)amino)pyrimidin-4-yl)benzoic acid A mixture of methyl 2-(2-((3-amino-4-(trifluoromethyl)phenyl)amino)pyrimidin-4-yl)benzoate (100 mg, 0.26 mmol, 1.0 eq) and NaOH (52 mg, 1.29 mmol, 5.0 eq) in MeOH/H$_2$O (5.5 mL, v/v=10:1) was stirred at 50° C. for 16 h. The reaction was monitored by LC-MS. Then MeOH was evaporated. The aqueous layer was adjusted to pH ~7 with 1.0 M aq HCl. The mixture was purified by prep-HPLC (mobile phase: CH$_3$CN/H$_2$O/0.1% NH$_3$·H$_2$O) to give the title compound (50.3 mg, 32%) as a white solid. LC-MS: [M+H]$^+$ (m/z)=375.1; $^1$H NMR (400 MHz, CD$_3$OD) δ 8.48 (d, J=5.2 Hz, 1H), 7.78-7.75 (m, 1H), 7.65-7.51 (m, 4H), 7.24 (d, J=8.8 Hz, 1H), 7.08 (d, J=4.8 Hz, 1H), 6.88 (d, J=8.0 Hz, 1H); $^{19}$F NMR (400 MHz, CD$_3$OD) δ−62.84.

Example 24: 3-(2-((3-amino-4-(trifluoromethyl)phenyl)amino)pyrimidin-4-yl)benzoic acid

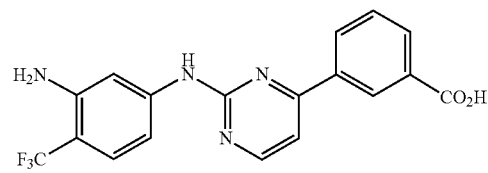 [SMILES: Nc1cc(Nc2nccc(-c3cccc(C(=O)O)c3)n2)ccc1C(F)(F)F]

Example 24 was prepared following the procedure for example 23, by replacing (2-(methoxycarbonyl)phenyl)boronic acid with (3-(ethoxycarbonyl)phenyl)boronic acid in step 1.

The mixture was purified by prep-HPLC (mobile phase: CH$_3$CN/H$_2$O/0.1% NH$_3$·H$_2$O) to give the title compound (68.3 mg, 60%) as a white solid. LC-MS: [M+H]$^+$ (m/z)=375.1; $^1$H NMR (400 MHz, CD$_3$OD) δ 8.94 (t, J=1.6 Hz, 1H), 8.54 (d, J=5.6 Hz, 1H), 8.44 (d, J=7.6 Hz, 1H), 8.24 (d, J=8.0 Hz, 1H), 7.78 (s, 1H), 7.69 (t, J=7.6 Hz, 1H), 7.60 (d, J=6.0 Hz, 1H), 7.53 (d, J=8.4 Hz, 1H), 7.26 (d, J=9.6 Hz, 1H).

Example 25: 2-(2-((4-aminophenyl)amino)pyrimidin-4-yl)phenol

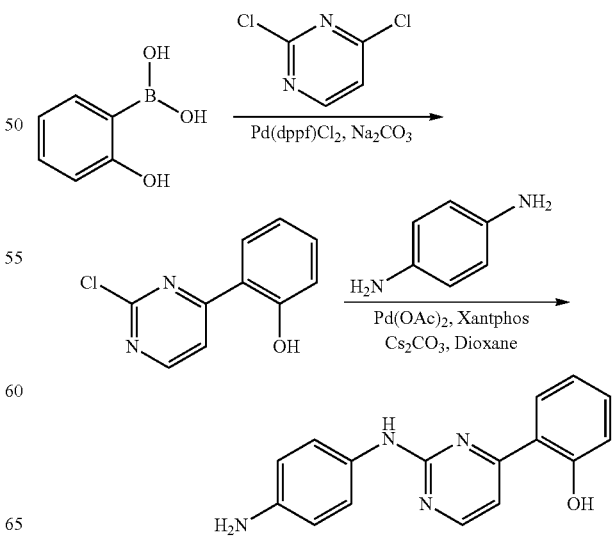

Step 1: methyl 2-(2-chloropyrimidin-4-yl)benzoate

A mixture of (2-(methoxycarbonyl)phenyl)boronic acid (1.0 g, 5.05 mmol, 1.0 eq), 2,4-dichloropyrimidine (0.83 g, 5.05 mmol, 1.0 eq), Na$_2$CO$_3$ (1.18 g, 11.1 mmol, 2.0 eq), and Pd(dppf)Cl$_2$ (407 mg, 0.6 mmol, 0.1 eq) in dioxane/H$_2$O (10 mL/2 mL) was stirred at 90° C. for 16 h under Ar. The reaction was monitored by LC-MS. The mixture was diluted with DCM/H$_2$O. The organic phase was dried over Na$_2$SO$_4$, filtered and concentrated to dryness. The residue was purified by flash chromatography on silica gel (eluent: PE/EA=5:1) to give the title compound (0.9 g, 66%) as a yellow solid. LC-MS: [M+H]$^+$ (m/z)=249.4.

Step 2: methyl 2-(2-((3-nitro-4-(trifluoromethyl)phenyl)amino)pyrimidin-4-yl)benzoate A mixture of methyl 2-(2-chloropyrimidin-4-yl)benzoate (500 mg, 2.01 mmol, 1.0 eq), 3-nitro-4-(trifluoromethyl)aniline (435 mg, 2.11 mmol, 1.05 eq), Pd(OAc)$_2$ (91 mg, 0.40 mmol, 0.2 mmol), Xantphos (116 mg, 0.20 mmol, 0.1 mmol) and Cs$_2$CO$_3$ (1.31 g, 4.02 mmol, 2.0 eq) in dioxane (20 mL) was stirred at 110° C. for 16 h under Ar. The reaction was monitored by LC-MS. The mixture was partitioned between DCM/water. The organic phase was separated, dried over Na$_2$SO$_4$, filtered and concentrated. The residue was purified by flash chromatography on silica gel (eluent: PE/EA=3:1) to give the title compound (0.7 g, 83%) as a yellow solid.

LC-MS: [M+H]$^+$ (m/z)=419.0.

Step 3: methyl 2-(2-((3-amino-4-(trifluoromethyl)phenyl)amino)pyrimidin-4-yl)benzoate A mixture of methyl 2-(2-((3-nitro-4-(trifluoromethyl)phenyl)amino)pyrimidin-4-yl)benzoate (50 mg, 0.12 mmol, 1.0 eq), and Pd/C (50 mg) in MeOH (5 mL) was stirred at RT for 3 h under H$_2$. The reaction was monitored by LC-MS. The mixture was filtered, and the filtrate was purified by flash chromatography on silica gel (eluent: PE/EA=3:1) to give the title compound (30 mg, 65%) as a yellow solid. LC-MS: [M+H]$^+$ (m/z)=389.4.

Step 1: 2-(2-chloropyrimidin-4-yl)phenol

A mixture of (2-hydroxyphenyl)boronic acid (2.0 g, 14.5 mmol, 1.0 eq), 2,4-dichloropyrimidine (2.16 g, 14.5 mmol, 1.0 eq), Pd(dppf)Cl$_2$ (1.03 mg, 1.45 mmol, 0.1 eq) and Na$_2$CO$_3$ (3.08 g, 29.0 mmol, 2.0 eq) in dioxane/H$_2$O (25 mL/2.5 mL) was stirred at 90° C. overnight under Ar. The reaction was monitored by LCMS. The mixture was filtered, and the filtrate was concentrated and purified by flash chromatography on silica gel (PE:EA=5:1) to give the title compound (800 mg, 27%) as a yellow solid. LC-MS: [M+H]$^+$ (m/z)=207.1.

Step 2: 2-(2-((4-aminophenyl)amino)pyrimidin-4-yl)phenol

A mixture of 2-(2-chloropyrimidin-4-yl)phenol (150 mg, 0.73 mmol, 1.0 eq), benzene-1,4-diamine (78 mg, 0.73 mmol, 1.0 eq), Pd(OAc)$_2$ (17 mg, 0.07 mmol, 0.1 eq), Xantphos (42 mg, 0.07 mmol, 0.1 eq) and Cs$_2$CO$_3$ (466 mg, 1.43 mmol, 2.0 eq) in dioxane (2 mL) was stirred at 110° C. for 3 h under Ar. The reaction was monitored by LCMS. The mixture was filtered, and the filtrate was concentrated and purified by prep-HPLC (CH$_3$CN/H$_2$O/0.1% NH$_3$·H$_2$O) to give the title compound (27.5 mg, 14%) as a yellow solid. LC-MS: [M+H]$^+$ (m/z)=279.1; $^1$H NMR (400 MHz, DMSO-d6) δ 9.38 (s, 1H), 8.46 (d, J=5.6 Hz, 1H), 7.96 (dd, J=8.0, 1.6 Hz, 1H), 7.37-7.32 (m, 2H), 7.14 (s, 2H), 6.91 (d, J=7.6 Hz, 1H), 6.89 (d, J=7.6 Hz, 1H), 6.57 (d, J=8.8 Hz, 2H), 4.93 (s, 2H).

Example 26: 2-(2-((3-aminophenyl)amino)pyrimidin-4-yl)phenol

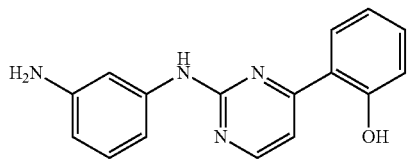 [SMILES: Nc1cccc(Nc2nccc(-c3ccccc3O)n2)c1]

Example 26 was prepared following the procedure for example 25, by replacing benzene-1,4-diamine with benzene-1,3-diamine in step 2.

The crude product was purified by prep-HPLC (MeCN/H$_2$O/0.1% NH$_3$·H$_2$O) to give the title compound (29.0 mg, 11%) as a white solid. LC-MS: [M+H]$^+$ (m/z)=279.1; $^1$H NMR (400 MHz, DMSO-d6) δ 9.67 (s, 1H), 8.53 (d, J=5.2 Hz, 1H), 8.00 (dd, J=8.4, 1.6 Hz, 1H), 7.45 (d, J=5.6 Hz, 1H), 7.40-7.35 (m, 1H), 6.98-6.88 (m, 4H), 6.80 (d, J=7.6 Hz, 1H), 6.27 (dd, J=7.6, 1.6 Hz, 1H), 5.04 (s, 2H).

Example 27: (E)-2-hydroxy-5-((3-(2-((4-(trifluoromethyl)phenyl)amino)pyrimidin-4-yl)phenyl)diazenyl)benzoic acid

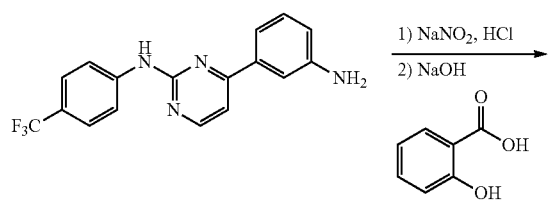

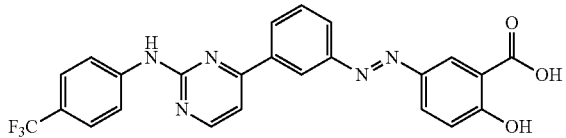

At 0° C., to a mixture of 4-(3-aminophenyl)-N-(4-(trifluoromethyl)phenyl)pyrimidin-2-amine (example 2, 100 mg, 0.3 mmol, 1.0 eq) and conc. HCl (0.5 mL) in THF (2.0 mL)/H$_2$O (6.0 mL), was added a solution of NaNO$_2$ (22 mg, 0.32 mmol, 1.05 eq) in H$_2$O. The mixture was stirred for 20 min at 0° C. The obtained solution was added to a pre-cooled solution of 2-hydroxybenzoic acid (50 mg, 0.36 mmol, 1.2 eq) in 10% aq. NaOH (10 mL) at 0° C. The resulting mixture was stirred at RT for 2 h. The reaction was monitored by LC-MS. The residue was purified by prep-HPLC (mobile phase: CH$_3$CN/H$_2$O/0.1% NH$_3$—H$_2$O) to give the title compound (40.25 mg, 28%) as a yellow solid. LC-MS: [M−H]$^-$ (m/z)=477.9; $^1$H NMR (400 MHz, CD$_3$OD) δ 8.67 (s, 1H), 8.59 (d, J=5.6 Hz, 1H), 8.54 (d, J=2.8 Hz, 1H), 8.28 (d, J=7.6 Hz, 1H), 8.04-8.00 (m, 3H), 7.98 (dd, J=8.8, 2.4 Hz, 1H), 7.69 (t, J=8.0 Hz, 1H), 7.61 (d, J=8.8 Hz, 2H), 7.50 (d, J=5.2 Hz, 1H), 6.96 (d, J=8.8 Hz, 1H).

Example 28: (E)-4-((3-carboxy-4-hydroxyphenyl)diazenyl)-2-(2-((4-(trifluoromethyl)phenyl)amino)pyrimidin-4-yl)benzoic acid

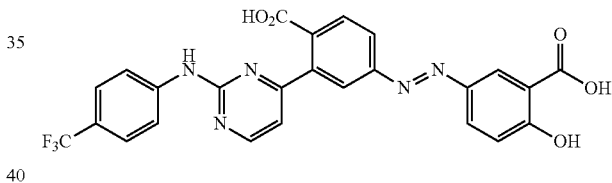

Example 28 was prepared following the procedure for example 27 by replacing 4-(3-aminophenyl)-N-(4-(trifluoromethyl)phenyl)pyrimidin-2-amine (example 2) with 4-amino-2-(2-((4-(trifluoromethyl)phenyl)amino)pyrimidin-4-yl)benzoic acid (example 7).

The residue was purified by prep-HPLC (mobile phase: CH$_3$CN/H$_2$O/0.1% NH$_3$—H$_2$O) to give the title compound (5.4 mg, 4.6%) as a yellow solid. LC-MS: [M−H]$^-$ (m/z)=522.1; $^1$H NMR (400 MHz, CD$_3$OD) δ 8.53-8.48 (m, 2H), 8.18 (d, J=2.0 Hz, 1H), 8.01-7.93 (m, 4H), 7.70 (d, J=8.0 Hz, 1H), 7.56 (d, J=8.8 Hz, 2H), 7.29 (d, J=5.2 Hz, 1H), 6.94 (d, J=8.8 Hz, 1H).

Example 29: (E)-5-((4-(carboxymethyl)-3-(2-((4-(trifluoromethyl)phenyl)amino)pyrimidin-4-yl)phenyl)diazenyl)-2-hydroxybenzoic acid

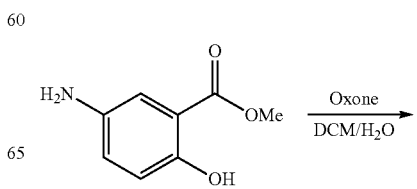

-continued

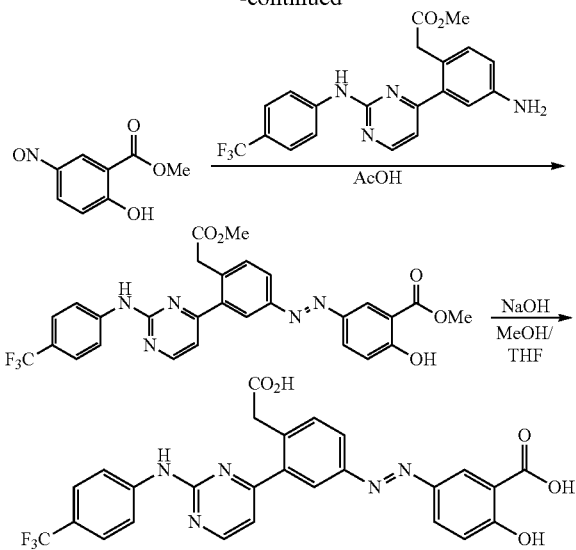

Step 1: methyl 2-hydroxy-5-nitrosobenzoate

To a solution of methyl 5-amino-2-hydroxybenzoate (100 mg, 0.6 mmol, 1.0 eq) in DCM (3 mL) was added dropwise a solution of Oxone (405 mg, 0.66 mmol, 1.1 eq) in $H_2O$ (3 mL). The mixture was stirred at RT for 2 h. The reaction was monitored by LC-MS. The organic layer was separated, dried over $Na_2SO_4$ and concentrated. The residue was purified by flash chromatography on silica gel (eluent: PE/EA=5:1) to give the title compound (87 mg, 79%) as a green solid. LC-MS: $[M+H]^+$ (m/z)=182.0.

Step 2: methyl (E)-2-hydroxy-5-((4-(2-methoxy-2-oxoethyl)-3-(2-((4-(trifluoromethyl)phenyl)amino)pyrimidin-4-yl)phenyl)diazenyl)benzoate A mixture of methyl 2-(4-amino-2-(2-((4-(trifluoromethyl)phenyl)amino)pyrimidin-4-yl)phenyl)acetate (ester precursor in final step of example 10, 100 mg, 0.25 mmol, 1.0 eq), methyl 2-hydroxy-5-nitrosobenzoate (60 mg, 0.33 mmol, 1.3 eq) in AcOH (5 mL) was stirred at 55° C. for 16 h. The reaction was monitored by LC-MS. The mixture was filtered, and the solid cake was washed with water. The solid was collected and dried under vacuum to give the title compound (105 mg, 74%) as a red solid. LC-MS: $[M+H]^+$ (m/z)=566.2.

Step 3: (E)-5-((4-(carboxymethyl)-3-(2-((4-(trifluoromethyl)phenyl)amino)pyrimidin-4-yl)phenyl)diazenyl)-2-hydroxybenzoic acid To a solution of methyl (E)-2-hydroxy-5-((4-(2-methoxy-2-oxoethyl)-3-(2-((4-(trifluoromethyl)phenyl)amino)pyrimidin-4-yl)phenyl)diazenyl)benzoate (105 mg, 0.19 mmol, 1.0 eq) in MeOH (3 mL)/THF (2 mL) was added 4 N NaOH (1.0 mL). The mixture was stirred at 50° C. for 2 h. The reaction was monitored by LC-MS. The mixture was purified by prep-HPLC (mobile phase: $CH_3CN/H_2O/0.1\%$ $NH_3$—$H_2O$) to give the title compound (84.5 mg, 83%) as a yellow solid. LC-MS: $[M-H]^-$ (m/z)=535.9; $^1H$ NMR (400 MHz, DMSO-d6) δ 10.17 (s, 1H), 8.60 (d, J=5.2 Hz, 1H), 8.26 (d, J=2.4 Hz, 1H), 8.06 (d, J=8.8 Hz, 2H), 7.98 (d, J=1.6 Hz, 1H), 7.85-7.75 (m, 2H), 7.67-7.62 (m, 3H), 7.55 (d, J=8.0 Hz, 1H), 6.74 (d, J=8.8 Hz, 1H), 3.49 (s, 2H).

Example 30: (E)-4,4'-(diazene-1,2-diylbis(3,1-phenylene))bis(N-(4-(trifluoromethyl)phenyl)pyrimidin-2-amine)

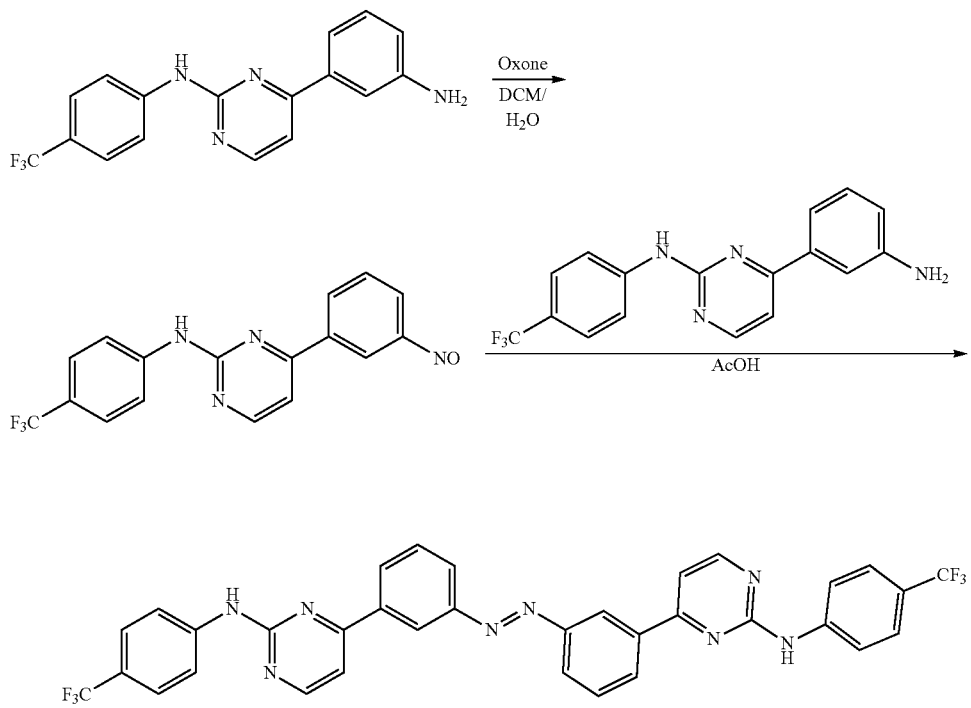

Step 1: 4-(3-nitrosophenyl)-N-(4-(trifluoromethyl)phenyl)pyrimidin-2-amine

To a solution of 4-(3-aminophenyl)-N-(4-(trifluoromethyl)phenyl)pyrimidin-2-amine (example 2, 300 mg, 0.91 mmol, 1.0 eq) in DCM (30 mL) was added dropwise a solution of Oxone (726 mg, 1.18 mmol, 1.3 eq) in $H_2O$ (30 mL). The mixture was stirred at RT for 2 h. The reaction was monitored by LC-MS. The residue was purified by flash chromatography on silica gel (PE/EA=5:1) to give the title compound (125 mg, 40%) as a yellow solid. LC-MS: [M+H]+(m/z)=345.1.

Step 2: (E)-4,4'-(diazene-1,2-diylbis(3,1-phenylene))bis(N-(4-(trifluoromethyl)phenyl)pyrimidin-2-amine)

To a solution of 4-(3-nitrosophenyl)-N-(4-(trifluoromethyl)phenyl)pyrimidin-2-amine (94 mg, 0.27 mmol, 1.0 eq) in AcOH (20 mL) was added 4-(3-aminophenyl)-N-(4-(trifluoromethyl)phenyl)pyrimidin-2-amine (example 2, 90 mg, 0.27 mmol, 1.0 eq). The mixture was stirred at RT for 16 h. The reaction was monitored by LC-MS. The residue was purified by prep-HPLC (mobile phase: $CH_3CN/H_2O$/0.1% $NH_3$—$H_2O$) to give the title compound (11.15 mg, 6%) as a yellow solid. LC-MS: [M−H]⁻ (m/z)=654.9; ¹H NMR (400 MHz, DMSO-d6) δ 10.23 (s, 2H), 8.77 (s, 2H), 8.71-8.70 (m, 2H), 8.43 (d, J=7.6 Hz, 2H), 8.15 (d, J=7.6 Hz, 2H), 8.09 (d, J=8.0 Hz, 4H), 7.85 (t, J=7.6 Hz, 2H), 7.68-7.66 (m, 6H).

Example 31: (E)-4,4'-(diazene-1,2-diylbis(2,1-phenylene))bis(N-(4-(trifluoromethyl)phenyl)pyrimidin-2-amine)

Step 1: 4-(2-nitrosophenyl)-N-(4-(trifluoromethyl)phenyl)pyrimidin-2-amine

To a solution of 4-(2-aminophenyl)-N-(4-(trifluoromethyl)phenyl)pyrimidin-2-amine (example 3, 200 mg, 0.61 mmol, 1.0 eq) in DCM (15.0 mL) was added a solution of Oxone (446 mg, 0.73 mmol, 1.2 eq) in $H_2O$ (15.0 mL). The mixture was stirred at RT for 2 h. The reaction was monitored by LC-MS. The residue was purified by flash chromatography on silica gel (PE/EA=5:1) to give the title compound (140 mg, 67%) as a yellow solid. LC-MS: [M+H]+(m/z)=345.1.

Step 2: (E)-4,4'-(diazene-1,2-diylbis(2,1-phenylene))bis(N-(4-(trifluoromethyl)phenyl)pyrimidin-2-amine)

To a solution of 4-(2-nitrosophenyl)-N-(4-(trifluoromethyl)phenyl)pyrimidin-2-amine (140 mg, 0.42 mmol, 1.0 eq) in HOAc (20 mL) was added 4-(2-aminophenyl)-N-(4-(trifluoromethyl)phenyl)pyrimidin-2-amine (example 3, 70 mg, 0.42 mmol, 1.0 eq). The mixture was stirred at RT for 16 h. The reaction was monitored by LC-MS. The crude product was purified by prep-HPLC (mobile phase: $CH_3CN/H_2O$/0.1% $NH_3$—$H_2O$), freeze-dried to give the title compound (89.6 mg, 33%) as a yellow solid. LC-MS: [M−H]⁻ (m/z)=654.9; ¹H NMR (400 MHz, DMSO-d6) δ 10.21 (s, 2H), 8.63 (d, J=5.2 Hz, 2H), 7.98 (d, J=8.4 Hz, 4H), 7.93 (d, J=7.6 Hz, 2H), 7.69 (t, J=7.6 Hz, 2H), 7.57 (t, J=7.2 Hz, 2H), 7.53-7.50 (m, 6H), 7.16 (d, J=5.2 Hz, 2H).

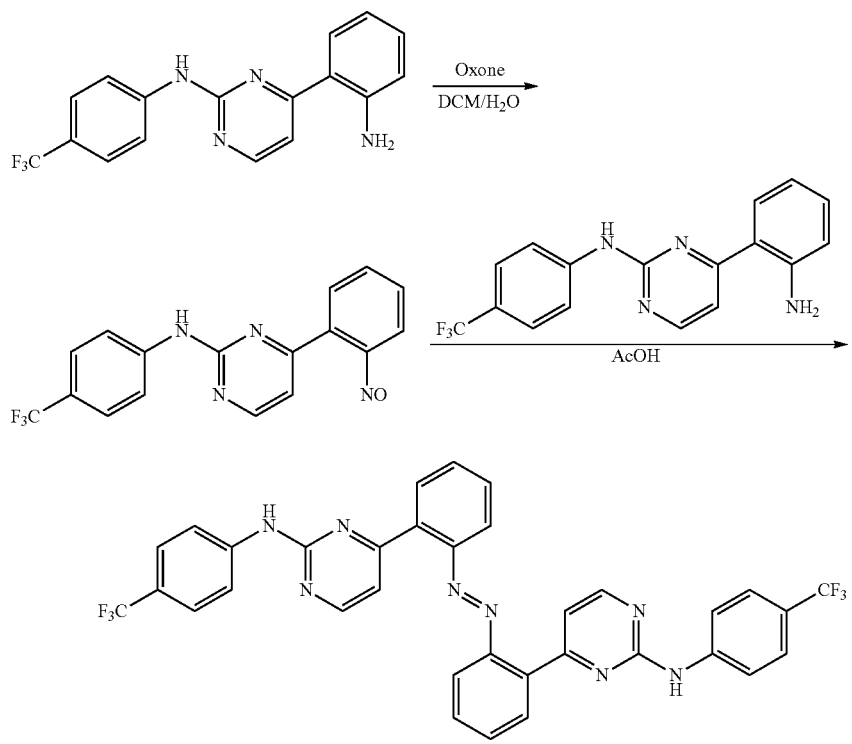

Example 32: (E)-2-hydroxy-5-((2-(2-((4-(trifluoromethyl)phenyl)amino)pyrimidin-4-yl)phenyl)diazenyl)benzoic acid

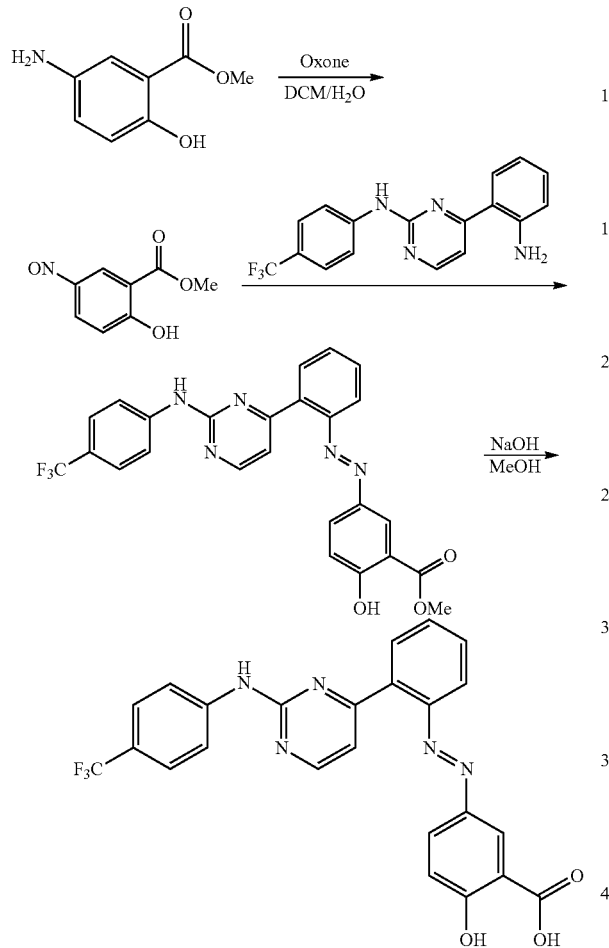

Step 1: methyl 2-hydroxy-5-nitrosobenzoate

To a solution of methyl 5-amino-2-hydroxybenzoate (100 mg, 0.6 mmol, 1.0 eq) in DCM (10 mL) was added dropwise a solution of Oxone (405 mg, 0.66 mmol, 1.1 eq) in $H_2O$ (10 mL). The mixture was stirred at RT for 2 h. The reaction was monitored by LC-MS. The organic layer was separated, dried over $Na_2SO_4$ and concentrated. The residue was purified by flash chromatography on silica gel (eluent: PE/EA=5:1) to give the title compound (81 mg, 75%) as a green solid. LC-MS: [M+H]$^+$ (m/z)=182.2.

Step 2: methyl (E)-2-hydroxy-5-((2-(2-((4-(trifluoromethyl)phenyl)amino)pyrimidin-4-yl)phenyl)diazenyl)benzoate To a solution of methyl 2-hydroxy-5-nitrosobenzoate (81 mg, 0.45 mmol, 1.3 eq) in HOAc (15 mL) was added 4-(2-aminophenyl)-N-(4-(trifluoromethyl)phenyl)pyrimidin-2-amine (example 3, 100 mg, 0.3 mmol, 1.0 eq). The mixture was stirred at 45° C. for 48 h. The reaction was monitored by LC-MS. The residue was purified by prep-HPLC (mobile phase: $CH_3CN/H_2O/0.1\%$ $NH_3$—$H_2O$) to give the title compound (45 mg, 30%) as a yellow solid. LC-MS: [M+H]$^+$ (m/z)=494.0.

Step 3: (E)-2-hydroxy-5-((2-(2-((4-(trifluoromethyl)phenyl)amino)pyrimidin-4-yl)phenyl)diazenyl)benzoic acid To a solution of methyl (E)-2-hydroxy-5-((2-(2-((4-(trifluoromethyl)phenyl)amino)pyrimidin-4-yl)phenyl)diazenyl)benzoate (45 mg, 0.1 mmol, 1.0 eq) in MeOH (3.0 mL) was added NaOH (4.0 M, 1.0 mL). The mixture was stirred at 60° C. for 2 h. The reaction was monitored by LC-MS. The residue was purified by prep-HPLC (mobile phase: $CH_3CN/H_2O/0.1\%$ $NH_3$—$H_2O$) to give the title compound (33.7 mg, 78%) as a yellow solid. LC-MS: [M–H]$^-$ (m/z)=477.9; $^1$H NMR (400 MHz, DMSO-d6) δ 10.17 (s, 1H), 8.58 (d, J=5.2 Hz, 1H), 8.21 (d, J=2.4 Hz, 1H), 8.01 (d, J=8.8 Hz, 2H), 7.93 (dd, J=7.2, 2.0 Hz, 1H), 7.67-7.60 (m, 4H), 7.56 (d, J=8.8 Hz, 2H), 7.08 (d, J=5.2 Hz, 1H), 6.68 (d, J=8.8 Hz, 1H).

Example 33: (E)-4-((2-(2-((4-(trifluoromethyl)phenyl)amino)pyrimidin-4-yl)phenyl)diazenyl)phenol

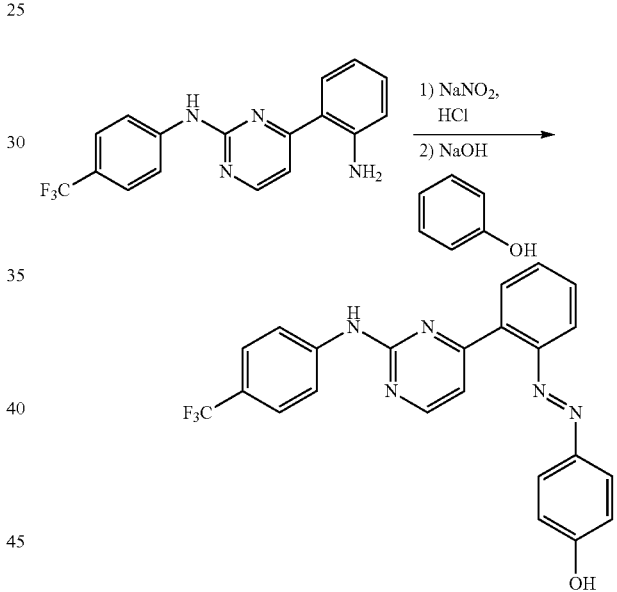

At 0° C., to a mixture of 4-(2-aminophenyl)-N-(4-(trifluoromethyl)phenyl)pyrimidin-2-amine (example 3, 50 mg, 0.15 mmol, 1.0 eq) in 6M HCl (3.0 mL) was added a solution of $NaNO_2$ (21 mg, 0.3 mmol, 2.0 eq) in $H_2O$. The mixture was stirred for 30 min at 0° C. The obtained solution was added to a pre-cooled solution of phenol (14.3 mg, 0.15 mmol, 1.0 eq) in 10% aq. NaOH (1 mL) at 0° C., and the pH of the mixture was adjusted to 7-8 with 10% aq. NaOH. The resulting mixture was stirred at RT for 2 h. The reaction was monitored by LC-MS. The mixture was extracted with EA. The combined organic layer was dried over $Na_2SO_4$ and concentrated. The residue was purified by prep-HPLC (mobile phase: $CH_3CN/H_2O/0.1\%$ $NH_3$—$H_2O$) to give the title compound (7.5 mg, 11%) as a yellow solid. LC-MS: [M+H]$^+$ (m/z)=436.1; $^1$H NMR (400 MHz, DMSO-d6) δ 10.19 (s, 1H), 8.61 (d, J=4.8 Hz, 1H), 7.98 (d, J=8.4 Hz, 2H), 7.94-7.91 (m, 1H), 7.68 (dd, J=17.5, 6.0 Hz, 5H), 7.53 (d, J=8.4 Hz, 2H), 7.10 (d, J=4.8 Hz, 1H), 6.89 (d, J=8.8 Hz, 2H).

Example 34: (E)-3-((2-(2-((4-(trifluoromethyl)phenyl)amino)pyrimidin-4-yl)phenyl)diazenyl)benzoic acid

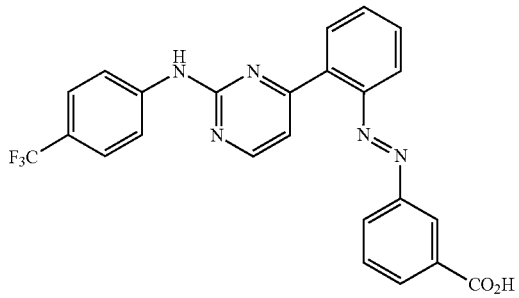 [SMILES: O=C(O)c1cccc(/N=N/c2ccccc2-c2ccnc(Nc3ccc(C(F)(F)F)cc3)n2)c1]

Example 34 was prepared following the procedure for example 32, by replacing methyl 5-amino-2-hydroxybenzoate with methyl 3-aminobenzoate in step 1.

The crude product was purified by prep-HPLC (mobile phase: $CH_3CN/H_2O/0.1\%$ $NH_3$—$H_2O$) to give the title compound (58.7 mg, 60%) as a yellow solid. LC-MS: $[M+H]^+$ (m/z)=464.0; $^1H$ NMR (400 MHz, DMSO-d6) δ 10.21 (s, 1H), 8.60 (d, J=4.8 Hz, 1H), 8.30 (s, 1H), 8.02-7.98 (m, 4H), 7.74-7.69 (m, 4H), 7.55 (d, J=8.8 Hz, 2H), 7.43 (t, J=7.6 Hz, 1H), 7.08 (d, J=5.2 Hz, 1H).

Example 35: (E)-4-((2-(2-((4-(trifluoromethyl)phenyl)amino)pyrimidin-4-yl)phenyl)diazenyl)benzoic acid

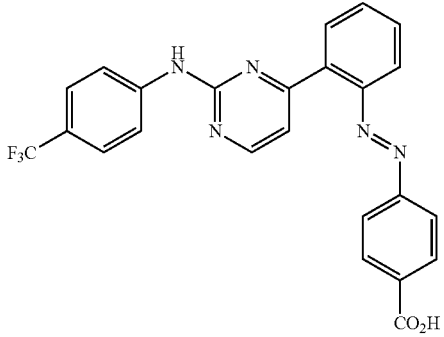 [SMILES: O=C(O)c1ccc(/N=N/c2ccccc2-c2ccnc(Nc3ccc(C(F)(F)F)cc3)n2)cc1]

Example 35 was prepared following the procedure for example 32, by replacing methyl 5-amino-2-hydroxybenzoate with methyl 4-aminobenzoate in step 1.

The crude product was purified by prep-HPLC (mobile phase: $CH_3CN/H_2O/0.1\%$ FA) to give the title compound (58 mg, 28%) as a yellow solid. LC-MS: $[M+H]^+$ (m/z)=464.1; $^1H$ NMR (400 MHz, DMSO-d6) δ 10.19 (s, 1H), 8.63 (d, J=5.2 Hz, 1H), 8.07 (d, J=8.8 Hz, 2H), 7.99-7.92 (m, 3H), 7.86 (d, J=8.8 Hz, 2H), 7.81-7.69 (m, 3H), 7.49 (d, J=8.8 Hz, 2H), 7.16 (d, J=5.2 Hz, 1H).

Example 36: (E)-4-hydroxy-3-((2-(2-((4-(trifluoromethyl)phenyl)amino)pyrimidin-4-yl)phenyl)diazenyl)benzoic acid

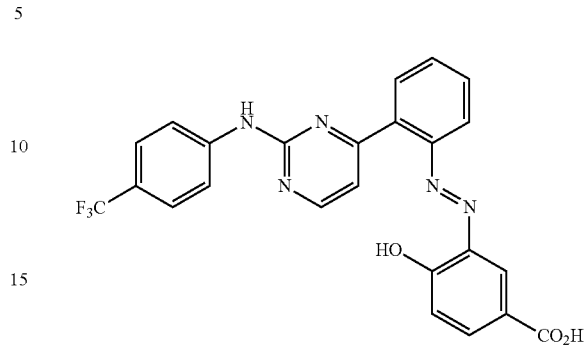

Example 36 was prepared following the procedure for example 32, by replacing methyl 5-amino-2-hydroxybenzoate with methyl 3-amino-4-hydroxybenzoate in step 1.

The crude product was purified by prep-HPLC (mobile phase: $CH_3CN/H_2O/0.1\%$ $NH_3$—$H_2O$) to give the title compound (79.4 mg, 77%) as a yellow solid. LC-MS: $[M+H]^+$ (m/z)=480.0; $^1H$ NMR (400 MHz, $CD_3OD$) δ 8.60 (d, J=5.2 Hz, 1H), 8.56 (d, J=2.0 Hz, 1H), 7.99-7.97 (m, 1H), 7.93 (dd, J=8.8, 2.0 Hz, 1H), 7.89-7.83 (m, 3H), 7.71-7.67 (m, 2H), 7.40 (d, J=8.8 Hz, 2H), 7.21 (d, J=5.2 Hz, 1H), 6.83 (d, J=8.8 Hz, 1H).

Example 37: (E)-2-hydroxy-5-((2-(2-((4-(trifluoromethyl)phenyl)amino)pyrimidin-4-yl)phenyl)diazenyl)isophthalic acid

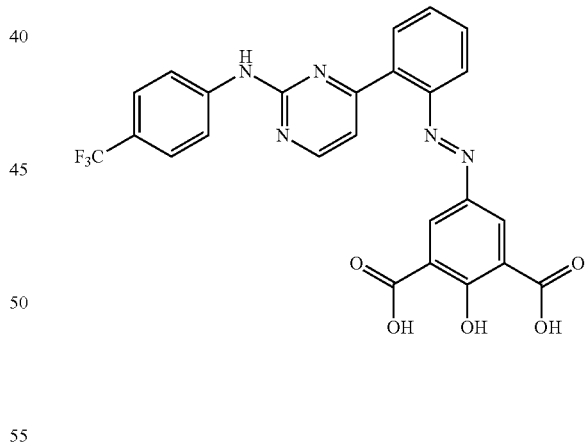

Example 37 was prepared following the procedure for example 33, by replacing phenol with dimethyl 2-hydroxyisophthalate, then followed by hydrolysis with NaOH.

The crude product was purified by prep-HPLC (mobile phase: $CH_3CN/H_2O/0.1\%$ $NH_3$—$H_2O$) to give the title compound (40.31 mg, 51%) as a yellow solid. LC-MS: $[M+H]^+$ (m/z)=524.2; $^1H$ NMR (400 MHz, $CD_3OD$) δ 8.54 (s, 2H), 8.52 (d, J=5.2 Hz, 1H), 7.98-7.96 (m, 1H), 7.89 (d, J=8.8 Hz, 2H), 7.73-7.71 (m, 1H), 7.63-7.59 (m, 2H), 7.42 (d, J=8.4 Hz, 2H), 7.14 (d, J=5.2 Hz, 1H).

Example 38: (E)-5-hydroxy-2-((2-(2-((4-(trifluoromethyl)phenyl)amino)pyrimidin-4-yl)phenyl)diazenyl)benzoic acid

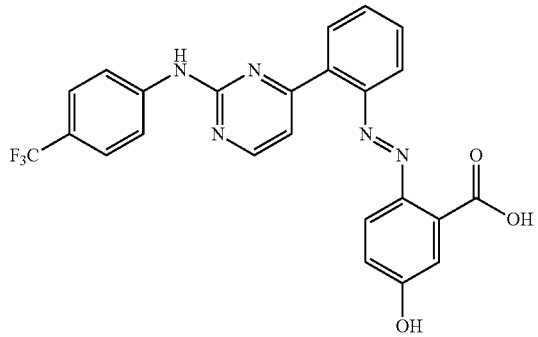 [SMILES: O=C(O)c1cc(O)ccc1/N=N/c1ccccc1-c1ccnc(Nc2ccc(C(F)(F)F)cc2)n1]

Example 38 was prepared following the procedure for example 32, by replacing methyl 5-amino-2-hydroxybenzoate with methyl 2-amino-5-hydroxybenzoate in step 1.

The residue was purified by prep-HPLC (mobile phase: $CH_3CN/H_2O/0.1\%\ NH_3-H_2O$) to give the title compound (28.56 mg, 19%) as a yellow solid. LC-MS: $[M+H]^+$ (m/z)=480.2; $^1H$ NMR (400 MHz, $CD_3OD$) δ 8.52 (d, J=5.2 Hz, 1H), 7.98-7.95 (m, 1H), 7.99 (d, J=8.8 Hz, 2H), 7.69-7.61 (m, 3H), 7.53 (d, J=8.8 Hz, 1H), 7.46 (d, J=8.4 Hz, 2H), 7.24 (d, J=2.4 Hz, 1H), 7.12 (d, J=5.2 Hz, 1H), 6.88 (dd, J=5.2, 2.8 Hz, 1H).

Example 39: (E)-2-hydroxy-4-((2-(2-((4-(trifluoromethyl)phenyl)amino)pyrimidin-4-yl)phenyl)diazenyl)benzoic acid

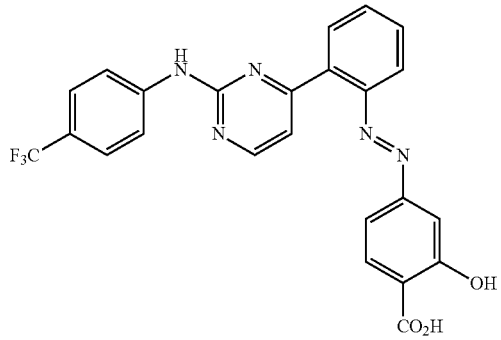 [SMILES: O=C(O)c1ccc(/N=N/c2ccccc2-c2ccnc(Nc3ccc(C(F)(F)F)cc3)n2)cc1O]

Example 39 was prepared following the procedure for example 32, by replacing methyl 5-amino-2-hydroxybenzoate with methyl 4-amino-2-hydroxybenzoate in step 1.

The residue was purified by prep-HPLC (mobile phase: $CH_3CN/H_2O/0.1\%\ NH_3-H_2O$) to give the title compound (23.4 mg, 31%) as a yellow solid. LC-MS: $[M+H]^+$ (m/z)=480.1; $^1H$ NMR (400 MHz, DMSO-d6) δ 10.20 (s, 1H), 8.62 (d, J=5.2 Hz, 1H), 8.02-7.93 (m, 3H), 7.79 (d, J=8.4 Hz, 1H), 7.72-7.67 (m, 3H), 7.57 (d, J=8.8 Hz, 2H), 7.10-7.06 (m, 2H), 6.98 (d, J=2.0 Hz, 1H).

Example 40: (E)-3-hydroxy-4-((2-(2-((4-(trifluoromethyl)phenyl)amino)pyrimidin-4-yl)phenyl)diazenyl)benzoic acid

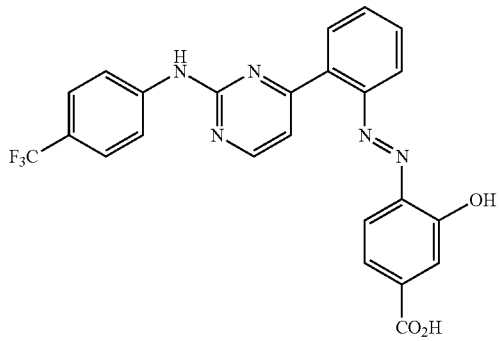 [SMILES: O=C(O)c1ccc(/N=N/c2ccccc2-c2ccnc(Nc3ccc(C(F)(F)F)cc3)n2)c(O)c1]

Example 40 was prepared following the procedure for example 32, by replacing methyl 5-amino-2-hydroxybenzoate with methyl 4-amino-3-hydroxybenzoate in step 1.

The residue was purified by prep-HPLC (mobile phase: $CH_3CN/H_2O/0.1\%\ NH_3-H_2O$) to give the title compound (33 mg, 43%) as a yellow solid. LC-MS: $[M+H]^+$ (m/z)=480.2; $^1H$ NMR (400 MHz, DMSO-d6) δ 10.17 (s, 1H), 8.65 (d, J=5.2 Hz, 1H), 7.98-7.92 (m, 3H), 7.91-7.86 (m, 1H), 7.77-7.69 (m, 2H), 7.57 (d, J=8.4 Hz, 1H), 7.53-7.47 (m, 3H), 7.42 (dd, J=8.4, 1.6 Hz, 1H), 7.21 (d, J=5.2 Hz, 1H).

Example 41: (E)-4-methoxy-3-((2-(2-((4-(trifluoromethyl)phenyl)amino)pyrimidin-4-yl)phenyl)diazenyl)benzoic acid

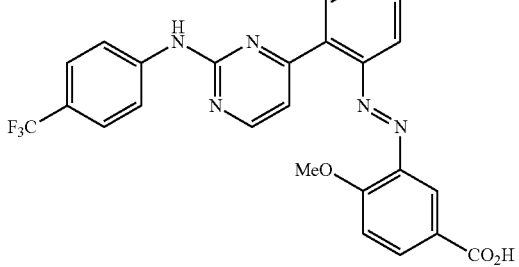

Example 41 was prepared following the procedure for example 32, by replacing methyl 5-amino-2-hydroxybenzoate with methyl 3-amino-4-methoxybenzoate in step 1.

The residue was purified by prep-HPLC (mobile phase: $CH_3CN/H_2O/0.1\%\ NH_3-H_2O$) to give the title compound (21.4 mg, 36%) as a yellow solid. LC-MS: $[M+H]^+$ (m/z)=494.1; $^1H$ NMR (400 MHz, DMSO-d6) δ 10.16 (s, 1H), 8.59 (d, J=5.2 Hz, 1H), 8.01 (dd, J=8.4, 2.0 Hz, 1H), 7.97-7.93 (m, 3H), 7.88 (d, J=2.0 Hz, 1H), 7.71-7.66 (m, 2H), 7.59-7.56 (m, 1H), 7.52 (d, J=8.8 Hz, 2H), 7.19 (d, J=8.4 Hz, 1H), 7.10 (d, J=4.8 Hz, 1H), 3.99 (s, 3H).

Example 42: (E)-2-methoxy-4-((2-(2-((4-(trifluoromethyl)phenyl)amino)pyrimidin-4-yl)phenyl)diazenyl)benzoic acid

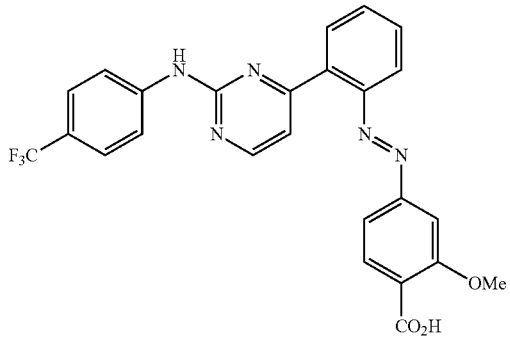 [SMILES: COc1cc(/N=N/c2ccccc2-c2ccnc(Nc3ccc(C(F)(F)F)cc3)n2)ccc1C(=O)O]

Example 42 was prepared following the procedure for example 32, by replacing methyl 5-amino-2-hydroxybenzoate with methyl 4-amino-2-methoxybenzoate in step 1.

The residue was purified by prep-HPLC (mobile phase: $CH_3CN/H_2O/0.1\%$ $NH_3$—$H_2O$) to give the title compound (27.5 mg, 33%) as a yellow solid. LC-MS: $[M+H]^+$ (m/z)=494.1; $^1H$ NMR (400 MHz, DMSO-d6) δ 10.20 (s, 1H), 8.64 (d, J=4.8 Hz, 1H), 8.01-7.96 (m, 3H), 7.81-7.70 (m, 4H), 7.55 (d, J=8.8 Hz, 2H), 7.50-7.35 (m, 2H), 7.17 (d, J=4.8 Hz, 1H), 3.80 (s, 3H).

Example 43: (E)-2-methoxy-5-((2-(2-((4-(trifluoromethyl)phenyl)amino)pyrimidin-4-yl)phenyl)diazenyl)benzoic acid

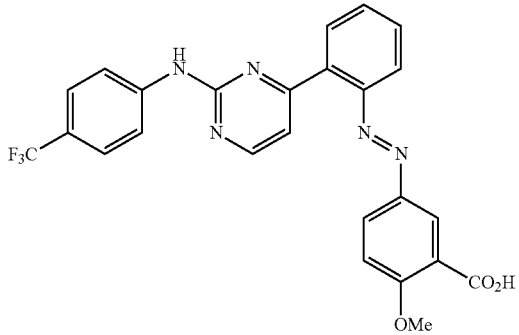 [SMILES: COc1ccc(/N=N/c2ccccc2-c2ccnc(Nc3ccc(C(F)(F)F)cc3)n2)cc1C(=O)O]

Example 43 was prepared following the procedure for example 32, by replacing methyl 5-amino-2-hydroxybenzoate with methyl 5-amino-2-methoxybenzoate in step 1.

The residue was purified by prep-HPLC (mobile phase: $CH_3CN/H_2O/0.1\%$ $NH_3$—$H_2O$) to give the title compound (127.8 mg, 32%) as a yellow solid. LC-MS: $[M+H]^+$ (m/z)=494.0; $^1H$ NMR (400 MHz, DMSO-d6) δ 10.20 (s, 1H), 8.57 (d, J=5.2 Hz, 1H), 8.02 (d, J=8.8 Hz, 2H), 7.96-7.92 (m, 1H), 7.68-7.57 (m, 7H), 7.04-7.01 (m, 2H), 3.78 (s, 3H).

Example 44: (E)-4-(trifluoromethoxy)-3-((2-(2-((4-(trifluoromethyl)phenyl)amino)pyrimidin-4-yl)phenyl)diazenyl)benzoic acid

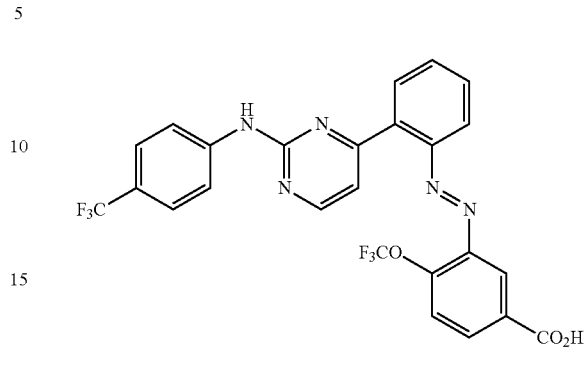

Example 44 was prepared following the procedure for example 32, by replacing methyl 5-amino-2-hydroxybenzoate with methyl 3-amino-4-(trifluoromethoxy)benzoate in step 1. The mixture was purified by prep-HPLC (mobile phase: $CH_3CN/H_2O/0.1\%$ $NH_3$—$H_2O$) to give the title compound (108 mg, 65%) as a yellow solid. LC-MS: $[M+H]^+$ (m/z)=548.2; $^1H$ NMR (400 MHz, DMSO-d6) δ 10.19 (s, 1H), 8.59 (d, J=5.2 Hz, 1H), 8.10 (dd, J=8.4, 2.0 Hz, 1H), 8.01 (d, J=2.0 Hz, 1H), 7.98 (dd, J=7.6, 2.0 Hz, 1H), 7.94 (d, J=8.8 Hz, 2H), 7.79-7.72 (m, 2H), 7.64-7.62 (m, 1H), 7.55-7.47 (m, 1H), 7.49 (d, J=8.0 H, 2H), 7.11 (d, J=4.8 Hz, 1H).

Example 45: (E)-4-ethoxy-3-((2-(2-((4-(trifluoromethyl)phenyl)amino)pyrimidin-4-yl)phenyl)diazenyl) benzoic acid

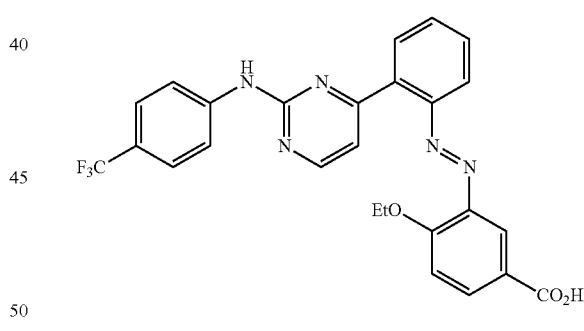

Example 45 was prepared following the procedure for example 32, by replacing methyl 5-amino-2-hydroxybenzoate with methyl 3-amino-4-ethoxybenzoate in step 1.

The mixture was purified by prep-HPLC (mobile phase: $CH_3CN/H_2O/0.1\%$ $NH_3$—$H_2O$) to give the title compound (46.7 mg, 48%) as a yellow solid. LC-MS: $[M+H]^+$ (m/z)=508.2; $^1H$ NMR (400 MHz, DMSO-d6) δ 10.17 (s, 1H), 8.58 (d, J=5.2 Hz, 1H), 8.02 (dd, J=8.8, 2.4 Hz, 1H), 7.96-7.85 (m, 4H), 7.71 (dt, J=11.2, 3.7 Hz, 2H), 7.64-7.58 (m, 1H), 7.50 (d, J=8.8 Hz, 2H), 7.35 (d, J=8.8 Hz, 1H), 7.12 (d, J=4.8 Hz, 1H), 4.35 (q, J=6.8 Hz, 2H), 1.45 (t, J=6.8 Hz, 3H).

Example 46: (E)-2-hydroxy-5-((2-(2-((4-(trifluoromethyl)phenyl)amino)pyrimidin-4-yl)phenyl)diazenyl)benzonitrile

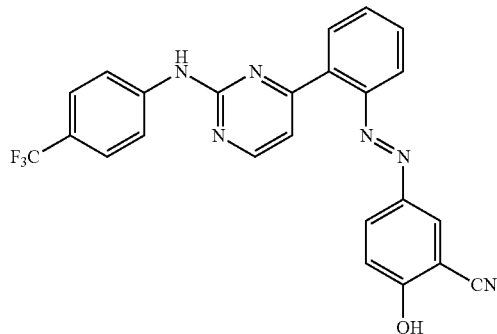 [SMILES: N#Cc1cc(/N=N/c2ccccc2-c2ccnc(Nc3ccc(C(F)(F)F)cc3)n2)ccc1O]

Example 46 was prepared following procedure for example 33, by replacing phenol with 2-hydroxybenzonitrile. The residue was purified by prep-HPLC (mobile phase: CH$_3$CN/H$_2$O/0.1% NH$_3$—H$_2$O) to give the title compound (69.5 mg, 50%) as a yellow solid. LC-MS: [M+H]$^+$ (m/z)=461.0; $^1$H NMR (400 MHz, CD$_3$OD) δ 8.53 (d, J=5.2 Hz, 1H), 7.97-7.93 (m, 2H), 7.89-7.85 (m, 3H), 7.72-7.70 (m, 1H), 7.65-7.62 (m, 2H), 7.40 (d, J=8.8 Hz, 2H), 7.12 (d, J=4.8 Hz, 1H), 6.98 (d, J=9.2 Hz, 1H).

Example 47: (E)-(2-hydroxy-5-((2-(2-((4-(trifluoromethyl)phenyl)amino)pyrimidin-4-yl)phenyl)diazenyl)phenyl)phosphonic acid

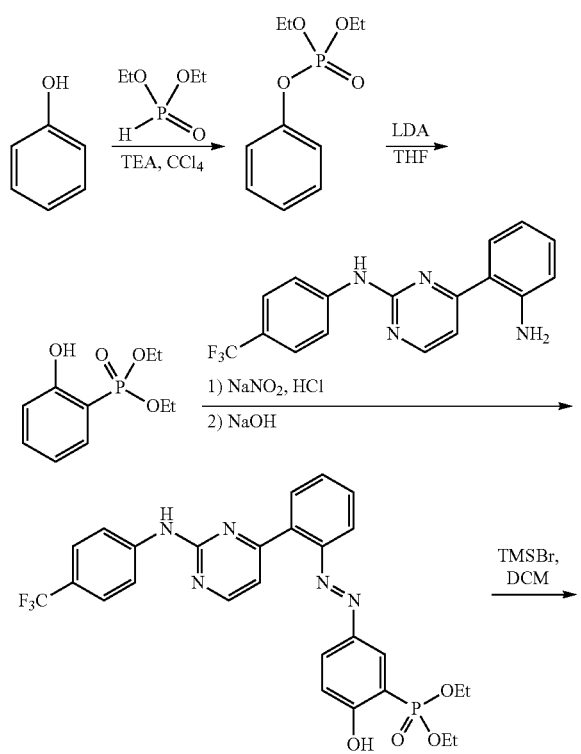

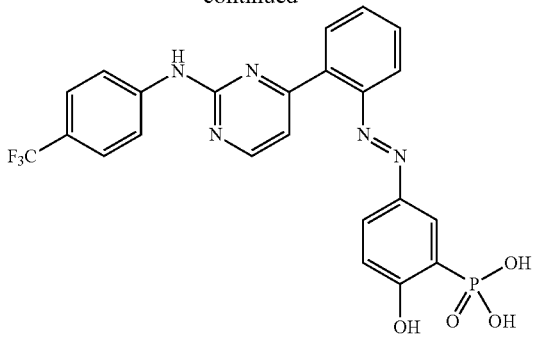

Step 1: diethyl phenyl phosphate

At 0° C., to a mixture of phenol (1.0 g, 10.64 mmol, 1.0 eq) and TEA (1.55 mL, 11.17 mmol, 1.05 eq) in CCl$_4$ (10 mL) was added HP(O)(OEt)$_2$ (17 mg, 0.14 mmol, 1.2 eq) under Ar. The mixture was stirred overnight at RT. The mixture was filtered, and the filtrate was concentrated and purified by flash chromatography on silica gel (eluent: PE:EA=100:1 to 5:1) to give the title compound (1.8 g, 74%). LC-MS: [M+H]$^+$ (m/z)=231.1.

Step 2: diethyl (2-hydroxyphenyl)phosphonate

Diethyl phenyl phosphate (0.5 g, 2.2 mmol, 1.0 eq) in THF was added to LDA (1.1 mL, 2.2 mmol, 1.0 eq) at −78° C. under Ar. The resulting mixture was stirred at −78° C. for 1 h and then at 0° C. for 5 h. The reaction was monitored by LC-MS. The reaction was quenched with sat. NH$_4$Cl, extracted with Et$_2$O. The organic phase was dried over Na$_2$SO$_4$, filtered and concentrated to give the title compound (468 mg, 94%) as a yellow solid. LC-MS: M+H]$^+$ (m/z)=231.1.

Step 3: diethyl (E)-(2-hydroxy-5-((2-(2-((4-(trifluoromethyl)phenyl)amino)pyrimidin-4-yl)phenyl)diazenyl)phenyl)phosphonate At 0° C., to a solution 4-(2-aminophenyl)-N-(4-(trifluoromethyl)phenyl)pyrimidin-2-amine (100 mg, 0.3 mmol, 1.0 eq) in 6M HCl (4 mL) was added NaNO$_2$ (42 mg, 0.61 mmol, 2.0 eq) in H$_2$O (7 mL). The mixture stirred for 0.5 h at 0° C., and then was added a solution of diethyl (2-hydroxyphenyl)phosphonate in 2N NaOH (14 mL). The pH was adjusted to 8 with 2N NaOH, and the resulting mixture was stirred for 1 h at 0° C. The mixture was adjusted to pH 7 and then filtered. The filter cake was dried under vacuum to give the title compound (60 mg, 35%) as yellow solid. LC-MS: [M+H]$^+$ (m/z)=572.2.

Step 4: (E)-(2-hydroxy-5-((2-(2-((4-(trifluoromethyl)phenyl)amino)pyrimidin-4-yl)phenyl)diazenyl)phenyl)phosphonic acid To a solution of diethyl (E)-(2-hydroxy-5-((2-(2-((4-(trifluoromethyl)phenyl)amino)pyrimidin-4-yl)phenyl)diazenyl)phenyl)phosphonate (60 mg, 0.10 mmol, 1.0 eq) in DCM (3 mL) was added TMSBr (3 mL). The mixture was stirred at 35° C. for 2 h under Ar. The reaction was monitored by LC-MS. The reaction solution was concentrated to dryness under reduced pressure. The residue was purified by prep-HPLC to give the title compound (22.3 mg, 43%) as a yellow powder. LC-MS: [M−H]⁻ (m/z)=514.2; ¹H NMR (400 MHz, DMSO-d6) δ 10.18 (s, 1H), 8.56 (d, J=5.2 Hz, 1H), 8.04 (d, J=8.8 Hz, 2H), 7.97-7.91 (m, 2H), 7.68-7.57 (m, 6H), 7.09 (s, 3H), 7.02 (d, J=5.2 Hz, 1H), 6.73 (dd, J=8.8, 4.8 Hz, 1H).

Example 48: (E)-2-(methylsulfonyl)-4-((2-(2-((4-(trifluoromethyl)phenyl)amino)pyrimidin-4-yl)phenyl)diazenyl)phenol

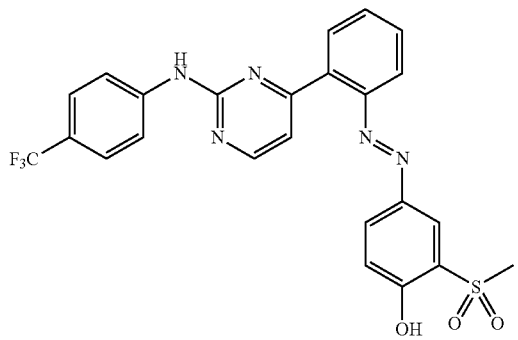 [SMILES: CS(=O)(=O)c1cc(/N=N/c2ccccc2-c2ccnc(Nc3ccc(C(F)(F)F)cc3)n2)ccc1O]

Example 48 was prepared following procedure for example 33, by replacing phenol with 2-(methylsulfonyl)phenol.

The residue was purified by prep-HPLC (mobile phase: CH₃CN/H₂O/0.1% NH₃—H₂O) to give the title compound (47.1 mg, 30%) as a yellow solid. LC-MS: [M+H]⁺ (m/z)=514.1; ¹H NMR (400 MHz, CD₃OD) δ 8.56 (d, J=5.2 Hz, 1H), 8.30 (d, J=2.4 Hz, 1H), 8.03-7.97 (m, 2H), 7.91 (d, J=8.4 Hz, 2H), 7.79-7.77 (m, 1H), 7.68-7.65 (m, 2H), 7.42 (d, J=8.8 Hz, 2H), 7.16 (d, J=5.2 Hz, 1H), 7.10 (d, J=8.8 Hz, 1H), 3.22 (m, 3H).

Example 49: (R,E)-2-amino-3-(2-hydroxy-5-((2-(2-((4-(trifluoromethyl)phenyl)amino)pyrimidin-4-yl)phenyl)diazenyl)phenyl)propanoic acid

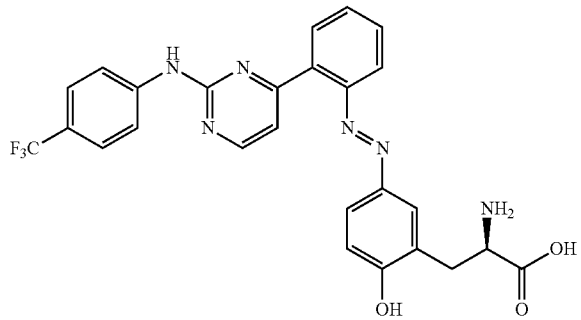 [SMILES: N[C@H](Cc1cc(/N=N/c2ccccc2-c2ccnc(Nc3ccc(C(F)(F)F)cc3)n2)ccc1O)C(=O)O]

Example 49 was prepared following procedure for example 33, by replacing phenol with methyl (R)-2-((tert-butoxycarbonyl)amino)-3-(2-hydroxyphenyl)propanoate, followed by hydrolysis and deprotection of Boc group.

The residue was purified by prep-HPLC (mobile phase: CH₃CN/H₂O/0.1% NH₃—H₂O) to give the title compound (10.78 mg, 33%) as a yellow solid. LC-MS: [M+H]⁺ (m/z)=523.2; ¹H NMR (400 MHz, CD₃OD) δ 8.52 (d, J=4.8 Hz, 1H), 7.98-7.95 (m, 1H), 7.92 (d, J=8.8 Hz, 2H), 7.76 (d, J=2.8 Hz, 1H), 7.69-7.65 (m, 2H), 7.62-7.59 (m, 2H), 7.45 (d, J=8.8 Hz, 2H), 7.08 (d, J=5.2 Hz, 1H), 6.93 (d, J=8.4 Hz, 1H), 3.90 (dd, J=8.8, 4.4 Hz, 1H), 3.41 (dd, J=14.4, 4.4 Hz, 1H), 2.99 (dd, J=14.4, 8.4 Hz, 1H).

Example 50: (E)-2-hydroxy-5-((2-(2-((4-(trifluoromethyl)phenyl)amino)pyrimidin-4-yl)phenyl)diazenyl)benzenesulfonic acid

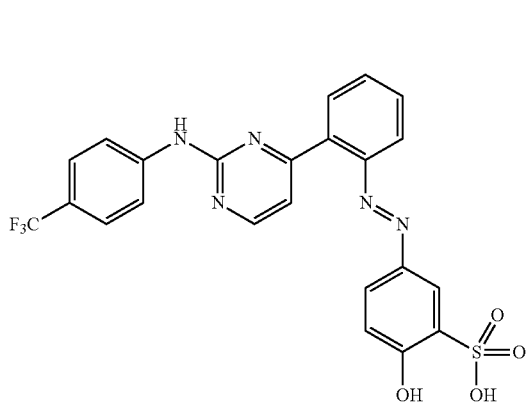 [SMILES: O=S(=O)(O)c1cc(/N=N/c2ccccc2-c2ccnc(Nc3ccc(C(F)(F)F)cc3)n2)ccc1O]

Example 50 was prepared following the procedure for example 33, by replacing phenol with 2-hydroxybenzenesulfonic acid. The residue was purified by prep-HPLC (mobile phase: CH₃CN/H₂O/0.1% NH₃—H₂O) to give the title compound (8.0 mg, 3%) as a yellow solid LC-MS: [M−H]⁻ (m/z)=514.0; ¹H NMR (400 MHz, CD₃OD) δ 8.59 (d, J=4.8 Hz, 1H), 8.35 (d, J=2.0 Hz, 1H), 8.04-8.01 (m, 1H), 7.92 (d, J=8.4 Hz, 2H), 7.87-7.85 (m, 1H), 7.78 (dd, J=8.4, 2.4 Hz, 1H), 7.71-7.67 (m, 2H), 7.50 (d, J=8.8 Hz, 2H), 7.17 (d, J=5.2 Hz, 1H), 6.94 (d, J=8.8 Hz, 1H).

Example 51: (E)-5-hydroxy-2-((2-(2-((4-(trifluoromethyl)phenyl)amino)pyrimidin-4-yl)phenyl)diazenyl)benzenesulfonic acid

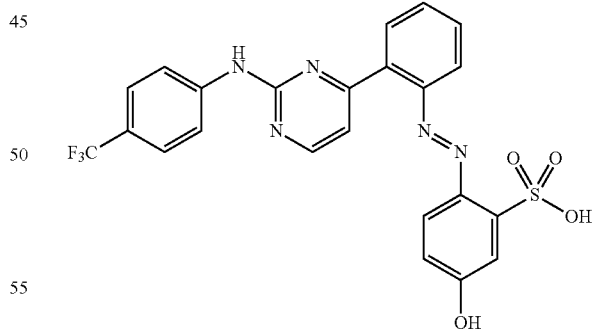

Example 51 was prepared following the procedure for example 33, by replacing phenol with 3-hydroxybenzenesulfonic acid. The residue was purified by prep-HPLC (mobile phase: CH₃CN/H₂O/0.1% NH₃—H₂O) to give the title compound (29.95 mg, 10%) as a yellow solid. LC-MS: [M+H]⁺ (m/z)=516.0; ¹H NMR (400 MHz, CD₃OD) δ 8.49 (d, J=5.2 Hz, 1H), 8.00-7.92 (m, 4H), 7.61-7.52 (m, 5H), 7.45 (d, J=8.4 Hz, 1H), 7.14 (d, J=5.2 Hz, 1H), 6.81 (dd, J=8.8, 2.8 Hz, 1H).

Example 52: (E)-2-amino-3-((2-(2-((4-(trifluoromethyl)phenyl)amino)pyrimidin-4-yl)phenyl)diazenyl)benzoic acid

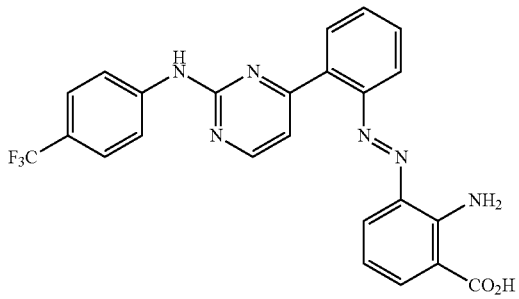 [SMILES: Nc1c(/N=N/c2ccccc2-c2ccnc(Nc3ccc(C(F)(F)F)cc3)n2)cccc1C(=O)O]

Example 52 was prepared following procedure for example 33, by replacing phenol with methyl 2-aminobenzoate, followed by hydrolysis using NaOH. The residue was purified by prep-HPLC (mobile phase: CH$_3$CN/H$_2$O/0.1% NH$_3$—H$_2$O) to give compound the title compound (21.1 mg, 55%) as a yellow solid. LC-MS: [M+H]$^+$ (m/z)=479.1; $^1$H NMR (400 MHz, DMSO-d6) δ 15.63 (s, 1H), 10.12 (s, 1H), 8.56 (d, J=5.2 Hz, 1H), 8.02 (d, J=8.4 Hz, 2H), 7.91 (dd, J=7.6, 1.2 Hz, 1H), 7.78 (dd, J=7.6, 1.2 Hz, 1H), 7.65-7.50 (m, 6H), 7.40 (td, J=7.6, 1.2 Hz, 1H), 7.27 (td, J=7.6, 1.6 Hz, 1H), 7.16 (d, J=5.2 Hz, 1H), 6.93 (t, J=7.6 Hz, 1H).

Example 53: (E)-5-(methylamino)-2-((2-(2-((4-(trifluoromethyl)phenyl)amino)pyrimidin-4-yl)phenyl)diazenyl)benzoic acid

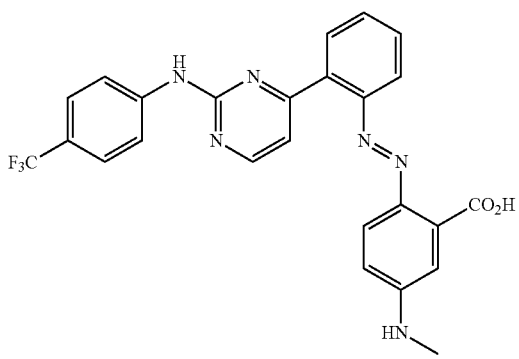 [SMILES: CNc1ccc(/N=N/c2ccccc2-c2ccnc(Nc3ccc(C(F)(F)F)cc3)n2)c(C(=O)O)c1]

Example 53 was prepared following procedure for example 33, by replacing phenol with methyl 3-(dimethylamino)benzoate, followed by hydrolysis using NaOH. The residue was purified by prep-HPLC (mobile phase: CH$_3$CN/H$_2$O/0.1% NH$_3$—H$_2$O) to give the title compound (29.7 mg, 75%) as a yellow solid. LC-MS: [M+H]$^+$ (m/z)=493.1; $^1$H NMR (400 MHz, DMSO-d6) δ 10.13 (s, 1H), 8.57 (d, J=5.2 Hz, 1H), 8.03 (d, J=8.4 Hz, 2H), 7.98 (m, 1H), 7.86 (dd, J=7.6, 1.2 Hz, 1H), 7.69-7.52 (m, 5H), 7.47 (dd, J=8.0, 1.6 Hz, 1H), 7.43 (td, J=7.6, 1.6 Hz, 1H), 7.35 (d, J=5.2 Hz, 1H), 7.34 (t, J=7.6 Hz, 1H), 3.56 (s, 3H).

Example 54: (E)-3-hydroxy-4-((2-(2-((4-(trifluoromethyl)phenyl)amino)pyrimidin-4-yl)phenyl)diazenyl)naphthalene-1-sulfonic acid

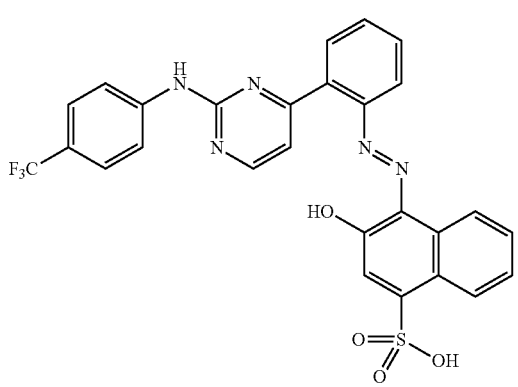 [SMILES: O=S(=O)(O)c1cc(O)c(/N=N/c2ccccc2-c2ccnc(Nc3ccc(C(F)(F)F)cc3)n2)c2ccccc12]

Example 54 was prepared following procedure for example 33, by replacing phenol with 3-hydroxynaphthalene-1-sulfonic acid. The residue was purified by prep-HPLC (mobile phase: CH$_3$CN/H$_2$O/0.1% NH$_3$—H$_2$O) to give the title compound (13.6 mg, 27%) as a yellow solid. LC-MS: [M–H]$^-$ (m/z)=564.2; $^1$H NMR (400 MHz, DMSO-d6) δ 10.24 (s, 1H), 8.76 (d, J=5.6 Hz, 1H), 8.61 (d, J=8.0 Hz, 1H), 8.51 (d, J=8.4 Hz, 1H), 8.46 (d, J=7.6 Hz, 1H), 8.14 (d, J=8.0 Hz, 1H), 8.06 (d, J=8.8 Hz, 2H), 7.76-7.72 (m, 3H), 7.64 (d, J=5.6 Hz, 1H), 7.58 (m, 1H), 7.45 (t, J=7.6 Hz, 2H), 7.15 (s, 1H).

Example 55: (E)-3-hydroxy-5-((2-(2-((4-(trifluoromethyl)phenyl)amino)pyrimidin-4-yl)phenyl)diazenyl)benzoic acid

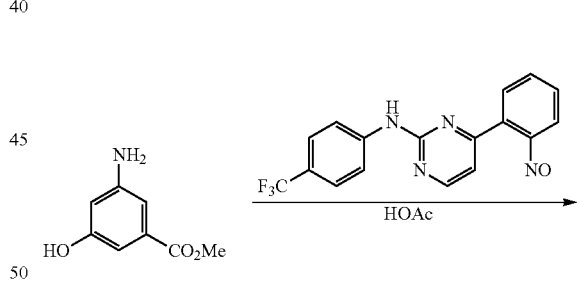

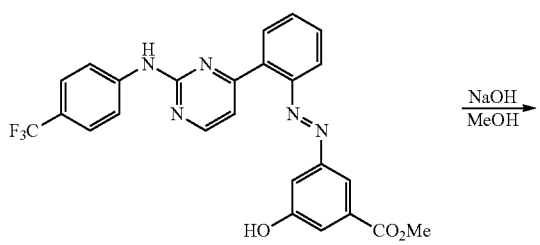

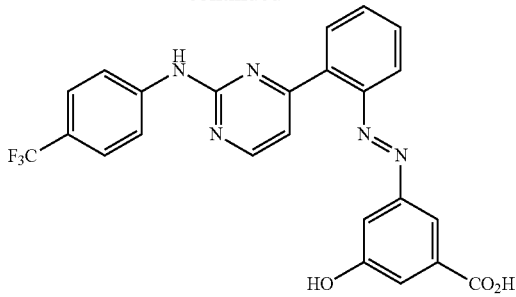

Step 1: methyl (E)-3-hydroxy-5-((2-(2-((4-(trifluoromethyl)phenyl)amino)pyrimidin-4-yl)phenyl)diazenyl)benzoate To a solution of 4-(2-nitrosophenyl)-N-(4-(trifluoromethyl)phenyl)pyrimidin-2-amine (example 31 step 1, 80 mg, 0.23 mmol, 1.0 eq) in HOAc (3 mL) was added methyl 3-amino-5-hydroxybenzoate (43 mg, 0.26 mmol, 1.1 eq). The mixture was stirred at 55° C. for 16 h. The reaction was monitored by LC-MS. The mixture was filtered, and the solid was washed with water and dried to give the title compound (35 mg, 31%) as a red solid, which was used in the next step without further purification. LC-MS: [M+H]⁺ (m/z)=494.0.

Step 2: (E)-3-hydroxy-5-((2-(2-((4-(trifluoromethyl)phenyl)amino)pyrimidin-4-yl)phenyl)diazenyl)benzoic acid To a solution of methyl (E)-3-hydroxy-5-((2-(2-((4-(trifluoromethyl)phenyl)amino)pyrimidin-4-yl)phenyl)diazenyl)benzoate (35 mg, 0.07 mmol, 1.0 eq) in MeOH (5.0 mL) was added NaOH (4.0 M, 2.0 mL). The mixture was stirred at 60° C. for 16 h. The reaction was monitored by LC-MS. The residue was purified by prep-HPLC (mobile phase: $CH_3CN/H_2O/0.1\%$ $NH_3$—$H_2O$) to give the title compound (17.3 mg, 51%) as a yellow solid. LC-MS: [M+H]⁺ (m/z)=480.1; ¹H NMR (400 MHz, $CD_3OD$) δ 8.53 (d, J=5.2 Hz, 1H), 8.02-7.98 (m, 2H), 7.90 (d, J=8.4 Hz, 2H), 7.76 (dd, J=7.6, 1.6 Hz, 1H), 7.69-7.63 (m, 2H), 7.54 (d, J=1.2 Hz, 1H), 7.45 (d, J=8.8 Hz, 2H), 7.32-7.31 (m, 1H), 7.09 (d, J=5.2 Hz, 1H).

Example 56: (E)-2-hydroxy-5-((2-(2-((3-(trifluoromethyl)phenyl)amino)pyrimidin-4-yl)phenyl)diazenyl)benzoic acid

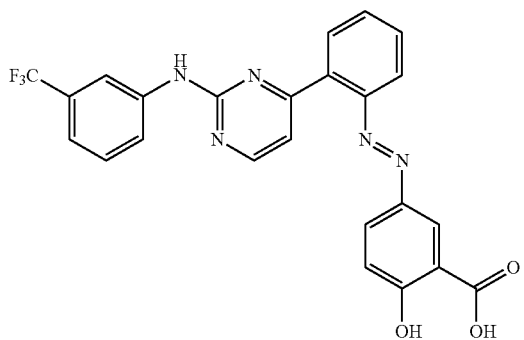

Example 56 was prepared following the procedure for example 32, by replacing 4-(2-aminophenyl)-N-(4-(trifluoromethyl)phenyl)pyrimidin-2-amine (example 3) with 4-(2-aminophenyl)-N-(3-(trifluoromethyl)phenyl)pyrimidin-2-amine (example 15) in step 2.

The mixture was concentrated and was purified by prep-HPLC ($CH_3CN/H_2O/0.1\%$ $NH_3$—$H_2O$) to give the title compound as a yellow solid (24.18 mg, 24%). LC-MS: [M−H]⁻ (m/z)=478.3; ¹H NMR (400 MHz, DMSO-d6) δ 10.10 (s, 1H), 8.57 (d, J=5.2 Hz, 1H), 8.38 (s, 1H), 8.22 (d, J=2.8 Hz, 1H), 8.02 (d, J=7.6 Hz, 1H), 7.94 (dd, J=7.6, 1.4 Hz, 1H), 7.60-7.70 (m, 4H), 7.46 (t, J=7.6 Hz, 1H), 7.24 (d, J=7.6 Hz, 1H), 7.05 (d, J=5.2 Hz, 1H), 6.73 (d, J=8.8 Hz, 1H).

Example 57: (E)-2-hydroxy-5-((3-(2-((3-(trifluoromethyl)phenyl)amino)pyrimidin-4-yl)phenyl)diazenyl)benzoic acid

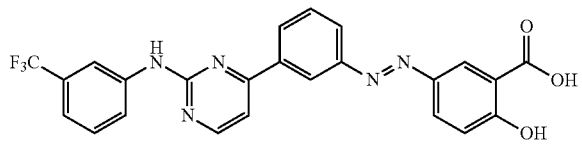 [SMILES: O=C(O)c1cc(/N=N/c2cccc(-c3ccnc(Nc4cccc(C(F)(F)F)c4)n3)c2)ccc1O]

Example 57 was prepared following the procedure for example 32, by replacing 4-(2-aminophenyl)-N-(4-(trifluoromethyl)phenyl)pyrimidin-2-amine (example 3) with 4-(3-aminophenyl)-N-(3-(trifluoromethyl)phenyl)pyrimidin-2-amine (example 16) in step 2.

The mixture was purified by prep-HPLC (mobile phase: $CH_3CN/H_2O/0.1\%$ $NH_3 \cdot H_2O$) to give the title compound (73.73 mg, 25.7%) as a yellow solid. LC-MS: [M−H]⁻ (m/z)=478.3; ¹H NMR (400 MHz, DMSO-d6) δ 10.13 (s, 1H), 8.71-8.60 (m, 2H), 8.47 (s, 1H), 8.34 (d, J=2.4 Hz, 1H), 8.27 (d, J=7.6 Hz, 1H), 8.04 (d, J=8.8 Hz, 1H), 7.98 (d, J=8.4 Hz, 1H), 7.88 (dd, J=8.8, 2.4 Hz, 1H), 7.72 (t, J=8.0 Hz, 1H), 7.64 (d, J=5.2 Hz, 1H), 7.56 (t, J=8.0 Hz, 1H), 7.32 (d, J=7.6 Hz, 1H), 6.82 (d, J=8.8 Hz, 1H).

Example 58: (E)-5-((5-((4-(3-chlorophenyl)pyrimidin-2-yl)amino)-2-(trifluoromethyl)phenyl)diazenyl)-2-hydroxybenzoic acid

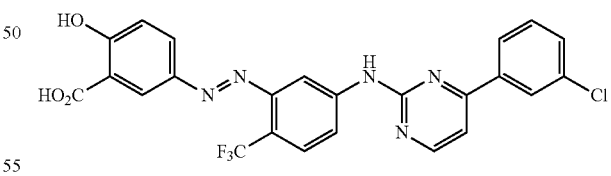

At 0° C., to a solution of N¹-(4-(3-chlorophenyl)pyrimidin-2-yl)-4-(trifluoromethyl)benzene-1,3-diamine (example 22, 110 mg, 0.28 mmol, 1.0 eq) in 6.0 M aq. HCl (8.0 mL) was added a solution of $NaNO_2$ (39 mg, 0.56 mmol, 2.0 eq) in water. The mixture was stirred at 0° C. for 0.5 h, and then 2-hydroxybenzoic acid (43 mg, 0.31 mmol, 1.1 eq) in 2.0 M aq. NaOH was added. The mixture was adjusted to pH ~8 with 2.0 M aq. NaOH, and then stirred for 1 h at 0° C. The reaction was monitored by LC-MS. The mixture was adjusted to pH ~7 with 1.0 M HCl and extracted with EtOAc. The organic layer was concentrated. The residue was purified by prep-HPLC (mobile phase: MeCN/H₂O/ 0.1% NH₃·H₂O) to give the title compound (80.2 mg, 21%) as a yellow solid. LC-MS: [M−H]⁻ (m/z)=512.0; ¹H NMR (400 MHz, DMSO-d6) δ 10.37 (s, 1H), 8.70 (d, J=5.6 Hz, 1H), 8.63 (s, 1H), 8.37 (d, J=2.4 Hz, 1H), 8.25-8.22 (m, 2H), 7.96-7.84 (m, 3H), 7.65-7.61 (m, 3H), 7.05-6.03 (m, 1H).

Comparative Example 59: (E)-2-hydroxy-5-(2-(2-((4-(trifluoromethyl)phenyl)amino)pyrimidin-4-yl)styryl)benzoic acid

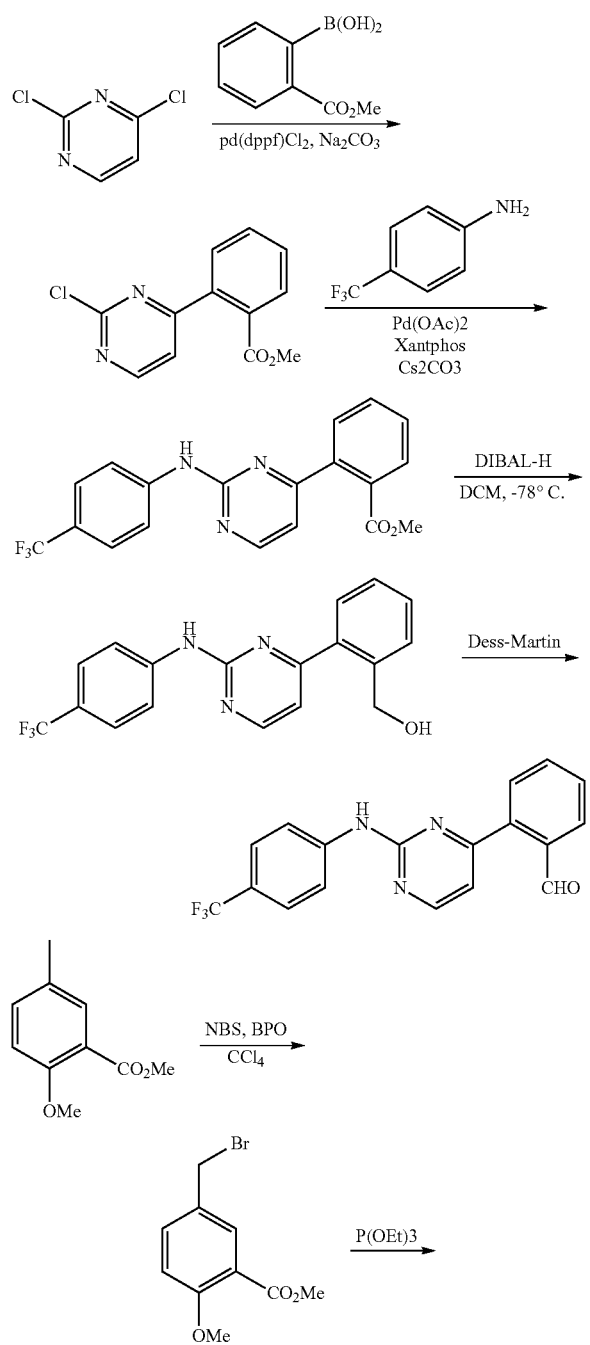

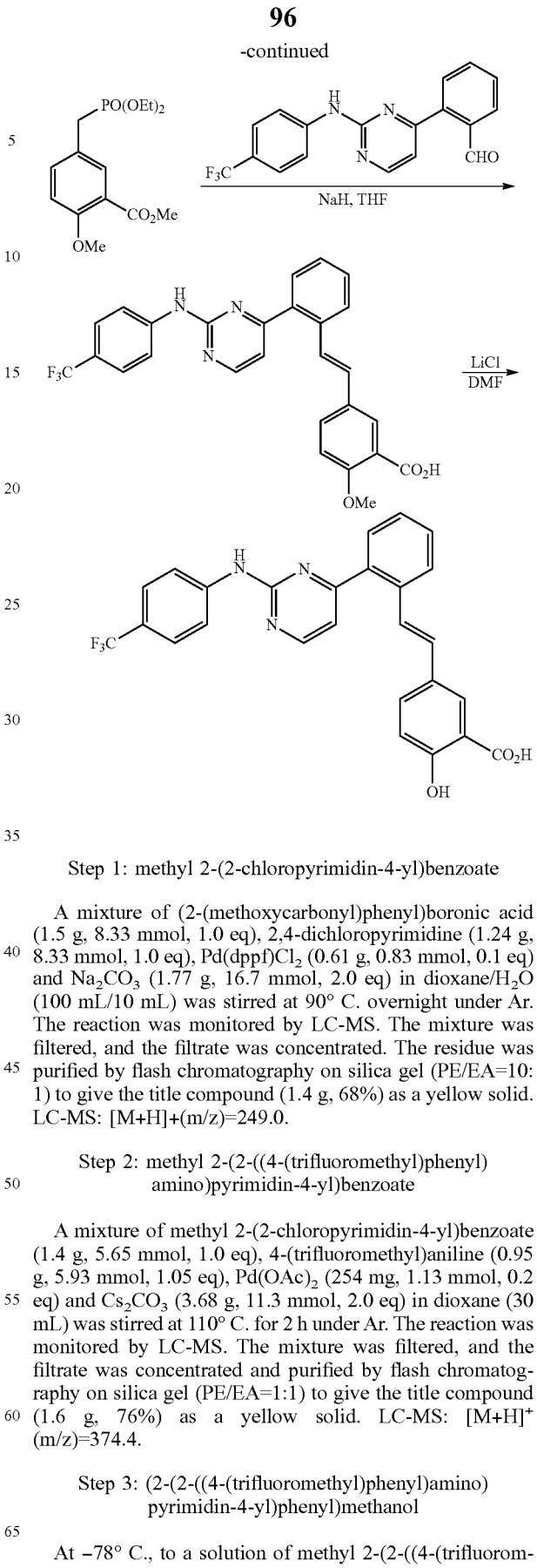

Step 1: methyl 2-(2-chloropyrimidin-4-yl)benzoate

A mixture of (2-(methoxycarbonyl)phenyl)boronic acid (1.5 g, 8.33 mmol, 1.0 eq), 2,4-dichloropyrimidine (1.24 g, 8.33 mmol, 1.0 eq), Pd(dppf)Cl₂ (0.61 g, 0.83 mmol, 0.1 eq) and Na₂CO₃ (1.77 g, 16.7 mmol, 2.0 eq) in dioxane/H₂O (100 mL/10 mL) was stirred at 90° C. overnight under Ar. The reaction was monitored by LC-MS. The mixture was filtered, and the filtrate was concentrated. The residue was purified by flash chromatography on silica gel (PE/EA=10:1) to give the title compound (1.4 g, 68%) as a yellow solid. LC-MS: [M+H]+(m/z)=249.0.

Step 2: methyl 2-(2-((4-(trifluoromethyl)phenyl)amino)pyrimidin-4-yl)benzoate

A mixture of methyl 2-(2-chloropyrimidin-4-yl)benzoate (1.4 g, 5.65 mmol, 1.0 eq), 4-(trifluoromethyl)aniline (0.95 g, 5.93 mmol, 1.05 eq), Pd(OAc)₂ (254 mg, 1.13 mmol, 0.2 eq) and Cs₂CO₃ (3.68 g, 11.3 mmol, 2.0 eq) in dioxane (30 mL) was stirred at 110° C. for 2 h under Ar. The reaction was monitored by LC-MS. The mixture was filtered, and the filtrate was concentrated and purified by flash chromatography on silica gel (PE/EA=1:1) to give the title compound (1.6 g, 76%) as a yellow solid. LC-MS: [M+H]⁺ (m/z)=374.4.

Step 3: (2-(2-((4-(trifluoromethyl)phenyl)amino)pyrimidin-4-yl)phenyl)methanol

At −78° C., to a solution of methyl 2-(2-((4-(trifluoromethyl)phenyl)amino)pyrimidin-4-yl)benzoate (900 mg, 2.41 mmol, 1.0 eq) in DCM (20 mL) was added DIBAL-H (11 mL, 10.62 mmol, 4.4 eq). The mixture was stirred for 2 h under Ar. The reaction was monitored by LC-MS. The reaction was quenched with MeOH at −78° C. and then allowed to warm to RT. The mixture was diluted with saturated Rochelle's salt solution and stirred for 16 h. The organic layer was separated, and the aqueous layer was extracted with DCM. The combined organic layer was dried over Na$_2$SO$_4$, filtered and concentrated. The residue was purified by flash chromatography on silica gel (PE/EA=1:1) to give the title compound (400 mg, 48%) as a yellow solid. LC-MS: [M+H]$^+$ (m/z)=346.4.

Step 4: 2-(2-((4-(trifluoromethyl)phenyl)amino)pyrimidin-4-yl)benzaldehyde

At 0° C., to a mixture of (2-(2-((4-(trifluoromethyl)phenyl)amino)pyrimidin-4-yl)phenyl)methanol (100 mg, 0.29 mmol, 1.0 eq) in DCM (15 mL) was added Dess-Martin periodinane (147 mg, 0.35 mmol, 1.2 eq). The reaction mixture was stirred for 2 h at RT. The reaction was monitored by LC-MS. The mixture was quenched with NaHCO$_3$ (aq) at 0° C. and extracted with DCM. The combined organic layer was dried over Na$_2$SO$_4$, filtered and concentrated under reduced pressure. The residue was purified by prep-TLC (eluent: PE/EA=4:1) to give the title compound (79 mg, 80%) as a yellow solid. LC-MS: [M+H]$^+$ (m/z)=344.4.

Step 5: methyl 5-(bromomethyl)-2-methoxybenzoate

A mixture of methyl 2-methoxy-5-methylbenzoate (2.0 g, 11.11 mmol, 1.0 eq), NBS (2.37 g, 13.33 mmol, 1.2 eq) and BPO (1.61 g, 6.67 mmol, 0.6 eq) in CCl$_4$ (20 mL) was stirred at 80° C. for 16 h. The reaction was monitored by LC-MS. The mixture was quenched with Na$_2$S$_2$O$_3$ (aq) at 0° C. and extracted with DCM. The organic layer was dried over Na$_2$SO$_4$, filtered and concentrated. The residue was purified by flash chromatography on silica gel (eluent: PE/EA=10:1) to give the title compound (2.2 g, 70%) as a white solid. LC-MS: [M+H]$^+$ (m/z)=259.3.

Step 6: methyl 5-((diethoxyphosphoryl)methyl)-2-methoxybenzoate

A mixture of methyl 5-(bromomethyl)-2-methoxybenzoate (1.23 g, 4.75 mmol, 1.0 eq), Bu$_4$NI (177 mg, 0.48 mmol, 0.1 eq) and triethyl phosphite (1.2 mL, 6.89 mmol, 1.45 eq) was stirred at 130° C. for 16 h. The reaction was monitored by LC-MS. Triethyl phosphite was removed under reduced pressure to give the title compound (800 mg) which was used in next step without further purification. LC-MS: [M+H]$^+$ (m/z)=317.4.

Step 7: (E)-2-methoxy-5-(2-(2-((4-(trifluoromethyl)phenyl)amino)pyrimidin-4-yl)styryl)benzoic acid At 0° C., to a solution of methyl 5-((diethoxyphosphoryl)methyl)-2-methoxybenzoate (28 mg, 0.09 mmol, 1.5 eq) in THF (3 mL) was added NaH (4 mg, 0.09 mmol, 1.5 eq) by portions under Ar. After 10 min, a solution of methyl 5-((diethoxyphosphoryl)methyl)-2-methoxybenzoate (20 mg, 0.06 mmol, 1.0 eq) in THF (1 mL) was added. The mixture was stirred for 16 h at RT. The reaction was monitored by LC-MS. The mixture was quenched with NH$_4$Cl(aq) at 0° C. and extracted with DCM. The organic layer was dried over Na$_2$SO$_4$, concentrated under reduced pressure and purified by prep-TLC (eluent: DCM/MeOH=20:1) to give the title compound (20 mg, 69%) as a yellow solid. LC-MS: [M+H]$^+$ (m/z)=492.6.

Step 8: (E)-2-hydroxy-5-(2-(2-((4-(trifluoromethyl)phenyl)amino)pyrimidin-4-yl)styryl)benzoic acid A solution of (E)-2-methoxy-5-(2-(2-((4-(trifluoromethyl)phenyl)amino)pyrimidin-4-yl)styryl)benzoic acid (20 mg, 0.04 mmol, 1.0 eq) and LiCl (34 mg, 0.81 mmol, 20 eq) in DMF (1.0 mL) was stirred at 140° C. for 16 h. The reaction was monitored by LC-MS. The residue was purified by prep-HPLC (mobile phase: CH$_3$CN/H$_2$O/0.1% NH$_3$—H$_2$O) to give the title compound (11.6 mg, 57%) as a yellow solid. LC-MS: [M+H]$^+$ (m/z)=478.1; $^1$H NMR (400 MHz, CD$_3$OD) δ 8.45 (d, J=5.2 Hz, 1H), 7.87 (d, J=2.0 Hz, 1H), 7.83 (d, J=8.4 Hz, 2H), 7.73 (d, J=7.6 Hz, 1H), 7.50 (dd, J=7.2, 0.8 Hz, 1H), 7.40 (t, J=7.6 Hz, 1H), 7.30-7.26 (m, 4H), 7.20 (d, J=16.4 Hz, 1H), 7.03 (d, J=16.0 Hz, 1H), 6.96 (d, J=5.2 Hz, 1H), 6.63 (d, J=8.4 Hz, 1H).

Example 60: 4-(2-aminophenyl)-N-(p-tolyl)pyrimidin-2-amine

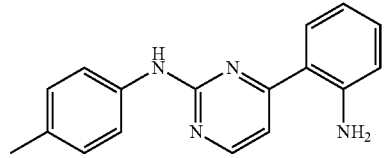 [SMILES: Cc1ccc(Nc2nccc(-c3ccccc3N)n2)cc1]

Example 60 was prepared following the procedure for example 4, by replacing 4-(trifluoromethyl)aniline with methyl 4-aminobenzoate in step 1 and 1-(5-chloro-2-nitrophenyl)ethan-1-one with 1-(2-nitrophenyl)ethan-1-one in step 2.

The crude product was purified by prep-HPLC (CH$_3$CN/H$_2$O/0.1% NH$_3$·H$_2$O) to give the title compound (26 mg, 28%) as a white solid. LC-MS: [M+H]$^+$ (m/z)=277.1; $^1$H NMR (400 MHz, DMSO-d6) δ 9.53 (s, 1H), 8.41 (d, J=5.6 Hz, 1H), 7.68 (d, J=7.2 Hz, 1H), 7.59 (d, J=8.4 Hz, 2H), 7.21 (d, J=5.6 Hz, 1H), 7.16-7.10 (m, 3H), 6.99 (s, 2H), 6.76 (d, J=8.4 Hz, 1H), 6.58 (t, J=6.8 Hz, 1H), 2.26 (s, 3H).

Example 61: (E)-2-hydroxy-5-((2-(2-(p-tolylamino)pyrimidin-4-yl)phenyl)diazenyl)benzoic acid

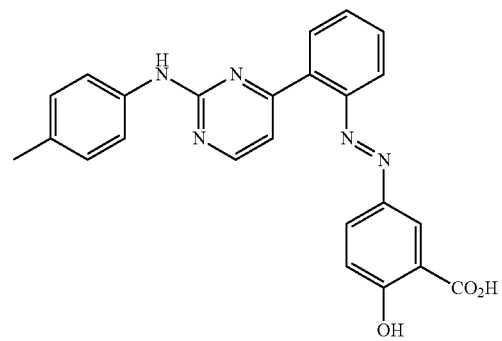

Example 61 was prepared following the procedure for example 32, by replacing methyl 5-amino-2-hydroxybenzoate with methyl 4-aminobenzoate in step 1.

The crude product was purified by prep-HPLC ($CH_3CN$/$H_2O$/0.1% $NH_3 \cdot H_2O$) to give the title compound (43 mg, 31%) as a yellow solid. LC-MS: $[M+H]^+$ (m/z)=426.1; $^1H$ NMR (400 MHz, DMSO-d6) δ 9.58 (s, 1H), 8.47 (d, J=4.8 Hz, 1H), 8.21 (d, J=2.8 Hz, 1H), 7.91-7.88 (m, 1H), 7.68-7.56 (m, 6H), 7.03 (d, J=8.4 Hz, 2H), 6.92 (d, J=5.2 Hz, 1H), 6.68 (d, J=8.8 Hz, 2H), 6.60 (s, 1H), 2.23 (s, 3H).

Example 62: (E)-5-((2-(2-((4-carboxyphenyl)amino)pyrimidin-4-yl)phenyl)diazenyl)-2-hydroxybenzoic acid

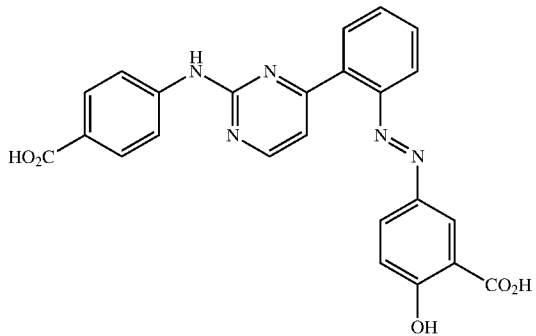 [SMILES: O=C(O)c1ccc(Nc2nccc(-c3ccccc3/N=N/c3ccc(O)c(C(=O)O)c3)n2)cc1]

Example 62 was prepared following the procedure for example 32, by replacing 4-(2-aminophenyl)-N-(4-(trifluoromethyl)phenyl)pyrimidin-2-amine with 4-((4-(2-aminophenyl)pyrimidin-2-yl)amino)benzoic acid in step 2.

The crude product was purified by prep-HPLC ($CH_3CN$/$H_2O$/0.1% $NH_3 \cdot H_2O$) to give the title compound (65 mg, 34%) as a yellow solid. LC-MS: $[M+H]^+$ (m/z)=456.1; $^1H$ NMR (400 MHz, DMSO-d6) δ 10.05 (s, 1H), 8.57 (d, J=5.2 Hz, 1H), 8.26 (d, J=2.4 Hz, 1H), 7.96-7.83 (m, 5H), 7.70-7.62 (m, 4H), 7.05 (d, J=5.2 Hz, 1H), 6.73 (d, J=8.8 Hz, 1H).

Biological Data 1: HT29 AhR Reporter Assay

HT29-Lucia AhR cells were purchased from Invivogen (cat #ht21-ahr). HT29-AhR cells were propagated once in growth medium (DMEM, 10% FBS (30 min at 56° C.), 100 U/ml penicillin, 100 µg/ml streptomycin, 100 µg/ml Normocin™ and 100 µg/ml Zeocin™) at 37° C. in an atmosphere of 5% $CO_2$. The cell suspension was removed from growth medium and rinsed gently with pre-warmed PBS (10 mL). Pre-warmed Trypsin (1 mL) was added, and cells were held at 30° C. for about 5 min and then detached by pipette. The dissociated cell clumps were gently pipetted up and down. The cells were resuspended in pre-warmed detection medium (DMEM, 10% FBS (30 min at 56° C.), 100 U/ml penicillin, 100 µg/ml streptomycin, and test article or vehicle) and counted. A cell suspension of ~500,000 cells/mL in Detection medium was prepared.

The cells were plated into a 96-well plate at a density of 50,000 cells/well and incubated at 37° C. for 18-24 h in an atmosphere of 5% $CO_2$. Samples (20 µL/well) were pipetted into a 96-well white (opaque), and QUANTI-Luc™ (50 µL/well) was added. The plate was gently tapped and then read in a luminometer (0.1 s reading time). The data was analyzed, and EC50 curves and values were generated using GraphPad Prism 6.02 software.

$$\% \text{ efficacy} = 100\% * (TA - BG)/(Ref - BG)$$

TA is the luminescent readout of test article.

BG is the background readout of DMSO vehicle, and

Ref is the readout of reference compound, which is VAF347.

EC50: the concentration to reach half of maximum efficacy of reference compound (VAF347).

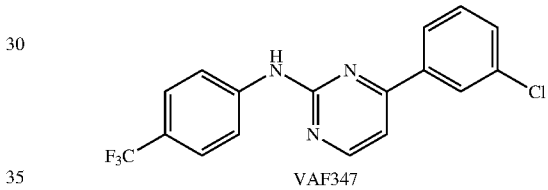

TABLE 1

| AhR activity of selected compounds with $Z^1$ or $Z^2$ equals $NH_2$. | | | | | |
|---|---|---|---|---|---|
| Example | HT29 AhR EC50 µM (% efficacy) | Example | HT29 AhR EC50 µM (% efficacy) | Example | HT29 AhR EC50 µM (% efficacy) |
| VAF347 | 0.026 (100%) | 1 | >30 (16%) | 2 | <0.014 (275%) |
| 3 | 1.33 (165%) | 4 | >30 (18%) | 5 | 20 (46%) |
| 6 | >30 (15%) | 7 | >30 (29%) | 8 | >30 (13%) |
| 9 | 2.62 (89%) | 10 | 9.24 (69%) | 11 | >30 (−17%) |
| 12 | >30 (17%) | 13 | >30 (7%) | 14 | 16.9 (51%) |
| 18 | >30 (10%) | 20 | >30 (13%) | 21 | >30 (27%) |
| 22 | 0.018 (124%) | 23 | >30 (33%) | 24 | >30 (5%) |
| 25 | 6.92 (21%) | 26 | >30 (141%) | 59 | 1.42 (74%) |

Biological Data 2: Stability in Human Feces

Azo compounds are not expected to exhibit AhR agonist activity until reduction occurs, which is mediated by gut bacteria. Accordingly, selected azo compounds of the invention were exposed to human feces under conditions suitable to promote azo reduction. Efficient reduction is expected to provide delivery of active moiety in the gut.

The human feces from two donors were homogenized in isotonic phosphate buffered saline (pH 6.8) with a ratio of 1:10 (w/v). The tubes were sealed using sealing film. Test article was dissolved in isotonic phosphate buffer (pH 6.8) to form a working solution of 20 µM (if the solubility allows). An aliquot of working solution (50 µL) was added to the human feces homogenate (50 µl) for each time point (0% 1, 2, 4, 6 and 24 h) in duplicate and placed under nitrogen for about 1 minute in order to exhaust air, and then incubated at 37° C. After incubation at each pre-set time point, 1000 μL acetonitrile containing internal standard was added to each tube to quench reaction. Samples were vortexed and centrifuged at 3700 rpm for 10 min and the supernatant was transferred for analysis (and diluted where necessary). The concentrations of test article and its metabolite (example 3) in the supernatants were determined using LC-MS/MS method. Sulfasalazine was used as a positive control. All incubations were performed in duplicate.

TABLE 2

Stability of selected compounds with $Z^1$ or $Z^2$ equals —N=N—Ar in human feces

| Example | % of parent remaining after incubation for 6 h | % of $Z^1$ or $Z^2$ = $NH_2$ metabolite formed after incubation for 6 h[2] |
|---|---|---|
| 27 | 74 | 6 |
| 32 | 49 | 45 |
| 33 | 59 | 16 |
| 34 | 95 | 1 |
| 36 | 19 | 60 |
| 37 | 69 | 13 |
| 38 | 4 | 59 |
| 40 | 22 | 66 |
| 42 | 98 | 0.7 |
| 43 | 74 | 2 |
| 47 | 81 | 7 |
| 49 | 33 | 42 |
| 50 | 10 | 58 |
| 55 | 76 | 28 |
| 59[1] | 94 | 0 |

[1]Example 59 is a non-cleavable control, and is not a compound of Formula (I)

[2]Example 2 is measured as the metabolite of example 27, and example 3 is measured as the metabolite of the rest of compounds.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The invention claimed is:

1. A compound of Formula (I):

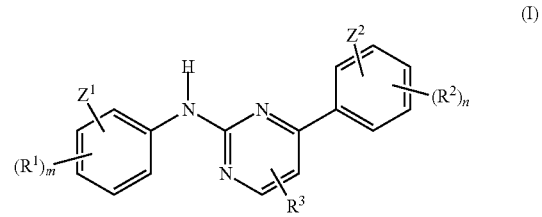

wherein:
one of $Z^1$ and $Z^2$ is —N=N—Ar, and the other of $Z^1$ and $Z^2$ is H;
wherein Ar is selected from phenyl, naphthyl, and

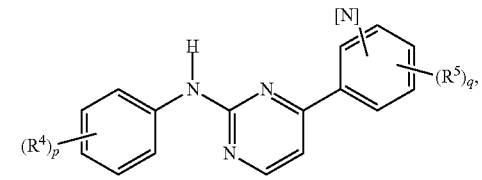

wherein each phenyl and naphthyl is optionally substituted with up to three groups selected from —OR, COOR, $C_{1-4}$ alkyl, $C_{1-4}$ haloalkyl, $C_{1-4}$ haloalkoxy, —$NR_2$, CN, —$PO_3R_2$, —$SO_2R$, —$SO_3R$, and halo;
$R^3$ is selected from H, CN, halo, $C_{1-4}$ alkyl, $C_{1-4}$ haloalkyl, and $C_{1-4}$ haloalkoxy;
each $R^1$ and $R^4$ is independently selected from —OR, COOR, $C_{1-4}$ haloalkyl, $C_{1-4}$ haloalkoxy, —$NR_2$, CN, —$PO_3R^2$, —$SO_2R$, —$SO_3R$, halo, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'$_2$;
each $R^2$ and $R^5$ is independently selected from halo, —OR, COOR, $C_{1-4}$ haloalkyl, $C_{1-4}$ haloalkoxy, —$NR_2$, CN, —$PO_3R^2$, —$SO_2R$, —$SO_3R$, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'$_2$;
each R is independently selected from H, $C_{1-4}$ haloalkyl, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'$_2$;
each R' is independently selected from H and $C_{1-3}$ alkyl;
each m, n, p, and q is independently selected from 0, 1 and 2; and
[N] represents the attachment of Ar to N in —N=N—Ar;
or a pharmaceutically acceptable salt thereof.

2. The compound of claim 1, wherein Ar is phenyl or naphthyl, and is optionally substituted with up to three groups selected from —OR, COOR, $C_{1-4}$ alkyl, $C_{1-4}$ haloalkyl, $C_{1-4}$ haloalkoxy, —$NR_2$, CN, —$PO_3R^2$, —$SO_2R$, —$SO_3R$, and halo;
or a pharmaceutically acceptable salt thereof.

3. The compound of claim 1, wherein $R^3$ is H;
or a pharmaceutically acceptable salt thereof.

4. The compound of claim 1, wherein p and q are independently selected from 0 and 1;
or a pharmaceutically acceptable salt thereof.

5. The compound of claim 1, wherein n is 0; or a pharmaceutically acceptable salt thereof.

6. The compound of claim 5, wherein $R^3$ is H; or a pharmaceutically acceptable salt thereof.

7. The compound of claim 1, wherein $Z^1$ is H; or a pharmaceutically acceptable salt thereof.

8. The compound of claim 2, wherein Ar is selected from the group consisting of:

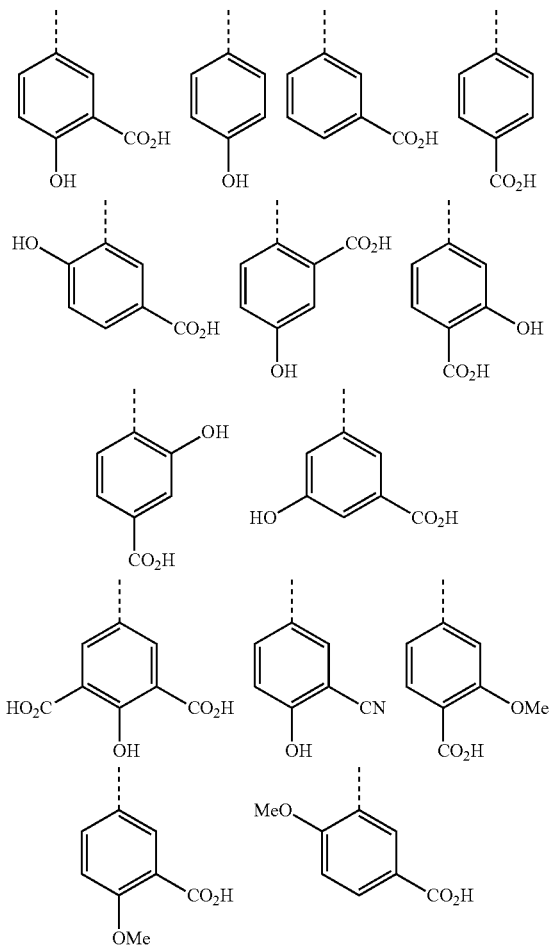

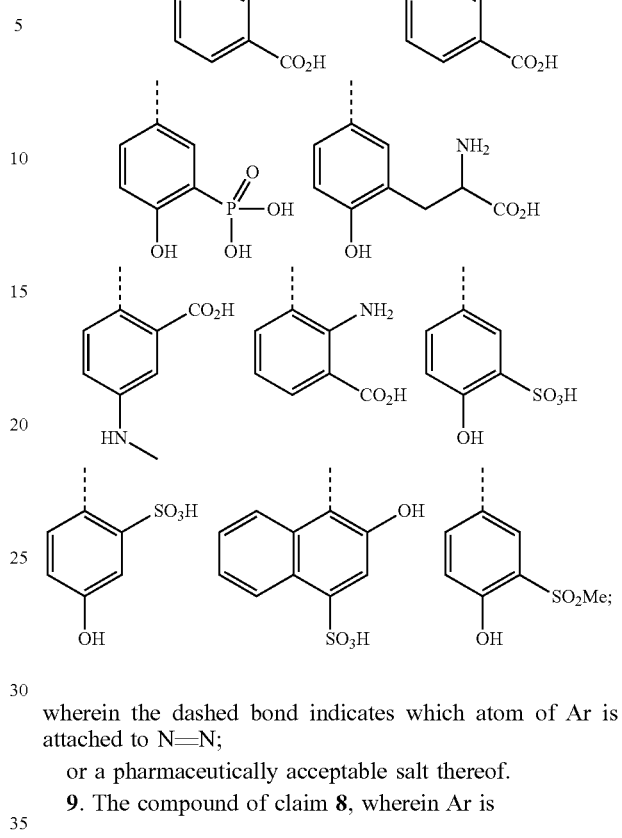

wherein the dashed bond indicates which atom of Ar is attached to N=N;

or a pharmaceutically acceptable salt thereof.

9. The compound of claim 8, wherein Ar is

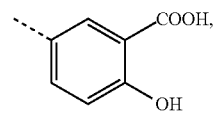

wherein the dashed bond indicates which atom of Ar is attached to —N=N;

or a pharmaceutically acceptable salt thereof.

10. The compound of claim 1, which is selected from:

| Example | Structure |
| --- | --- |
| 27. | 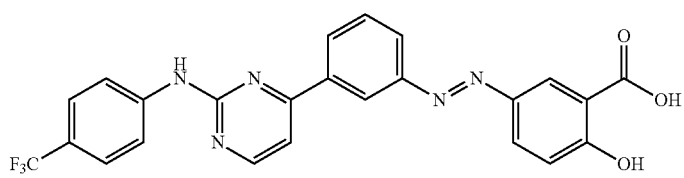 [SMILES: O=C(O)c1cc(/N=N/c2cccc(-c3ccnc(Nc4ccc(C(F)(F)F)cc4)n3)c2)ccc1O] |
| 28. | 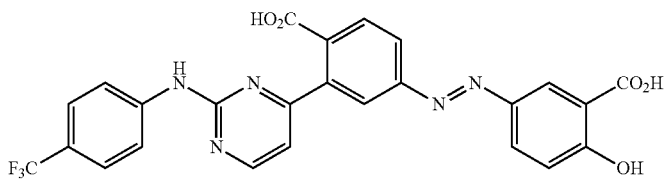 [SMILES: O=C(O)c1cc(/N=N/c2ccc(C(=O)O)c(-c3ccnc(Nc4ccc(C(F)(F)F)cc4)n3)c2)ccc1O] |

| Example | Structure |
|---|---|
| 29. | 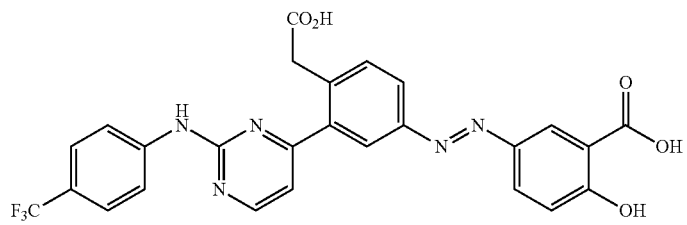 [SMILES: O=C(O)Cc1ccc(/N=N/c2ccc(O)c(C(=O)O)c2)cc1-c1ccnc(Nc2ccc(C(F)(F)F)cc2)n1] |
| 30. | 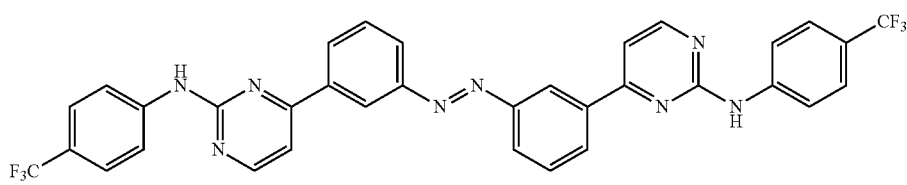 [SMILES: FC(F)(F)c1ccc(Nc2nccc(-c3cccc(/N=N/c4cccc(-c5ccnc(Nc6ccc(C(F)(F)F)cc6)n5)c4)c3)n2)cc1] |
| 31. | 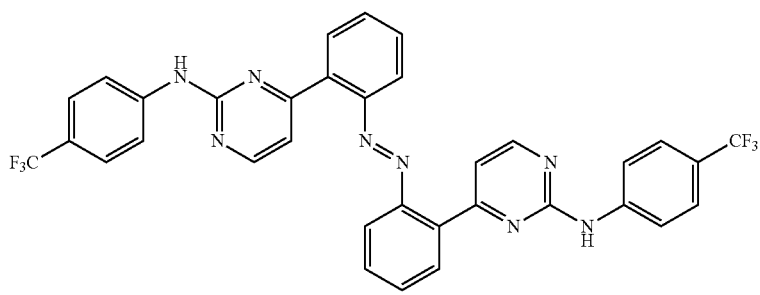 [SMILES: FC(F)(F)c1ccc(Nc2nccc(-c3ccccc3/N=N/c3ccccc3-c3ccnc(Nc4ccc(C(F)(F)F)cc4)n3)n2)cc1] |
| 32. | 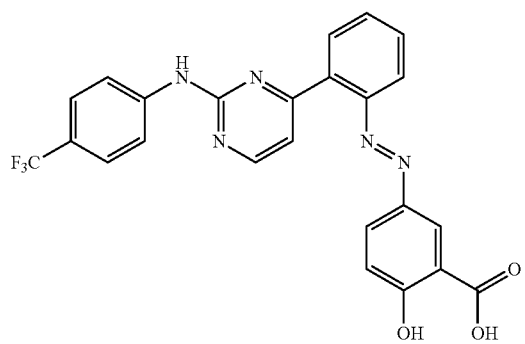 [SMILES: O=C(O)c1cc(/N=N/c2ccccc2-c2ccnc(Nc3ccc(C(F)(F)F)cc3)n2)ccc1O] |
| 33. | 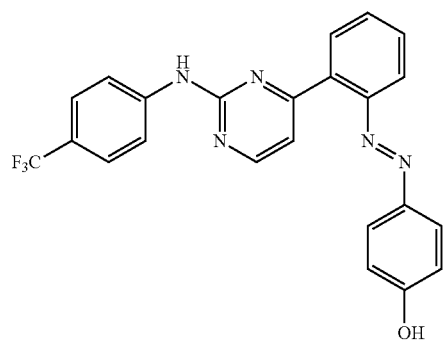 [SMILES: Oc1ccc(/N=N/c2ccccc2-c2ccnc(Nc3ccc(C(F)(F)F)cc3)n2)cc1] |

-continued
| Example | Structure |
|---------|-----------|
| 34. | 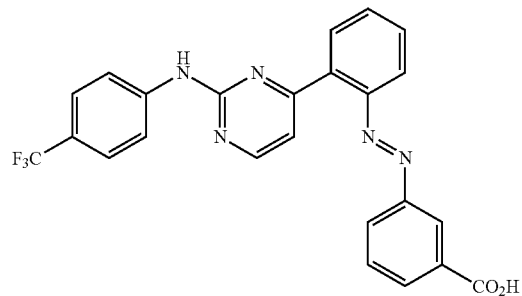 |
| 35. | 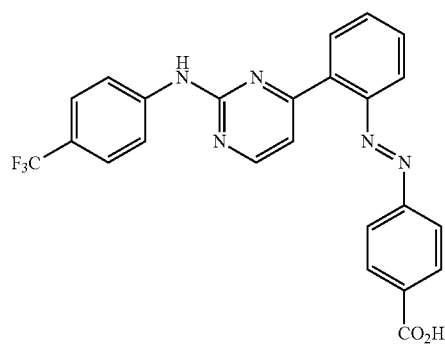 [SMILES: O=C(O)c1ccc(/N=N/c2ccccc2-c2ccnc(Nc3ccc(C(F)(F)F)cc3)n2)cc1] |
| 36. | 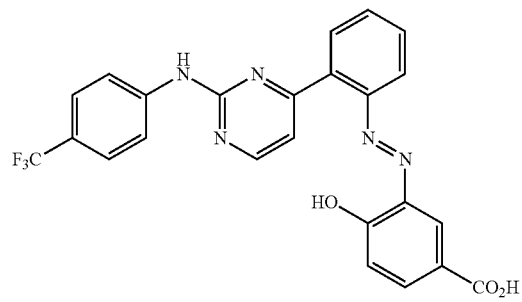 |
| 37. | 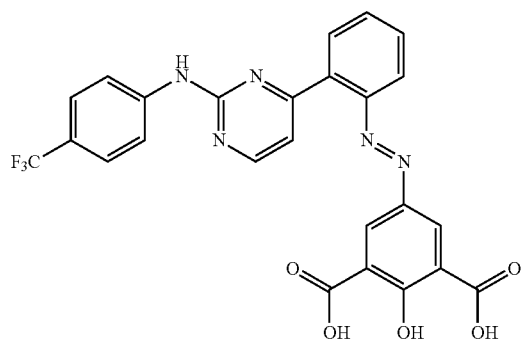 [SMILES: O=C(O)c1cc(/N=N/c2ccccc2-c2ccnc(Nc3ccc(C(F)(F)F)cc3)n2)cc(C(=O)O)c1O] |

-continued
| Example | Structure |
|---|---|
| 38. | 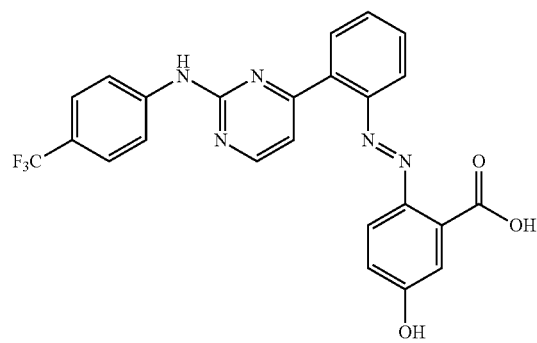 [SMILES: O=C(O)c1cc(O)ccc1/N=N/c1ccccc1-c1ccnc(Nc2ccc(C(F)(F)F)cc2)n1] |
| 39. | 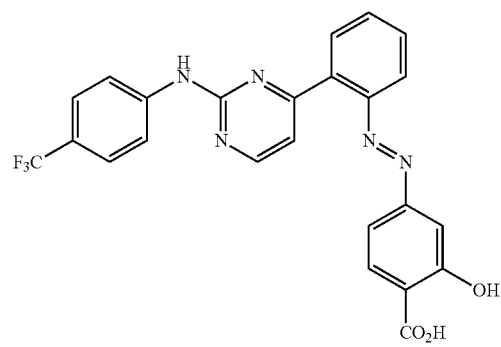 [SMILES: O=C(O)c1ccc(/N=N/c2ccccc2-c2ccnc(Nc3ccc(C(F)(F)F)cc3)n2)cc1O] |
| 40. | 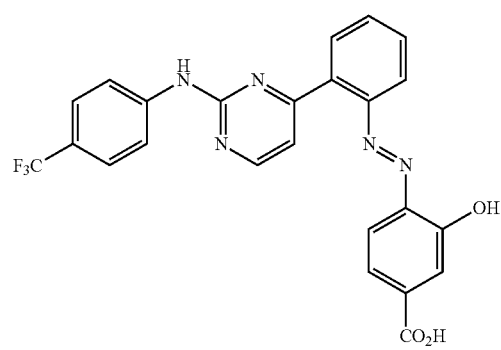 [SMILES: O=C(O)c1ccc(/N=N/c2ccccc2-c2ccnc(Nc3ccc(C(F)(F)F)cc3)n2)c(O)c1] |
| 41. | 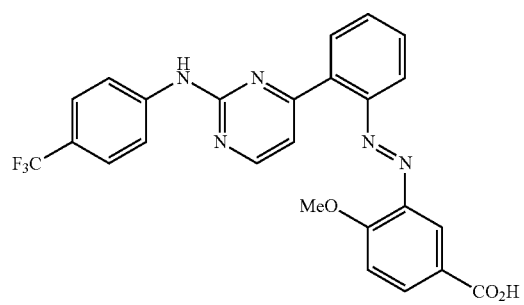 [SMILES: COc1ccc(C(=O)O)cc1/N=N/c1ccccc1-c1ccnc(Nc2ccc(C(F)(F)F)cc2)n1] |

-continued

| Example | Structure |
|---|---|
| 42. | (structure: 4-(trifluoromethyl)phenyl-NH-pyrimidine-phenyl-N=N-phenyl with OMe and CO₂H) |
| 43. | (structure: 4-(trifluoromethyl)phenyl-NH-pyrimidine-phenyl-N=N-phenyl with CO₂H and OMe) |
| 44. | (structure: 4-(trifluoromethyl)phenyl-NH-pyrimidine-phenyl-N=N-phenyl with F₃CO and CO₂H) |
| 45. | (structure: 4-(trifluoromethyl)phenyl-NH-pyrimidine-phenyl-N=N-phenyl with EtO and CO₂H) |

| Example | Structure |
|---|---|
| 46. | 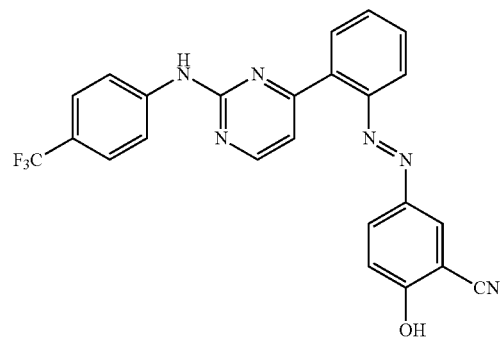 [SMILES: N#Cc1cc(/N=N/c2ccccc2-c2ccnc(Nc3ccc(C(F)(F)F)cc3)n2)ccc1O] |
| 47. | 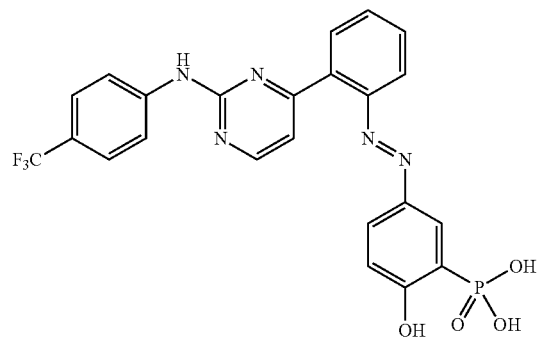 [SMILES: O=P(O)(O)c1cc(/N=N/c2ccccc2-c2ccnc(Nc3ccc(C(F)(F)F)cc3)n2)ccc1O] |
| 48. | 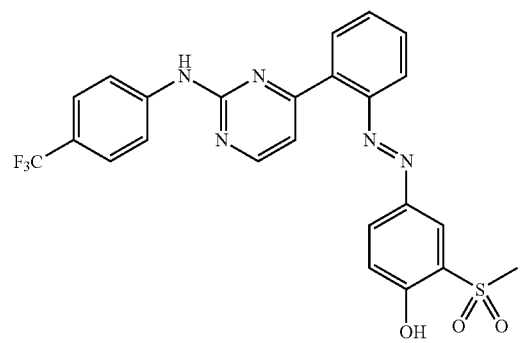 [SMILES: CS(=O)(=O)c1cc(/N=N/c2ccccc2-c2ccnc(Nc3ccc(C(F)(F)F)cc3)n2)ccc1O] |
| 49. | 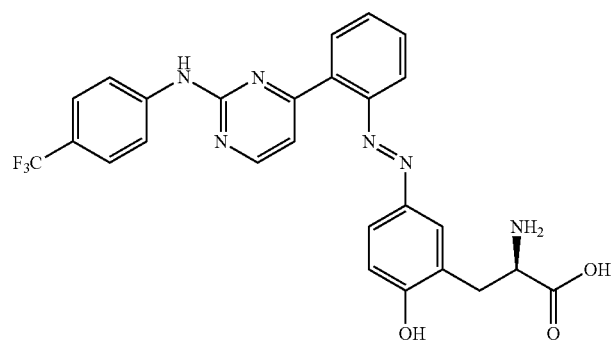 [SMILES: N[C@H](Cc1cc(/N=N/c2ccccc2-c2ccnc(Nc3ccc(C(F)(F)F)cc3)n2)ccc1O)C(=O)O] |

| Example | Structure |
|---|---|
| 50. | 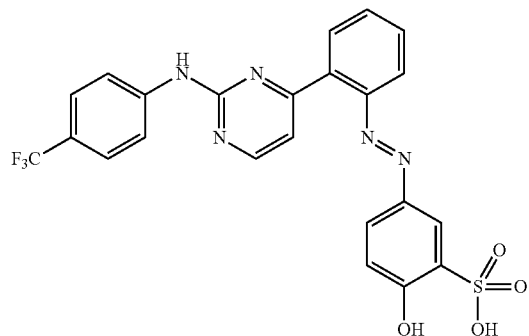 [SMILES: O=S(=O)(O)c1cc(/N=N/c2ccccc2-c2ccnc(Nc3ccc(C(F)(F)F)cc3)n2)ccc1O] |
| 51. | 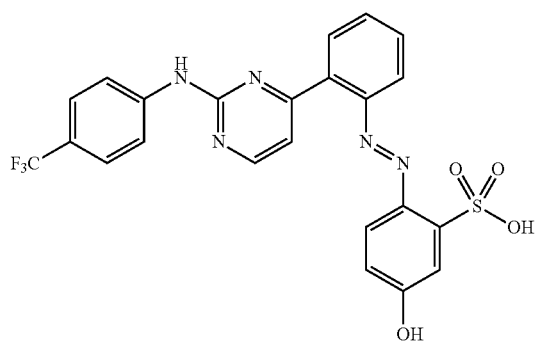 [SMILES: O=S(=O)(O)c1cc(O)ccc1/N=N/c1ccccc1-c1ccnc(Nc2ccc(C(F)(F)F)cc2)n1] |
| 52. | 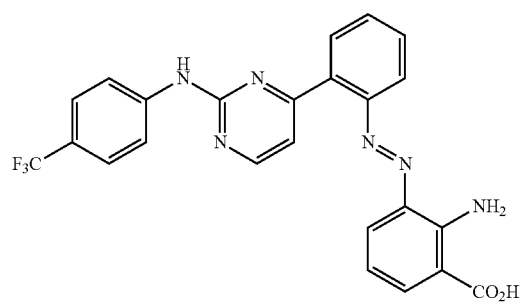 [SMILES: Nc1c(/N=N/c2ccccc2-c2ccnc(Nc3ccc(C(F)(F)F)cc3)n2)cccc1C(=O)O] |
| 53. | 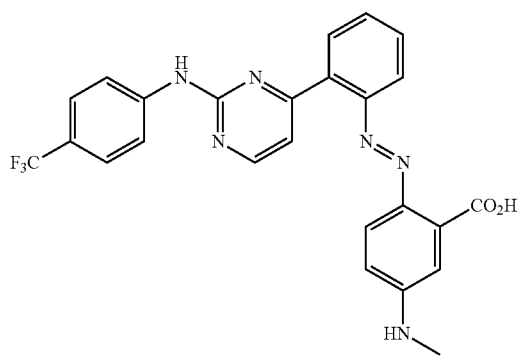 [SMILES: CNc1ccc(/N=N/c2ccccc2-c2ccnc(Nc3ccc(C(F)(F)F)cc3)n2)c(C(=O)O)c1] |

| Example | Structure |
|---|---|
| 54. | 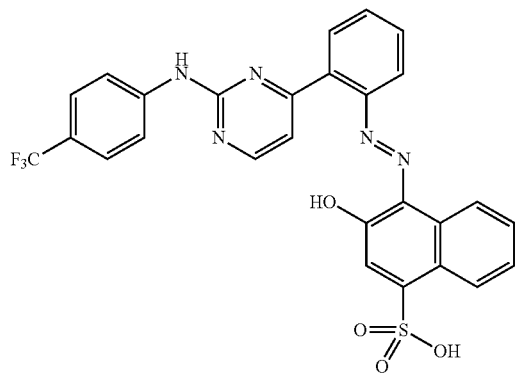 [SMILES: O=S(=O)(O)c1cc(O)c(/N=N/c2ccccc2-c2ccnc(Nc3ccc(C(F)(F)F)cc3)n2)c2ccccc12] |
| 55. | 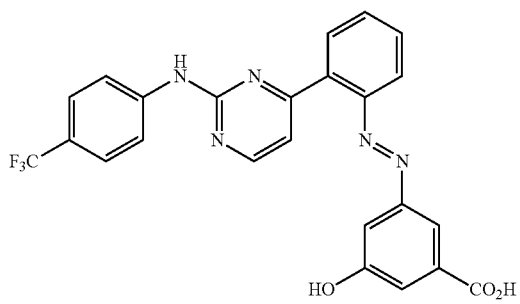 [SMILES: O=C(O)c1cc(O)cc(/N=N/c2ccccc2-c2ccnc(Nc3ccc(C(F)(F)F)cc3)n2)c1] |
| 56. | 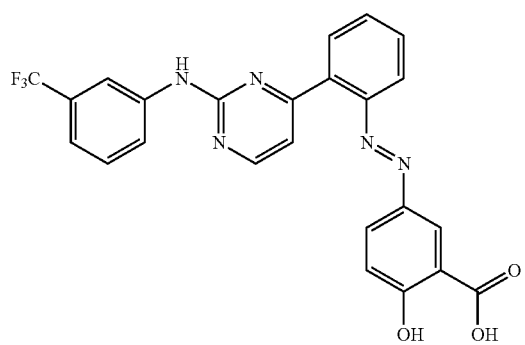 [SMILES: O=C(O)c1cc(/N=N/c2ccccc2-c2ccnc(Nc3cccc(C(F)(F)F)c3)n2)ccc1O] |
| 57. | 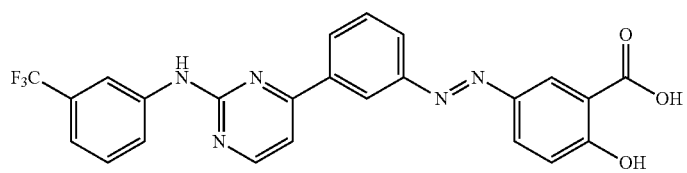 [SMILES: O=C(O)c1cc(/N=N/c2cccc(-c3ccnc(Nc4cccc(C(F)(F)F)c4)n3)c2)ccc1O] |
| 58. | 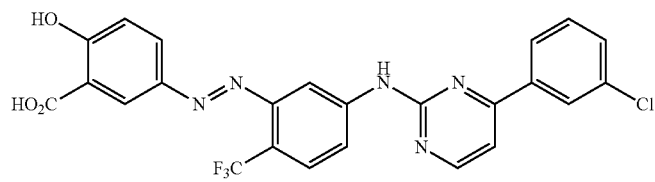 [SMILES: O=C(O)c1cc(/N=N/c2cc(Nc3nccc(-c4cccc(Cl)c4)n3)ccc2C(F)(F)F)ccc1O] |

| Example | Structure |
|---|---|
| 61. | 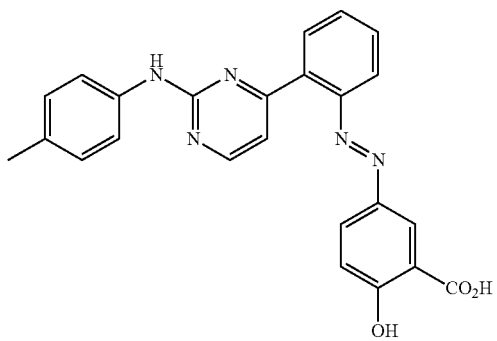 [SMILES: Cc1ccc(Nc2nccc(-c3ccccc3/N=N/c3ccc(O)c(C(=O)O)c3)n2)cc1] |
| 62. | 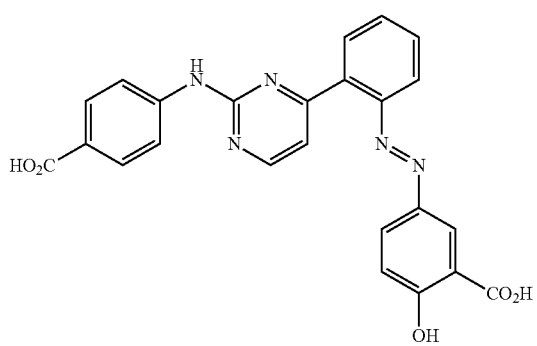 [SMILES: O=C(O)c1ccc(Nc2nccc(-c3ccccc3/N=N/c3ccc(O)c(C(=O)O)c3)n2)cc1] | or a pharmaceutically acceptable salt thereof.

11. The compound of claim 1, which is a compound of Formula (IA):

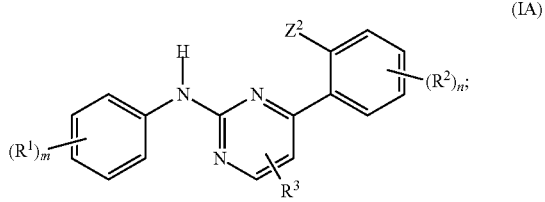

(IA)

wherein:
Z² is —N=N—Ar,
wherein Ar is selected from phenyl and naphthyl,
wherein each phenyl and naphthyl is optionally substituted with up to three groups selected from —OR, COOR, $C_{1-4}$ alkyl, $C_{1-4}$ haloalkyl, $C_{1-4}$ haloalkoxy, —NR₂, CN, —PO₃R², —SO₂R, —SO₃R, and halo;
R³ is selected from H, CN, halo, $C_{1-4}$ alkyl, $C_{1-4}$ haloalkyl, and $C_{1-4}$ haloalkoxy;
each R¹ is independently selected from —OR, COOR, $C_{1-4}$ haloalkyl, $C_{1-4}$ haloalkoxy, —NR₂, CN, —PO₃R², —SO₂R, —SO₃R, halo, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'₂;
each R is independently selected from H, $C_{1-4}$ haloalkyl, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'₂;

each R' is independently selected from H and $C_{1-3}$ alkyl;
each m is independently selected from 0, 1 and 2;
n is 0; and
[N] represents the attachment of Ar to N in —N=N—Ar;
or a pharmaceutically acceptable salt thereof.

12. The compound of claim 11, which is a compound of Formula (IB):

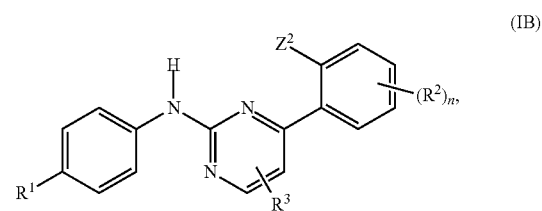

(IB)

or a pharmaceutically acceptable salt thereof.

13. The compound of claim 12, wherein R¹ is CF₃; or a pharmaceutically acceptable salt thereof.

14. The compound of claim 11, wherein R³ is H; or a pharmaceutically acceptable salt thereof.

15. The compound of claim 11, wherein Ar is selected from the group consisting of:

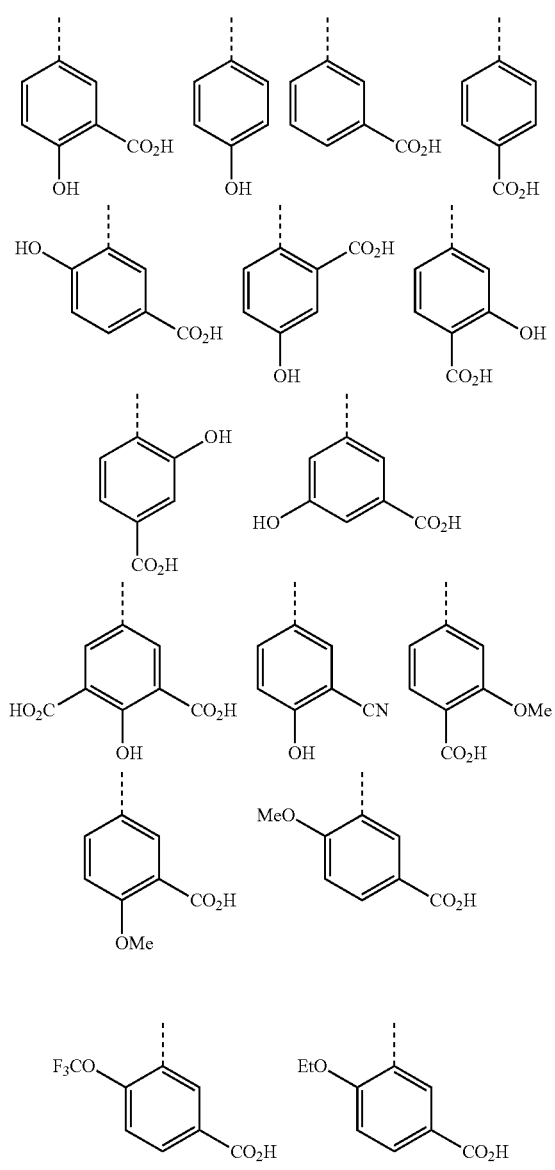
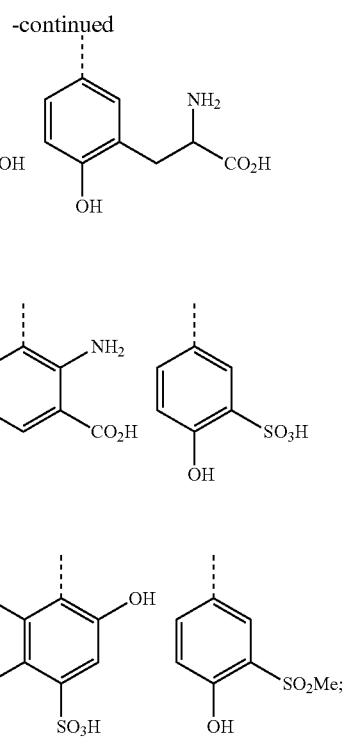

wherein the dashed bond indicates which atom of Ar is attached to N═N;
or a pharmaceutically acceptable salt thereof.

16. The compound of claim 15, wherein Ar is

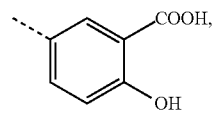

wherein the dashed bond indicates which atom of Ar is attached to N═N;
or a pharmaceutically acceptable salt thereof.

17. The compound of claim 1, which is of the Formula (IC):

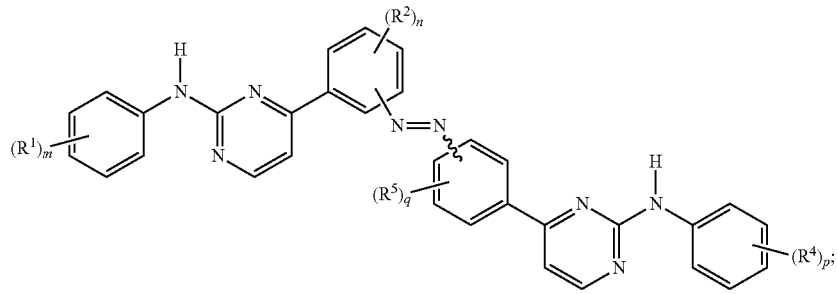

or a pharmaceutically acceptable salt thereof.

18. The compound of claim 17, which has the formula:

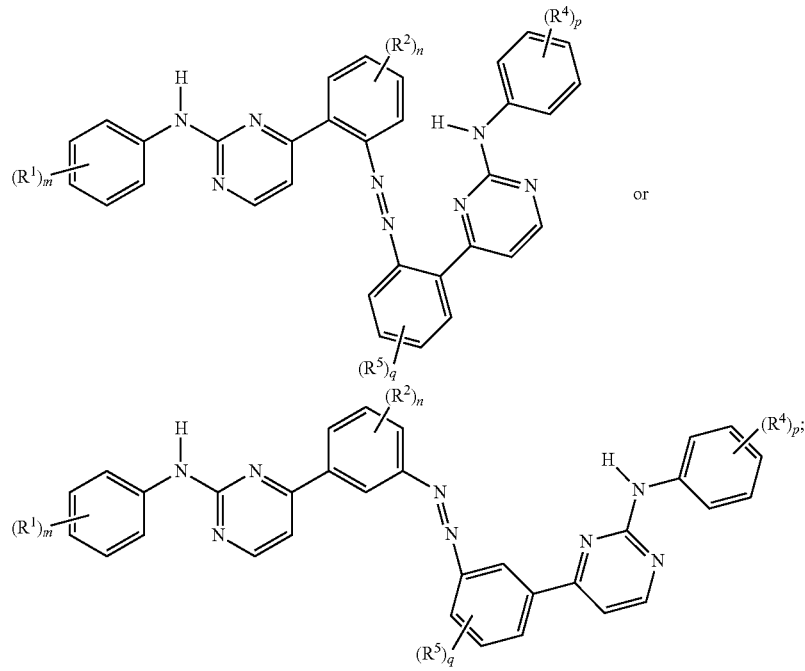

or a pharmaceutically acceptable salt thereof.

19. The compound of claim 18, wherein:
m is the same as p;
n is the same as q;
$R^1$ is the same as $R^4$; and
$R^2$ is the same as $R^5$;
or a pharmaceutically acceptable salt thereof.

20. A pharmaceutical composition comprising a compound of Formula (I):

$$\text{(I)}$$

wherein:
one of $Z^1$ and $Z^2$ is —N=N—Ar, and the other of $Z^1$ and $Z^2$ is H;
wherein Ar is selected from phenyl, naphthyl, and wherein each phenyl and naphthyl is optionally substituted with up to three groups selected from —OR, COOR, $C_{1-4}$ alkyl, $C_{1-4}$ haloalkyl, $C_{1-4}$ haloalkoxy, —NR$_2$, CN, —PO$_3$R$^2$, —SO$_2$R, —SO$_3$R, and halo;

$R^3$ is selected from H, CN, halo, $C_{1-4}$ alkyl, $C_{1-4}$ haloalkyl, and $C_{1-4}$ haloalkoxy;

each $R^1$ and $R^4$ is independently selected from —OR, COOR, $C_{1-4}$ haloalkyl, $C_{1-4}$ haloalkoxy, —NR$_2$, CN, —PO$_3$R$^2$, —SO$_2$R, —SO$_3$R, halo, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'$_2$;

each $R^2$ and $R^5$ is independently selected from halo, —OR, COOR, $C_{1-4}$ haloalkyl, $C_{1-4}$ haloalkoxy, —NR$_2$, CN, —PO$_3$R$^2$, —SO$_2$R, —SO$_3$R, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'$_2$;

each R is independently selected from H, $C_{1-4}$ haloalkyl, and $C_{1-4}$ alkyl optionally substituted with one or two groups selected from —OR', COOR', $C_{1-4}$ alkoxy, $C_{1-4}$ haloalkoxy, $C_{1-4}$ haloalkyl, —CN, and —NR'$_2$;

each R' is independently selected from H and $C_{1-3}$ alkyl;

each m, n, p, and q is independently selected from 0, 1 and 2; and

[N] represents the attachment of Ar to N in —N=N—Ar;

or a pharmaceutically acceptable salt thereof;

admixed with at least one pharmaceutically acceptable excipient.

* * * * *